United States Patent
Brister et al.

(10) Patent No.: US 10,335,303 B2
(45) Date of Patent: Jul. 2, 2019

(54) INTRAGASTRIC DEVICE

(71) Applicant: Obalon Therapeutics, Inc., Carlsbad, CA (US)

(72) Inventors: Mark C. Brister, Encinitas, CA (US); Neil R. Drake, San Diego, CA (US)

(73) Assignee: Obalon Therapeutics, Inc., Carlsbad, CA (US)

( * ) Notice: Subject to any disclaimer, the term of this patent is extended or adjusted under 35 U.S.C. 154(b) by 161 days.

(21) Appl. No.: 15/344,309

(22) Filed: Nov. 4, 2016

(65) Prior Publication Data
US 2017/0156909 A1 Jun. 8, 2017

Related U.S. Application Data

(60) Provisional application No. 62/264,280, filed on Dec. 7, 2015.

(51) Int. Cl.
*A61F 5/00* (2006.01)
*A61M 25/10* (2013.01)

(52) U.S. Cl.
CPC ............ *A61F 5/0089* (2013.01); *A61F 5/003* (2013.01); *A61F 5/0043* (2013.01); *A61M 25/1018* (2013.01); *A61M 2025/1054* (2013.01); *A61M 2025/1061* (2013.01); *A61M 2210/1053* (2013.01)

(58) Field of Classification Search
CPC ...... A61F 5/0089; A61F 5/003; A61F 5/0043; A61M 25/1018
See application file for complete search history.

(56) References Cited

U.S. PATENT DOCUMENTS

| | | |
|---|---|---|
| 2,183,900 A | 12/1939 | Voit et al. |
| 3,788,322 A | 1/1974 | Michaels |
| 3,797,492 A | 3/1974 | Place |
| 4,133,315 A | 1/1979 | Berman et al. |
| 4,234,454 A | 11/1980 | Strope |
| 4,236,521 A | 12/1980 | Lauterjung |

(Continued)

FOREIGN PATENT DOCUMENTS

| | | |
|---|---|---|
| DE | 35 40 936 C1 | 10/1986 |
| EP | 0 103 481 | 3/1984 |

(Continued)

OTHER PUBLICATIONS

Al Kahtani et al., Bio-Enteric Intragastric Balloon in Obese Patients: A Retrospective Analysis of King Faisal Specialist Hospital Experience; OBES SURG; Aug. 28, 2008.

(Continued)

*Primary Examiner* — Tuan V Nguyen
(74) *Attorney, Agent, or Firm* — Knobbe Martens Olson & Bear, LLP

(57) ABSTRACT

Devices and methods for treating obesity are provided. More particularly a device for assisting a patient in swallowing an intragastric balloon is provided, comprising an elongate tube, a gastric balloon assembly reversibly attached to an orifice of the elongate tube and comprising an inflation catheter engaged with a gastric balloon, a handle member, and an engagement subassembly comprising a female portion and a male portion and configured and arranged for threading the inflation catheter into and engaging the elongate tube.

18 Claims, 79 Drawing Sheets

(56) References Cited

U.S. PATENT DOCUMENTS

| | | |
|---|---|---|
| 4,246,893 A | 1/1981 | Berson |
| 4,340,626 A | 6/1982 | Rudy |
| 4,416,267 A | 11/1983 | Garren et al. |
| 4,485,805 A | 12/1984 | Foster, Jr. |
| 4,489,440 A | 12/1984 | Chaoui |
| 4,517,979 A | 5/1985 | Pecenka |
| 4,545,367 A | 10/1985 | Tucci |
| 4,560,392 A | 12/1985 | Basevi |
| 4,607,618 A | 8/1986 | Angelchik |
| 4,694,827 A | 9/1987 | Weiner et al. |
| 4,718,639 A | 1/1988 | Sherwood et al. |
| 4,723,547 A | 2/1988 | Kullas et al. |
| 4,739,758 A | 4/1988 | Lai et al. |
| 4,812,315 A | 3/1989 | Tarabishi |
| 4,813,934 A | 3/1989 | Engelson et al. |
| 4,857,029 A | 8/1989 | Dierick et al. |
| 4,899,747 A | 2/1990 | Garren et al. |
| 4,917,885 A | 4/1990 | Chiba et al. |
| 4,925,446 A | 5/1990 | Garay et al. |
| 4,929,214 A | 5/1990 | Liebermann |
| 5,049,106 A | 9/1991 | Kim et al. |
| 5,084,061 A | 1/1992 | Gau et al. |
| 5,129,915 A | 7/1992 | Cantenys et al. |
| 5,213,141 A | 5/1993 | Dorman |
| 5,234,454 A | 8/1993 | Bangs |
| 5,259,399 A | 11/1993 | Brown |
| 5,308,326 A | 5/1994 | Zimmon |
| 5,431,917 A | 7/1995 | Yamamoto et al. |
| 5,603,698 A * | 2/1997 | Roberts .................. A61F 2/95 604/104 |
| 5,713,141 A | 2/1998 | Mitchell et al. |
| 5,728,119 A | 3/1998 | Smith et al. |
| 5,852,889 A | 12/1998 | Rinaldi |
| 5,868,141 A | 2/1999 | Ellias |
| 5,897,205 A | 4/1999 | Sinsteden |
| 5,910,128 A | 6/1999 | Quinn |
| 6,427,089 B1 | 7/2002 | Knowlton |
| 6,454,785 B2 | 9/2002 | De Hoyos Garza |
| 6,579,301 B1 | 6/2003 | Bales et al. |
| 6,682,473 B1 | 1/2004 | Matsuura et al. |
| 6,689,141 B2 | 2/2004 | Ferrera |
| 6,733,512 B2 | 5/2004 | McGhan |
| 6,981,980 B2 | 1/2006 | Sampson et al. |
| 6,988,983 B2 | 1/2006 | Connors et al. |
| 7,192,397 B2 | 3/2007 | Lewkowicz et al. |
| 7,682,306 B2 | 3/2010 | Shah |
| 7,699,863 B2 | 4/2010 | Marco et al. |
| 7,854,745 B2 | 12/2010 | Brister et al. |
| 8,162,969 B2 | 4/2012 | Brister et al. |
| 8,202,291 B1 | 6/2012 | Brister et al. |
| 8,282,666 B2 | 10/2012 | Birk |
| 8,292,911 B2 | 10/2012 | Brister et al. |
| 8,562,589 B2 | 10/2013 | Imran |
| 8,647,358 B2 | 2/2014 | Brister et al. |
| 8,721,620 B2 | 5/2014 | Imran |
| 8,734,429 B2 | 5/2014 | Imran et al. |
| 8,740,911 B2 | 6/2014 | Brister et al. |
| 8,764,733 B2 | 7/2014 | Imran |
| 8,809,269 B2 | 8/2014 | Imran |
| 8,809,271 B2 | 8/2014 | Imran |
| 8,845,674 B2 | 9/2014 | Brister et al. |
| 8,870,966 B2 | 10/2014 | Schwab et al. |
| 8,992,561 B2 | 3/2015 | Brister et al. |
| 9,011,477 B2 | 4/2015 | Brister et al. |
| 9,072,583 B2 | 7/2015 | Brister et al. |
| 9,173,758 B2 | 11/2015 | Brister et al. |
| 9,351,862 B2 | 5/2016 | Brister et al. |
| 9,468,550 B2 | 10/2016 | Brister et al. |
| 2003/0021822 A1 | 1/2003 | Lloyd |
| 2003/0171768 A1 | 9/2003 | McGhan |
| 2004/0044351 A1 | 3/2004 | Searle |
| 2004/0102677 A1 | 5/2004 | Frering |
| 2004/0186502 A1 | 9/2004 | Sampson |
| 2005/0192614 A1 | 9/2005 | Binmoelier |
| 2005/0222329 A1 | 10/2005 | Shah et al. |
| 2005/0266109 A1 | 12/2005 | Chin et al. |
| 2005/0267405 A1 | 12/2005 | Shah |
| 2005/0267595 A1 | 12/2005 | Chen et al. |
| 2006/0058829 A1 | 3/2006 | Sampson et al. |
| 2006/0178691 A1 | 8/2006 | Binmoelier |
| 2006/0224145 A1 | 10/2006 | Gillis et al. |
| 2007/0078476 A1 | 4/2007 | Hull et al. |
| 2007/0100208 A1 | 5/2007 | Lewkowicz et al. |
| 2007/0100369 A1 | 5/2007 | Cragg et al. |
| 2007/0104754 A1 | 5/2007 | Sterling et al. |
| 2007/0104755 A1 | 5/2007 | Sterling et al. |
| 2007/0110934 A1 | 5/2007 | Goldman |
| 2007/0149994 A1 | 6/2007 | Sosnowski et al. |
| 2007/0156248 A1 | 7/2007 | Marco et al. |
| 2007/0173881 A1 | 7/2007 | Birk et al. |
| 2007/0207199 A1 | 9/2007 | Sogin et al. |
| 2007/0212559 A1 | 9/2007 | Shah |
| 2007/0250101 A1 | 10/2007 | Horn et al. |
| 2007/0288033 A1 | 12/2007 | Murature et al. |
| 2007/0293885 A1 | 12/2007 | Binmoelier |
| 2008/0051866 A1 | 2/2008 | Chen et al. |
| 2008/0172079 A1 | 7/2008 | Birk |
| 2008/0255601 A1 | 10/2008 | Birk |
| 2008/0306506 A1 | 12/2008 | Leatherman et al. |
| 2009/0082644 A1 | 3/2009 | Li |
| 2009/0118756 A1 | 5/2009 | Valencon et al. |
| 2009/0182368 A1 | 7/2009 | Lunsford et al. |
| 2009/0182424 A1 | 7/2009 | Marco et al. |
| 2009/0187206 A1 | 7/2009 | Binmoelier et al. |
| 2009/0192535 A1 | 7/2009 | Kasic, II et al. |
| 2009/0222065 A1 | 9/2009 | Dlugos et al. |
| 2009/0259246 A1 | 10/2009 | Eskaros et al. |
| 2010/0063530 A1 | 3/2010 | Valencon |
| 2010/0100115 A1 | 4/2010 | Soetermans et al. |
| 2010/0100116 A1 | 4/2010 | Brister et al. |
| 2010/0100117 A1 | 4/2010 | Brister et al. |
| 2010/0137897 A1 | 6/2010 | Brister et al. |
| 2010/0168782 A1 | 7/2010 | Hancock |
| 2010/0198249 A1 | 8/2010 | Sabliere |
| 2010/0222802 A1 | 9/2010 | Gillespie et al. |
| 2011/0202127 A1 | 8/2011 | Mauch et al. |
| 2011/0295300 A1 | 12/2011 | Verd et al. |
| 2012/0010590 A1 | 1/2012 | Imran |
| 2012/0296365 A1 | 11/2012 | Nguyen |
| 2013/0165859 A1 | 6/2013 | Imran |
| 2013/0226219 A1 | 8/2013 | Brister et al. |
| 2013/0267983 A1 | 10/2013 | Pavlovic et al. |
| 2014/0066968 A1 | 3/2014 | Pavlovic et al. |
| 2014/0221912 A1 | 8/2014 | Imran |
| 2014/0221927 A1 | 8/2014 | Imran et al. |
| 2014/0364894 A1 | 12/2014 | Brister et al. |
| 2015/0257911 A1 | 9/2015 | Brister et al. |
| 2015/0374525 A1 | 12/2015 | Brister et al. |
| 2016/0008154 A1 | 1/2016 | Brister et al. |
| 2016/0029998 A1 | 2/2016 | Brister et al. |
| 2016/0058322 A1 | 3/2016 | Brister et al. |
| 2016/0100970 A1 | 4/2016 | Brister et al. |
| 2016/0193064 A1 | 7/2016 | Brister et al. |
| 2016/0256308 A1 | 9/2016 | Brister et al. |
| 2016/0278662 A1 | 9/2016 | Brister et al. |

FOREIGN PATENT DOCUMENTS

| | | |
|---|---|---|
| EP | 0 246 999 | 11/1987 |
| JP | 62-286470 | 12/1987 |
| WO | WO 87/00034 | 1/1987 |
| WO | WO 99/25418 | 5/1999 |
| WO | WO 01/68007 | 9/2001 |
| WO | WO 02/16001 | 2/2002 |
| WO | WO 02/40081 | 5/2002 |
| WO | WO 02/091961 | 11/2002 |
| WO | WO 03/055420 | 7/2003 |
| WO | WO 04/084763 | 10/2004 |
| WO | WO 06/020929 | 2/2006 |
| WO | WO 07/136735 | 11/2007 |
| WO | WO 10/045482 | 10/2008 |
| WO | WO 09/055386 | 4/2009 |
| WO | WO 09/059802 | 5/2009 |
| WO | WO 09/059803 | 5/2009 |

(56) References Cited

FOREIGN PATENT DOCUMENTS

| WO | WO 09/086119 | 7/2009 |
|---|---|---|
| WO | WO 10/045477 | 4/2010 |
| WO | WO 2016/171763 | 10/2016 |
| WO | WO 2016/172054 | 10/2016 |

OTHER PUBLICATIONS

Al-Momen et al., Intragastric Balloon for Obesity: A Retrospective Evaluation of Tolerance and Efficacy; OBES SURG; 2005;15(1):101-5.
Benjamin et al., Double-Blind Controlled Trial of the Garren-Edwards Gastric Bubble: An Adjunctive Treatment for Exogenous Obesity, Gastroenterology, vol. 95, No. 3, pp. 581-588, Sep. 1988.
Brister et al., U.S. Appl. No. 15/097,072, filed Apr. 12, 2016.
Brister et al., U.S. Appl. No. 15/290,977, filed Oct. 11, 2016.
Brister et al., U.S. Appl. No. 15/335,256, filed Oct. 26, 2016.
Carvalho et al., An Improved Intragastric Balloon Procedure Using a New Balloon: Preliminary Analysis of Safety and Efficacy, OBES SURG, 2008.
Coskun et al., Bioenterics Intragastric Balloon: Clinical Outcomes of the First 100 Patients—A Turkish Experience, OBES SURG, Sep. 2008; 18(9):1154-6. published online Jun. 3, 2008.
Dastis et al., Intragastric Balloon for Weight Loss: Results in 100 Individuals Followed for At Least 2.5 Years; Endoscopy. Jul. 2009; 41(7):575-80; published online Jul. 8, 2009.
De Waele et al., Endoscopic Volume Adjustment of Intragastric Balloons for Intolerance, OBES SURG; Apr. 2001; 11(2):223-4.
Doldi et al., Treatment of Morbid Obesity With Intragastric Balloon in Association With Diet; OBES SURG; 2002; 12(4):583-7.
Dumonceau, Evidence-Based Review of the Bioenterics Intragastric Balloon for Weight Loss, OBES SURG. Dec. 2008;18(12):1611-7. published online Jun. 21, 2008.
Durrans et al., Comparison of Weight Loss With Short Term Dietary and Intragastric Balloon Treatment; Gut 1989, 30, 565-568.
Eckhauser et al., Hydrostatic Balloon Dilation for Stomal Stenosis after Gastric Partitioning, Surgical Gastroenterology, vol. 3, No. 1, pp. 43-50, 1984.
Evans et al., Intragastric Balloon in the Treatment of Patients With Morbid Obesity, British Journal of Surgery; 2001; 88:1245-1248.
Fernandes et al., Intragastric Balloon for Obesity (Review); Cochrane Review; Jan. 24, 2007; Issue 1.
Forestieri et al., Heliosphere Bag in the Treatment of Severe Obesity: Preliminary Experience, Obes Surg; May 2006; 16(5):635-7.
Gaggiotti et al., Adjustable Totally Implanted Intragastric Prosthesis (ATIIP). Endogast for Treatment of Morbid Obesity: One Year Follow-Up of a Multicenter Prospective Clinical Survey; Obesity Surgery. 2007: 17, 949-956.
Geliebter et al., Gastric balloon to treat obesity: a double-blind study in nondieting subjects, The American Journal of Clinical Nutrition, vol. 51, pp. 584-588, 1990.
Genco et al., Bioenterics Intragastric Balloon (BIB): A Short-Term, Double-Blind, Randomized, Controlled, Crossover Study on Weight Reduction in Morbidly Obese Patients; International Journal of Obesity (Lond); Jan. 2006; 30(1):129-33; published online Sep. 27, 2005.
Genco et al., Bioenterics Intragastric Balloon: The Italian Experience With 2,515 Patients; OBES SURG; 2005: 15(8):1161-4.
Genco et al., Intragastric Balloon or Diet Alone? A Retrospective Evaluation, OBES SURG, Aug. 2008; 18(8):989-92. published online May 16, 2008.
Genco et al., Laparoscopic Sleeve Gastrectomy Versus Intragastric Balloon: A Case-Control Study, Surg Endosc. Springer Science & Business Media, published online Jan. 24, 2009.
Gottig et al., Analysis of Safety and Efficacy of Intragastric Balloon in Extremely Obese Patients, OBES SURG, Jun. 2009; 19(6):677-83. published online Mar. 17, 2009.
Imaz et al., Safety and Effectiveness of the Intragastric Balloon for Obesity. A Meta-Analysis; OBES SURG; Jul. 2008;18(7):841-6; published online May 6, 2008.
Langer, R., Drug delivery and targeting, Nature, Suuplement to vol. 392, No. 6679, pp. 5-10, Apr. 1998.
Malik; Endoluminal and Transluminal Surgery: Current Status and Future Possibilities; Surgical Endoscopy; 2006; 20(8):1179-92.
Martin et al., Safety of the Ullorex Oral Intragastric Balloon for the Treatment of Obesity, Journal of Diabetic Science and Technology, vol. 1, Issue 4, pp. 574-581, Jul. 2007.
Mathus-Vliegen et al., Intragastric Ballon in the Treatment of Super-morbid Obesity—Double-Blind, Sham-Controlled, Cross-over Evaluation of 500-Milliliter Balloon, Gastroenterology, vol. 99, No. 2, pp. 362-369, Aug. 1990.
Melissas et al., The Intragastric Balloon—Smoothing the Path to Bariatric Surgery, OBES SURG 2006; 16:897-902.
Mion et al., Tolerance and Efficacy of an Air-Filled Balloon in Non-Morbidly Obese Patients: Results of a Prospective Multicenter Study; OBES SURG; Jul. 2007; 17(7):764-769.
Nieben et al., Ingtragastric Balloon as an Artificial Bezoar for Treatment of Obesity, The Lancet, vol. 1, No. 8265, pp. 198-199, Jan. 1982.
Ramhamadany et al, Effect of the Gastric Balloon Versus Sham Procedure on Weight Loss in Obese Subjects; Gut 1989; 30; 1054-1057.
Rodriguez-Hermosa et al., Gastric Necrosis: A Possible Complication of the Use of the Intragastric Balloon in a Patient Previously Submitted to Nissen Fundoplication; OBES SURG; 19:1456-1459; published online Jun. 9, 2009.
Roman et al., Intragastric Balloon for "Non-Morbid" Obesity: A Retrospective Evaluation of Tolerance and Efficacy; OBES SURG; Apr. 2004; 14(4):539-44.
Sallet et. al. Brazilian Multicenter Study of the Intragastric Balloon; Obesity Surgery; Aug. 2004; 14(7); 991-998.
Totte et al., Weight Reduction by Means of Intragastric Device: Experience With the Bioenterics Intragastric Balloon; OBES SURG; Aug. 2001; 11(4):519-23.
Trande et al., Efficacy, Tolerance and Safety of New Intragastric Air-Filled Balloon (Heliosphere BAG) for Obesity: The Experience of 17 Cases; OBES SURG; Dec. 10, 2008.
Vansonnenberg et al., Percutaneous Gastrostomy: Use of Intragastric Ballon Support, Radiology, vol. 152, No. 2, pp. 531-532, Aug. 1984.
Wahlen et al., The Bioenterics Intragastric Balloon (BIB): How to Use It; OBES SURG; 2001;11(4):524-7.

\* cited by examiner

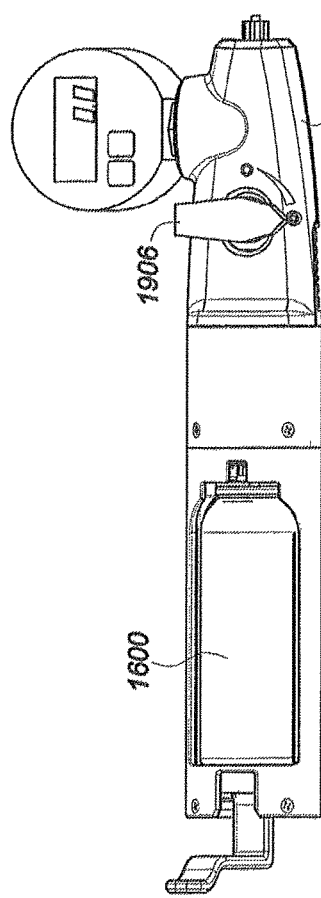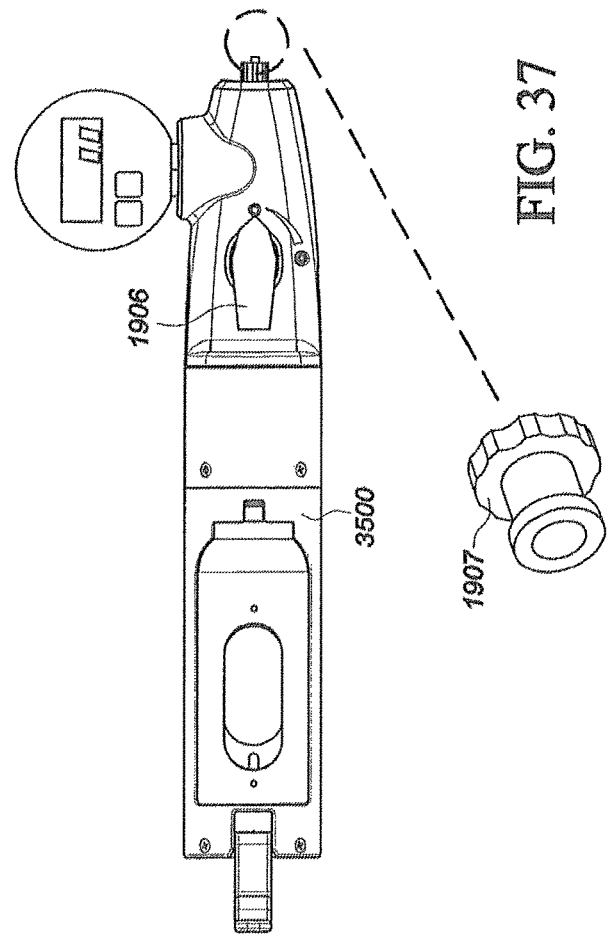

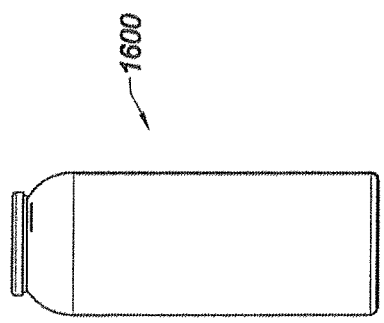
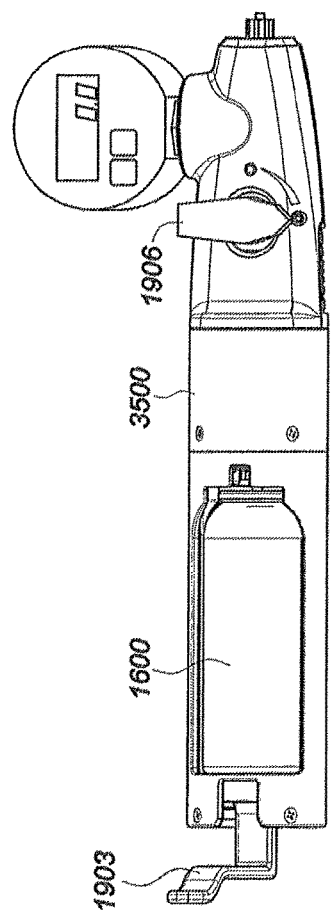

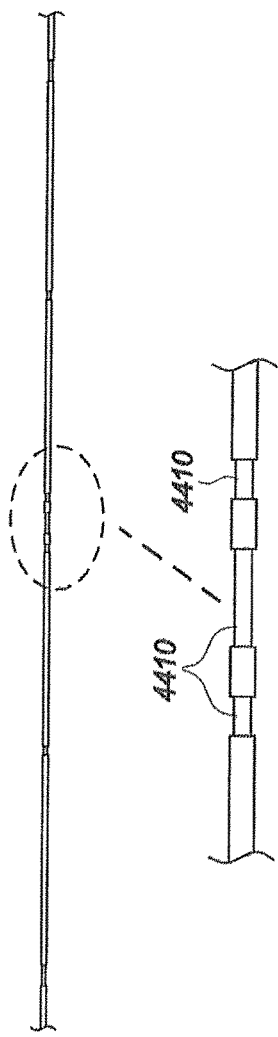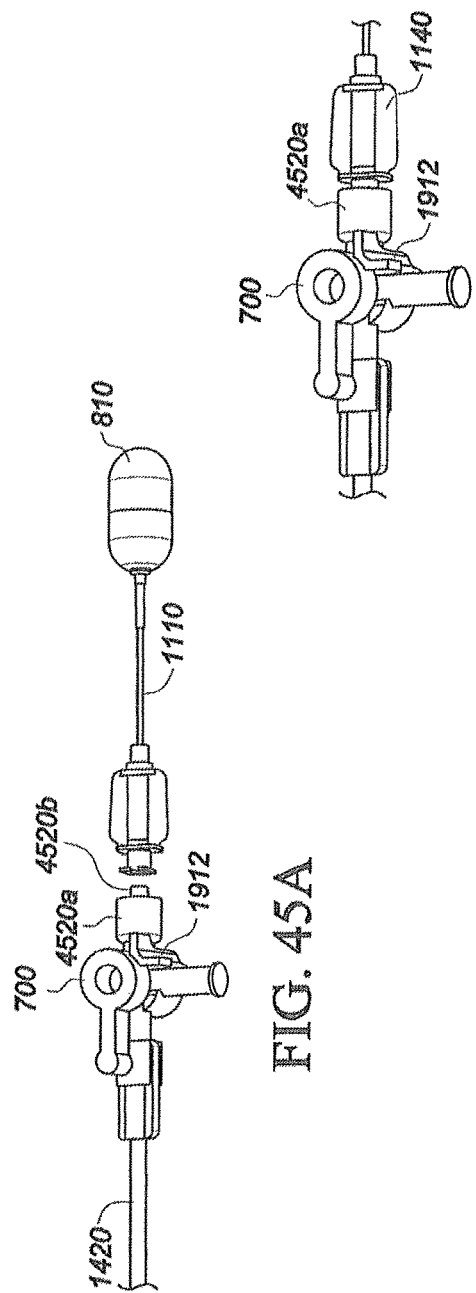

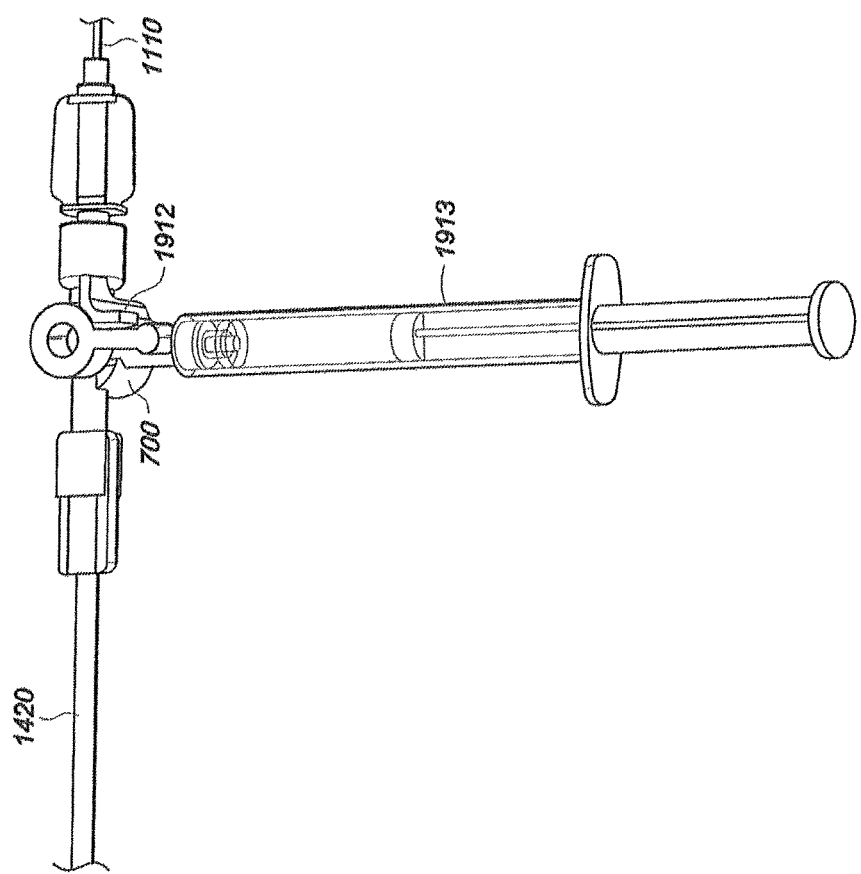

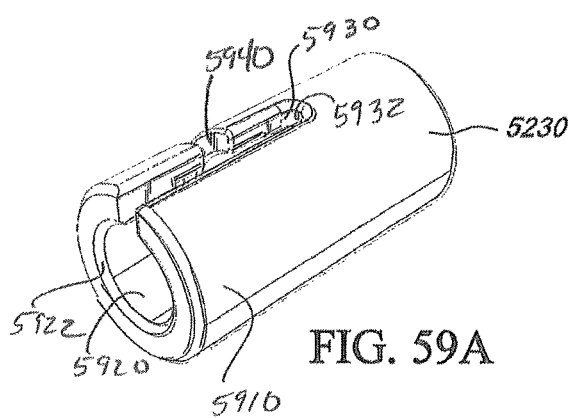
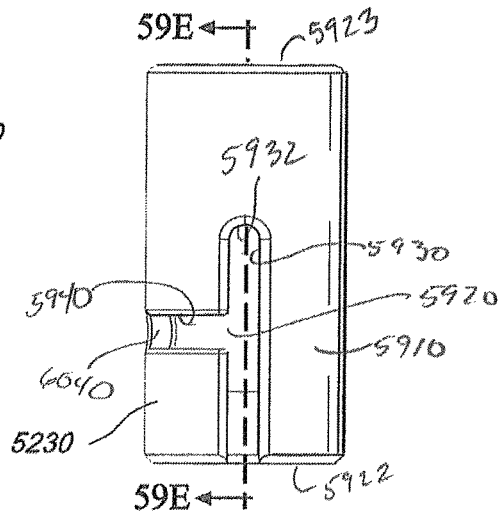
FIG. 59A
FIG. 59B
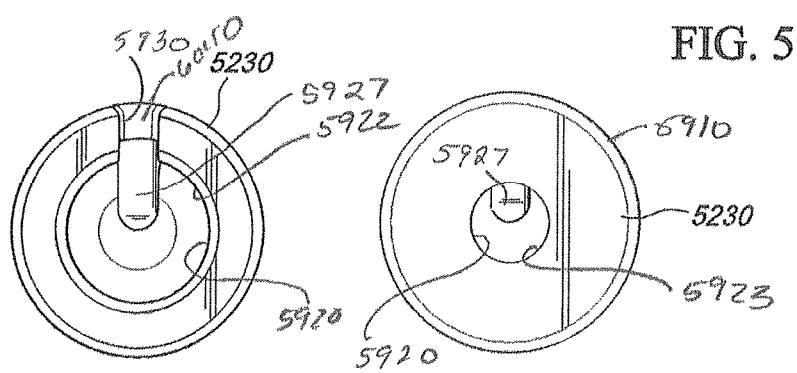
FIG. 59C  FIG. 59D
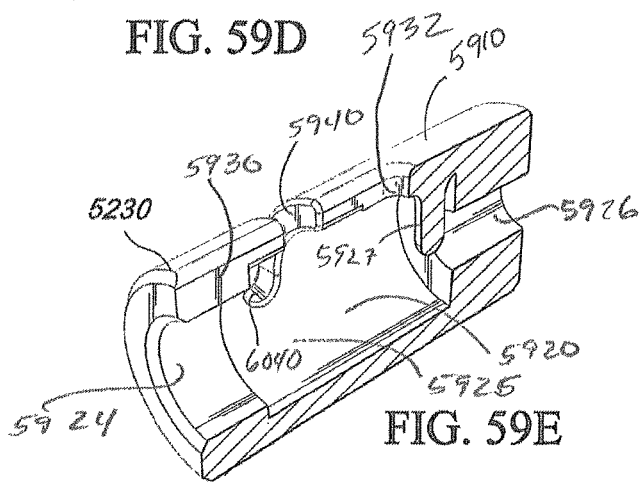
FIG. 59E

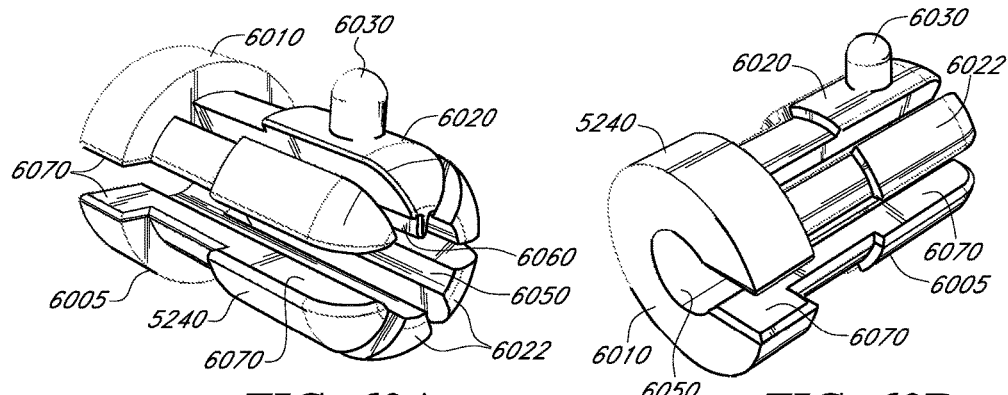
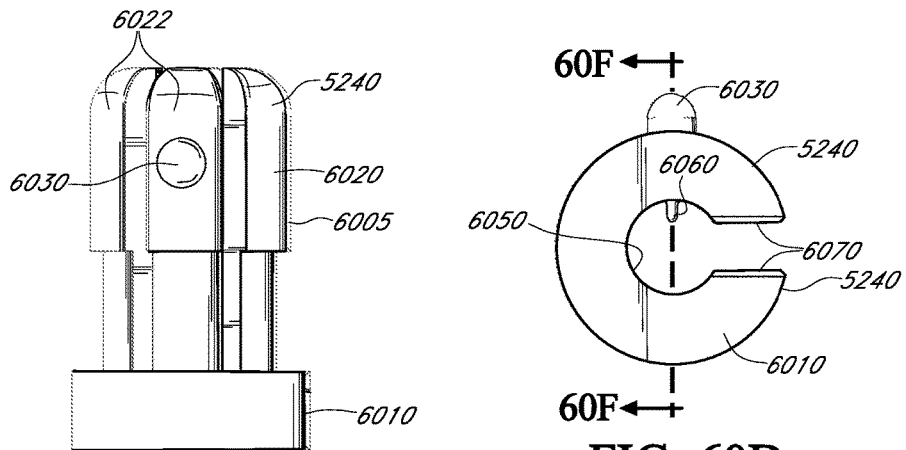
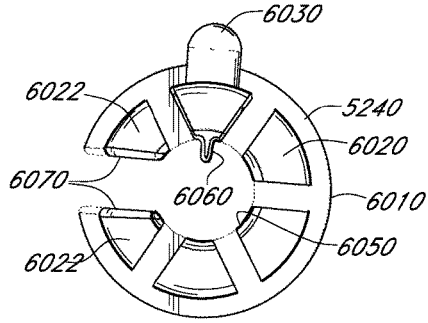
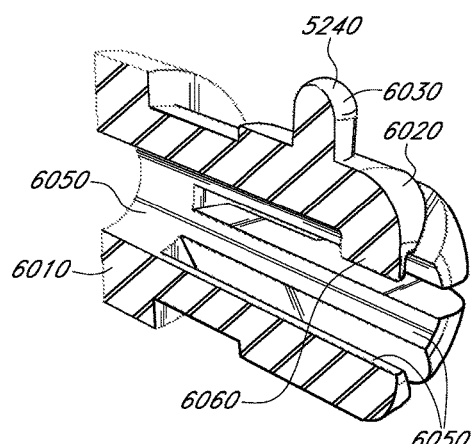
FIG. 60A    FIG. 60B    FIG. 60C    FIG. 60D    FIG. 60E    FIG. 60F

INTRAGASTRIC DEVICE

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 62/264,280, filed on Dec. 7, 2015. The aforementioned application is incorporated by reference herein in its entirety, and is hereby expressly made a part of this specification.

FIELD OF THE INVENTION

Devices and methods for treating obesity are provided. More particularly, intragastric devices and methods of fabricating, deploying, inflating, monitoring, and retrieving the same are provided.

BACKGROUND OF THE INVENTION

Obesity is a major health problem in developed countries. Obesity puts you at greater risk of developing high blood pressure, diabetes and many other serious health problems. In the United States, the complications of being overweight or obese are estimated to affect nearly one in three American adults, with an annual medical cost of over $80 billion and, including indirect costs such as lost wages, a total annual economic cost of over $120 billion. Except for rare pathological conditions, weight gain is directly correlated to overeating. Noninvasive methods for reducing weight include increasing metabolic activity to burn calories and/or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the person is satisfied with a feeling of fullness. Currently available volume-occupying devices have many shortcomings. For example, complex gastric procedures are required to insert some devices.

U.S. Pat. No. 4,133,315, the contents of which are incorporated herein by reference in their entirety, discloses an apparatus for reducing obesity comprising an inflatable, elastomeric bag and tube combination. The bag can be inserted into the patient's stomach by swallowing. The end of the attached tube distal to the bag remains in the patient's mouth. A second tube is snaked through the nasal cavity and into the patient's mouth. The tube ends located in the patient's mouth are connected to form a continuous tube for fluid communication through the patient's nose to the bag. Alternatively, the bag can be implanted by a gastric procedure. The bag is inflated through the tube to a desired degree before the patient eats so that the desire for food is reduced. After the patient has eaten, the bag is deflated. The tube extends out of the patient's nose or abdominal cavity throughout the course of treatment.

U.S. Pat. Nos. 5,259,399, 5,234,454 and 6,454,785, the contents of which are incorporated herein by reference in their entirety, disclose intragastric volume-occupying devices for weight control that must be implanted surgically.

U.S. Pat. Nos. 4,416,267, 4,485,805, 4,607,618, 4,694,827, 4,723,547, 4,739,758, and 4,899,747 and European Patent No. 246,999, the contents of which are incorporated herein by reference in their entirety, relate to intragastric, volume-occupying devices for weight control that can be inserted endoscopically. Of these, U.S. Pat. Nos. 4,416,267, 4,694,827, 4,739,758 and 4,899,747, the contents of which are incorporated herein by reference in their entirety relate to balloons whose surface is contoured in a certain way to achieve a desired end. In U.S. Pat. Nos. 4,416,267 and 4,694,827, the contents of which are incorporated herein by reference in their entirety, the balloon is torus-shaped with a flared central opening to facilitate passage of solids and liquids through the stomach cavity. The balloon of U.S. Pat. No. 4,694,827, the contents of which are incorporated herein by reference in their entirety, has a plurality of smooth-surfaced convex protrusions. The protrusions reduce the amount of surface area which contacts the stomach wall, thereby reducing the deleterious effects resulting from excessive contact with the gastric mucosa. The protrusions also define channels between the balloon and stomach wall through which solids and liquids may pass. The balloon of U.S. Pat. No. 4,739,758, the contents of which are incorporated herein by reference in their entirety, has blisters on its periphery that prevent it from seating tightly against the cardia or pylorus.

The balloons of U.S. Pat. Nos. 4,899,747 and 4,694,827, the contents of which are incorporated herein by reference in their entirety, are inserted by pushing the deflated balloon and releasably attached tubing down a gastric tube. U.S. Pat. No. 4,723,547, the contents of which are incorporated herein by reference in their entirety discloses a specially adapted insertion catheter for positioning its balloon. In U.S. Pat. No. 4,739,758, the contents of which are incorporated herein by reference in their entirety, the filler tube effects insertion of the balloon. In U.S. Pat. No. 4,485,805, the contents of which are incorporated herein by reference in their entirety, the balloon is inserted into a finger cot that is attached by string to the end of a conventional gastric tube that is inserted down the patient's throat. The balloon of European Patent No. 246,999 is inserted using a gastroscope with integral forceps.

In U.S. Pat. Nos. 4,416,267, 4,485,805, 4,694,827, 4,739,758, and 4,899,747 and European Patent No. 246,999, the contents of which are incorporated herein by reference in their entirety, the balloon is inflated with a fluid from a tube extending down from the patient's mouth. In these patents, the balloon also is provided with a self-sealing hole (U.S. Pat. No. 4,694,827, the contents of which are incorporated herein by reference in their entirety), injection site (U.S. Pat. Nos. 4,416,267 and 4,899,747, the contents of which are incorporated herein by reference in their entirety), self-sealing fill valve (U.S. Pat. No. 4,485,805, the contents of which are incorporated herein by reference in their entirety), self-closing valve (European Patent No. 246,999, the contents of which are incorporated herein by reference in their entirety) or duck-billed valve (U.S. Pat. No. 4,739,758, the contents of which are incorporated herein by reference in their entirety). U.S. Pat. No. 4,723,547, the contents of which are incorporated herein by reference in their entirety, uses an elongated thick plug and the balloon is filled by inserting a needle attached to an air source through the plug.

U.S. Pat. No. 4,607,618, the contents of which are incorporated herein by reference in their entirety, describes a collapsible appliance formed of semi-rigid skeleton members joined to form a collapsible hollow structure. The appliance is not inflatable. It is endoscopically inserted into the stomach using an especially adapted bougie having an ejector rod to release the collapsed appliance. Once released, the appliance returns to its greater relaxed size and shape.

U.S. Pat. No. 5,129,915, the contents of which are incorporated herein by reference in their entirety, the contents of which are incorporated herein by reference, relates to an intragastric balloon that is intended to be swallowed and that inflates automatically under the effect of temperature. Three ways that an intragastric balloon might be inflated by a change in temperature are discussed. A composition comprising a solid acid and non-toxic carbonate or bicarbonate is separated from water by a coating of chocolate, cocoa paste or cocoa butter that melts at body temperature. Alternatively, citric acid and an alkaline bicarbonate coated with non-toxic vegetable or animal fat melting at body temperature and which placed in the presence of water, can produce the same result. Lastly, the solid acid and non-toxic carbonate or bicarbonate are isolated from water by an isolation pouch of low-strength synthetic material which it will suffice to break immediately before swallowing the bladder. Breaking the isolation pouches causes the acid, carbonate or bicarbonate and water to mix and the balloon to begin to expand immediately. A drawback of thermal triggering of inflation is that it does not afford the degree of control and reproducibility of the timing of inflation that is desirable and necessary in a safe self-inflating intragastric balloon.

SUMMARY OF THE INVENTION

A free-floating, intragastric, volume-occupying device that can be inserted into the stomach by the patient swallowing it and letting peristalsis deliver it into the stomach in the same manner that food is delivered, or by positioning it with a catheter, is desirable.

Volume-occupying devices and methods for manufacturing, deploying, inflating, tracking, deflating and retrieving of such devices are provided. The devices and methods of the preferred embodiments may be employed for treating overweight and obese individuals. Methods employing the device of the preferred embodiments may be swallowed by a patient, with or without a catheter attached. Once in the stomach of the patient, the device is inflated with a preselected gas or mixture of gases, to a preselected volume. After a predetermined time period, the device can be removed using endoscopic tools or decreases in volume or deflate so as to pass through the remainder of the patient's digestive tract.

Inflation may be achieved by use of a removable catheter that initially remains in fluid contact with the device after it has been swallowed by the patient.

The volume-occupying subcomponent of devices may be formed by injection, blow or rotational molding of a flexible, gas-impermeable, biocompatible material, such as, for example, polyurethane, nylon or polyethylene terephthalate. Materials that may be used to control the gas permeability/impermeability of the volume-occupying subcomponent include, but are not limited to, silicon oxide (SiOx), gold or any noble metal, saran, conformal coatings and the like, when it is desired to reduce permeability. To enhance gas-impermeable characteristics of the wall of the device, if desirable, the volume-occupying subcomponent may be further coated with one or more gas-barrier compounds, or be formed of a Mylar polyester film coating or kelvalite, silver or aluminum as a metallicized surface to provide a gas impermeable barrier.

In further embodiments, the device employs a delivery state in which the device is packaged such that the device may be swallowed while producing minimal discomfort to the patient. In a delivery state, the device may be packaged into a capsule. Alternatively, the device may be coated with a material operable to confine the device and facilitate swallowing. Various techniques may also be employed to ease swallowing of the device including, for example, wetting, temperature treating, lubricating, and treating with pharmaceuticals such as anesthetics.

In other embodiments, the devices may incorporate a tracking or visualization component that enables physicians to determine the location and/or orientation of the device within the patient's body. Tracking subcomponents may include incorporating a barium stripe or geometric shape into the wall of the volume-occupying subcomponent. Tracking and visualization, may also be achieved by incorporation of a microchip, infrared LED tag, ultraviolet absorbing compounds, fluorescent or colored compounds and incorporation of metallized strips and patterns into the volume-occupying subcomponent or other subcomponents of the device. Such techniques may also be used to obtain certain device specific information and specifications while the device remains inside the patient's body.

In a first aspect, a system is provided for inflating an intragastric balloon, the system comprising: an inflation catheter, wherein the inflation catheter comprises a needle assembly comprising a hollow needle, a bell-shaped needle sleeve, and a mechanism for detachment of the inflation catheter after inflation of a balloon in vivo is complete; an intragastric balloon comprising a polymeric wall, wherein the polymeric wall comprises one or more layers, and a balloon valve system comprising a self-sealing septum in a retaining structure, wherein the septum is configured for piercing by the needle, wherein the retaining structure comprises a concentric valve system with a smaller inner cylinder housing the septum and a larger outer cylinder housing a material providing compressive forces against the bell-shaped needle sleeve of the inflation catheter for inflation and detachment, wherein the material providing compressive forces is a harder durometer material than the septum, and wherein the smaller inner cylinder comprises a lip configured for an interference fit with the bell-shaped needle sleeve to provide sealing of the valve to the inflation catheter sufficient to maintain the seal during inflation of the balloon; a balloon outer container; and an inflation source container, wherein the inflation source container is configured to connect to the inflation catheter; wherein the inflation catheter connected to the intragastric balloon prior to inflation is of a size and shape configured for swallowing by a patient in need thereof.

In an embodiment of the first aspect, the polymeric wall comprises a barrier material comprising one or more of nylon or polyethylene.

In an embodiment of the first aspect, the polymeric wall comprises a barrier material comprised of nylon/polyethylene.

In an embodiment of the first aspect, the polymeric wall comprises a barrier material comprising of nylon/polyvinylidene chloride/polyethylene.

In an embodiment of the first aspect, the outer container is selected from the group consisting of a push-fit capsule, a wrap, and a band, and wherein the outer container comprises a material selected from the group consisting of gelatin, cellulose, and collagen.

In an embodiment of the first aspect, the septum is cone-shaped.

In an embodiment of the first aspect, the inflation source container is configured to connect to the inflation catheter via a connector or an inflation valve.

In an embodiment of the first aspect, the inflation catheter is from 1 French to 6 French in diameter, and is from about 50 cm to about 60 cm in length.

In an embodiment of the first aspect, the inflation catheter is a dual lumen catheter comprising an inflation lumen and a detachment lumen, wherein the inflation lumen is in fluid connection to the inflation source container, and wherein the detachment lumen is configured for connection to a detachment liquid source container, wherein the detachment liquid comprises a physiological compatible liquid, and wherein the interference fit is insufficient to maintain a seal upon application of a hydraulic pressure by the detachment liquid, such that upon application of the hydraulic pressure to the needle assembly it is ejected from the balloon valve.

In an embodiment of the first aspect, the inflation catheter comprises a single lumen and a structural member providing increased tensile strength, and an inflation valve configured for connecting the single lumen to the inflation source container and a detachment liquid source container, wherein the detachment liquid comprises a physiological compatible liquid, and wherein the interference fit is insufficient to maintain a seal upon application of a hydraulic pressure by the detachment liquid, such that upon application of the hydraulic pressure to the needle assembly it is ejected from the balloon valve.

In an embodiment of the first aspect, the inner cylinder is configured to control alignment of the needle assembly with the septum, provide a barrier to the needle piercing the polymeric wall, and provide compression such that the septum reseals after inflation and needle withdrawal.

In an embodiment of the first aspect, a plurality of intragastric balloons is connected to a single inflation catheter.

In an embodiment of the first aspect, the inflation catheter is of a uniform stiffness.

In an embodiment of the first aspect, the inflation catheter is of a variable stiffness.

In an embodiment of the first aspect, the inflation source comprises a syringe.

In an embodiment of the first aspect, the inflation source is configured to utilize information regarding inflation pressure as a function of time to provide feedback to a user, wherein the feedback indicates a condition selected from the group consisting of failure by mechanical blockage, failure by esophagus constraint, failure by inflation catheter leak or detachment, and successful balloon inflation.

In a second aspect, a method is provided for inflating an intragastric balloon, the method comprising: providing an intragastric balloon in an outer container, the intragastric balloon comprising a polymeric wall, wherein the polymeric wall comprises one or more layers, and a balloon valve system comprising a self-sealing septum in a retaining structure, wherein the retaining structure comprises a concentric valve system with a smaller inner cylinder housing the septum and a larger outer cylinder housing a material configured to provide compressive forces against a bell-shaped needle sleeve of an inflation catheter, wherein the material providing compressive forces is a higher durometer material than the septum, and wherein the smaller inner cylinder comprises a lip configured for an interference fit with the bell-shaped needle sleeve; providing an inflation catheter comprising a needle assembly, the needle assembly comprising a hollow needle, a bell-shaped needle sleeve; piercing the septum by the needle of an inflation catheter, whereby an interference fit is created between the bell-shaped needle sleeve and the lip of the smaller inner cylinder; causing the intragastric balloon in an outer container attached by the interference fit to the inflation catheter to be swallowed by a patient in need thereof; degrading the outer container so as to permit inflation of the intragastric balloon; inflating the intragastric balloon in the patient's stomach via the inflation catheter, wherein the inflation catheter is connected to an inflation fluid source container; and detaching the intragastric balloon from the inflation catheter, wherein a detachment liquid comprising a physiological compatible liquid is forced through the inflation catheter to apply hydraulic pressure to the needle assembly such that the interference fit between the lip and the bell-shaped needle sleeve is broken, the needle assembly is ejected from the balloon valve and the self-sealing septum reseals.

In an embodiment of the second aspect, the inflation catheter is a dual lumen catheter comprising an inflation lumen and a detachment lumen, wherein the inflation lumen is configured for fluid connection to the inflation source container, and wherein the detachment lumen is configured for connection to a detachment liquid source container for detachment of the balloon.

In an embodiment of the second aspect, the inflation catheter is a single lumen catheter comprising a structural member providing increased tensile strength and an inflation valve configured for first connecting the single lumen catheter to the inflation source container and then to a detachment liquid source container for detachment of the balloon.

In an embodiment of the second aspect, wherein the method further comprises monitoring inflation pressure as a function of time and detaching when a predetermined ending pressure is obtained, wherein successful balloon inflation is indicated by achievement of the preselected ending pressure, which is based on a starting pressure in the inflation source and an inflation volume of the balloon.

In a third aspect, a method is provided for deflating an intragastric balloon, the method comprising: providing an intragastric balloon in an in vivo intragastric environment, the intragastric balloon comprising a polymeric wall and a valve system, the valve system comprising a self-sealing valve, a casing, an outer sealing member, a rigid retaining structure, and a deflation component; wherein the casing has one or more vent pathways and a lip configured to hold the outer sealing member in place, wherein the outer sealing member is positioned to block the one or more vent pathways when in place, wherein the rigid retaining structure provides support to the septum and the outer sealing member, and wherein the deflation component is situated in the casing and behind the retaining structure; exposing the deflation component to moisture inside of the balloon via the one or more vent pathways, whereby the deflation component expands, pushing the retaining structure and thus the outer sealing member linearly past the lip of the casing to open the one or more vent pathways so as to provide fluid communication between the in vivo gastric environment and a lumen of the balloon; and deflating the balloon through the one or more vent pathways.

In an embodiment of the third aspect, the deflation component comprises a solute material encapsulated in a binder material, wherein the deflation component is further surrounded by moisture limiting material that has a predefined moisture vapor transmission rate.

In an embodiment of the third aspect, the solute material is a polyacrylamide.

In an embodiment of the third aspect, the rigid retaining structure and the casing has a press fit lock that prevents the rigid retaining structure from being expelled from the casing after maximum displacement by the deflation component.

In a fourth aspect, a method is provided for deflating an intragastric balloon, the method comprising: providing an intragastric balloon in an in vivo intragastric environment, the intragastric balloon comprising a polymeric wall, a self-sealing valve system, and a deflation system, the deflation system comprising a casing, a sealing member, a plunger, and a deflation component; wherein the casing has one or more vent pathways and is secured in the polymeric wall, wherein the plunger provides support to the sealing member and maintains the sealing member in position to block the one or more vent pathways in the casing when in place, and wherein the deflation component is situated in the casing and behind the plunger; exposing the deflation component to moisture inside of the balloon via the one or more vent pathways, whereby the deflation component expands, pushing the plunger and thus the sealing member linearly through the casing to open the one or more vent pathways so as to provide fluid communication between the in vivo gastric environment and a lumen of the balloon; and deflating the balloon through the one or more vent pathways.

In an embodiment of the fourth aspect, the intragastric balloon further comprises a water retaining material situated between the deflation component and the one or more vent pathways, wherein the water retaining material is configured to retain water and to hold it against a surface of the deflation component in order to maintain a constant moisture environment.

BRIEF DESCRIPTION OF THE DRAWINGS

FIG. 8A depicts the valve 800 prior to coupling with the inflation catheter 820, and FIG. 8B depicts the valve 800 coupled to inflation catheter 820, wherein the catheter 820 is a dual-lumen catheter having a D-shaped first lumen 821 and a D-shaped second lumen 822.

FIG. 11A depicts a cross-sectional view of the single lumen catheter 1110, which includes a tensile cord 1120, a needle 1130 and a connector 1140, and a bell-shaped needle sleeve 840 protecting the needle 1130. FIG. 11B is an enlarged perspective cross-sectional view of the single lumen catheter 1110 of FIG. 11A showing detail of the needle 1130, the bell-shaped needle sleeve 840, and the tensile cord 1120. FIG. 11C is a perspective cross-sectional view of the single lumen catheter 1110 of FIG. 11B coupled with and seated in the self-sealing valve system 100 of FIG. 1D showing additional detail of the needle 1130 extending through the septum 114 and the stop ring 116.

FIG. 36 depicts the valve 1906 of the dispenser 3500 in the 'closed' position.

FIG. 37 depicts a luer lock plug 1907 configured to cover the end of the gauge of the dispenser 3500 and the valve 1906 in the 'open' position.

FIG. 40 is an enlarged view of the disposable Nitrogen Fill System 3510 of FIG. 35.

FIG. 41 depicts the dispenser 3500 with the lever 1903 in the 'open' position and valve 1906 in the 'closed' position in advance of receiving the disposable Nitrogen Fill System 1600.

FIG. 44 depicts catheter markings 4410 employed in conjunction with placement of the Obalon Gastric Balloon Assembly (not depicted).

FIG. 45A depicts a first step in connecting the catheter 1110 to the dispenser (not depicted) via the three way valve 700, which includes a male luer port having first and second portions 4520a and 4520b, respectively.

FIG. 45B depicts a second step of connecting the catheter 1110 to the dispenser (not shown) wherein the male luer port is connected with the catheter 1110.

FIG. 48 is an enlarged view of the stopcock 1912 of FIG. 47 showing greater detail of the connection between the syringe 1913 and the stopcock 1912.

FIG. 59A is an enlarged front perspective view of the female member 5300 of the engagement subassembly 5200 of FIG. 52.

FIG. 59B is an enlarged top view of the female member 5300 of FIG. 59A.

FIG. 59C is an enlarged front view of the female member 5300 of FIG. 59A.

FIG. 59D is an enlarged rear view of the female member 5300 of FIG. 59A.

FIG. 59E is an enlarged cross-sectional view of the female member 5300 of FIG. 59A, the cross-section being taken along line 59E-59E of FIG. 59B.

FIG. 60A is an enlarged front perspective view of the male member 5400 of the engagement subassembly 5200 of FIG. 52.

FIG. 60B is a rear perspective view of the male member 5400 of FIG. 60A.

FIG. 60C is an enlarged top view of the male member 5400 of FIG. 60A.

FIG. 60D is an enlarged front view of the male member 5400 of FIG. 60A.

FIG. 60E is an enlarged rear view of the male member 5400 of FIG. 60A.

FIG. 60F is an enlarged cross-sectional view of the male member 5400 of FIG. 60A, the cross-section being taken along line 60F-60F of FIG. 60D.

DETAILED DESCRIPTION OF THE PREFERRED EMBODIMENT

Figure 1B:
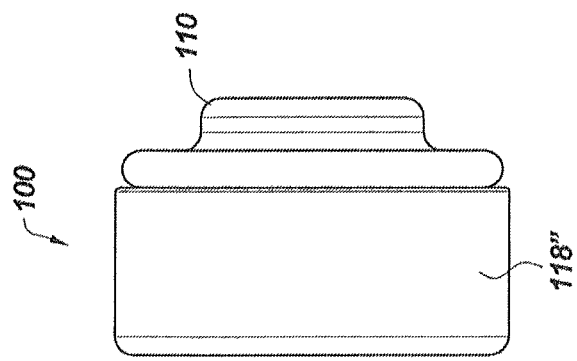
FIG. 1B is a side view of the valve system 100 of FIG. 1A
Figure 1A:
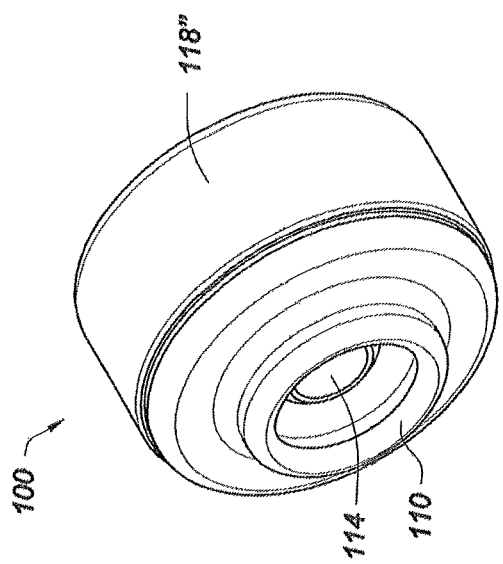
FIG. 1A is a perspective view of a concentric valve housing, self-sealing valve system or head assembly 100 of one embodiment, the valve system 100 including a polymeric inner cylinder 110 concentrically assembled together with a septum 114 and a concentric metallic retaining structure 118.
Figure 1D:
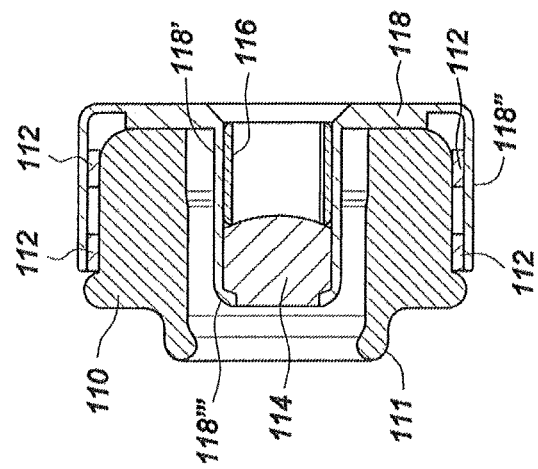
FIG. 1D is a cross-sectional view of the valve system 100 of FIG. 1A wherein the cross-section is taken along line 1D-1D of FIG. 1C, and wherein the concentric metallic retaining portion structure 118 includes an inner metallic cylinder 118' housing the septum 114 a slightly larger outer metallic cylinder 118'' housing the polymeric inner cylinder 110 and a lip 118'''. Retaining rings 112 secure the inner cylinder 110 with the outer metallic cylinder 118'' and a stop ring 116 secures the septum 114 within the inner metallic cylinder 118'. The polymeric inner cylinder 110 includes a lip 111 that is configured for an interference fit with a bell-shaped needle sleeve (not shown), such as is described elsewhere herein.
Figure 1C:
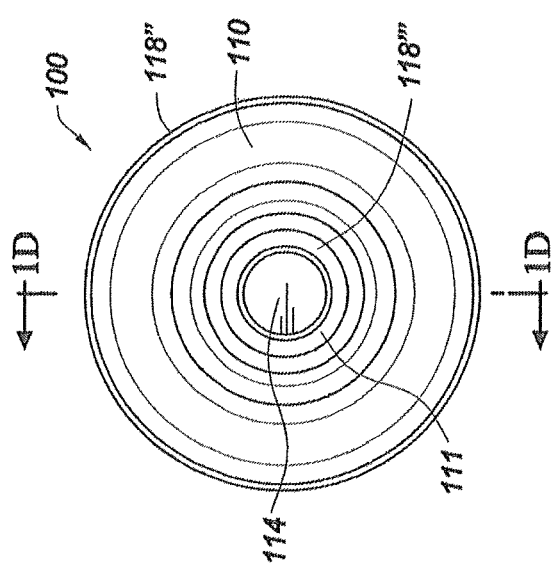
FIG. 1C is a top view of the valve system 100 of FIG. 1A.
Figure 2B:
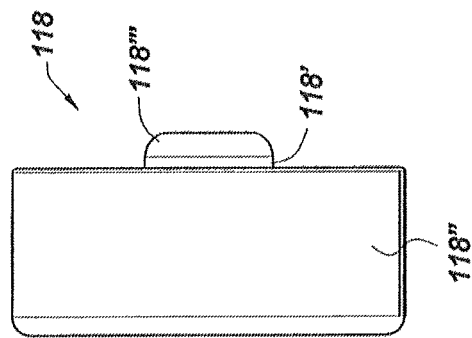
FIG. 2A-D depict a perspective view (FIG. 2A), a side view (FIG. 2B), a cross-sectional view (FIG. 2C), and a top view (FIG. 2C) of the concentric metallic retaining structure 118 of the self-sealing valve system 100 of FIGS. 1A-D. The retaining structure 118 includes the inner metallic cylinder 118' into which the septum 114 can be inserted or otherwise fabricated therein and the lip or rim 118'''.
Figure 2A:
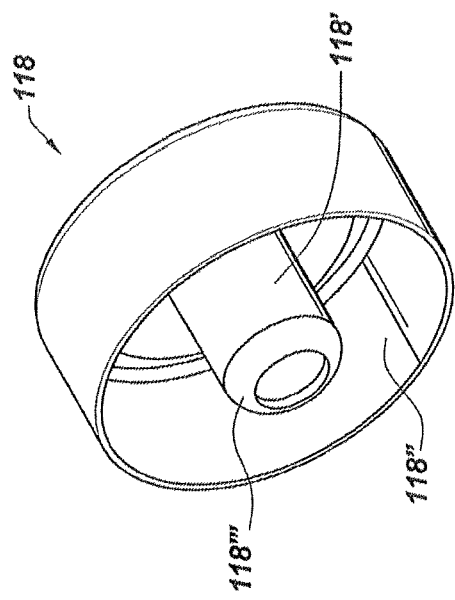
Figure 2C:
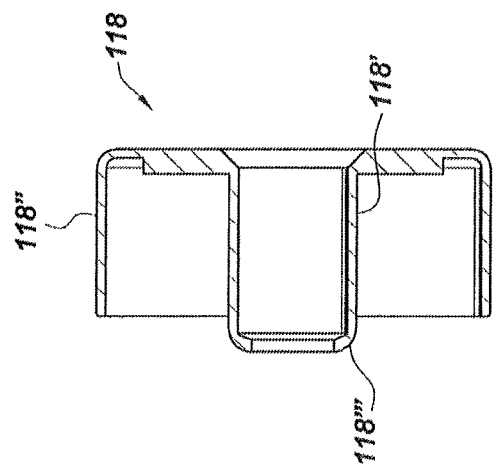
Figure 2D:
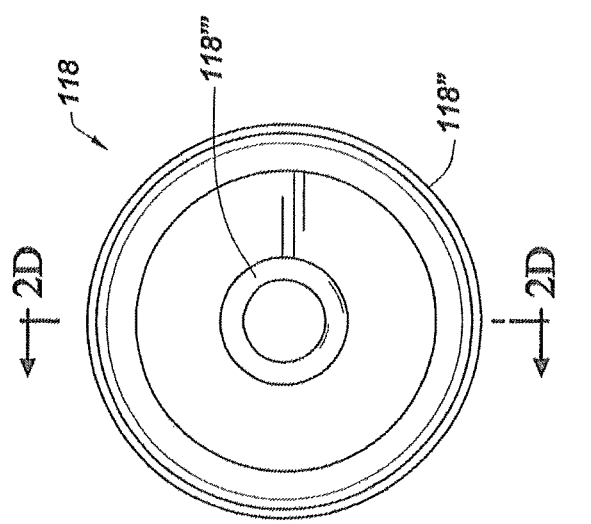

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The term "degradable" as used herein is a broad term, and is to be given its ordinary and customary meaning to a person of ordinary skill in the art (and is not to be limited to a special or customized meaning), and refers without limitation to a process by which structural integrity of the balloon is compromised (e.g., by chemical, mechanical, or other means (e.g., light, radiation, heat, etc.) such that deflation occurs. The degradation process can include erosion, dissolution, separation, digestion, disintegration, delamination, comminution, and other such processes.

The term "swallowable" as used herein is a broad term, and is to be given its ordinary and customary meaning to a person of ordinary skill in the art (and is not to be limited to a special or customized meaning), and refers without limitation to ingestion of a balloon by a patient such that the outer capsule and its constituents are delivered to the stomach via normal peristalsis movement. While the systems of preferred embodiments are swallowable, they are also configured for ingestion by methods other than swallowing. The swallowability of the system is derived, at least in part, by the outer container size for the self-inflating system and the catheter and outer container size for the manual inflation system. For the self-inflating system, the outer capsule is sufficient to contain the inner container and its constituents, an amount of activation agent injected prior to administration, the balloon size and the balloon material thickness. The system is preferably of a size less than the average normal esophagus diameter.

Described herein is an orally ingestible device. In preferred embodiments, the device is able to traverse the alimentary canal. The device may be useful, for example, as an intragastric volume-occupying device. The device overcomes one or more of the above-described problems and shortcomings found in current intragastric volume-occupying devices.

In order to more clearly describe the subject matter of the preferred embodiments, different embodiments of the same subcomponent will be described under a single relevantly-titled subheading. This organization is not intended to limit the manner in which embodiments of different subcomponents may be combined in accordance with the present invention.

Swallowable Intragastric Balloon System

A swallowable, self-inflating or inflatable intragastric balloon system according to selected preferred embodiments includes the following components: a balloon in a deflated and compacted state ("balloon or volume occupying component") with a self-sealing valve system for addition of fluid to the lumen of the balloon or to the inner container ("valve system") and an outer capsule, container, or coating ("outer container") that contains the balloon. In a self-inflating configuration, an inner capsule or other container ("inner container") that contains one or more $CO_2$ generating components is present inside the lumen of the balloon. In the self-inflating balloon configuration, the valve is preferably attached to the inner surface of the balloon by an adhesive or other means (e.g., welding), and provided with an inoculation spacer to prevent puncture of the wall of the balloon and inner container by a needle or other means for injecting an liquid activation agent into the lumen of the balloon via the self-sealing valve. In an inflatable configuration, the balloon includes an inflation assembly, including an inflation fluid source, a catheter and tubing, for inflating the balloon after ingestion or placement in the stomach. A valve providing releasable attachment of the tubing to the balloon is provided in the inflatable balloon configuration. Preferably, the self-sealing valve system attached to the balloon (e.g., on its inside surface) in the inflatable configuration is "universal" or compatible with a swallowable catheter or a physician-assisted catheter. The valve system serves to allow for balloon inflation using a miniature catheter that includes a needle assembly and also provides a mechanism for detachment of the catheter after inflation has been completed.

The outer container preferably incorporates the balloon in a compacted state (e.g., folded and rolled). In the self-inflating configuration, the folded balloon preferably includes sufficient space to allow for activation liquid to be injected into the balloon, wherein the liquid activation agent initiates separation, erosion, degradation, and/or dissolution of the inner container and generation of $CO_2$ upon contact with the inflation agent contained within the inner container, which subsequently causes outer container separation, erosion, degradation, and/or dissolution due to $CO_2$ gas pressure. In the inflatable balloon configuration, the outer container need only incorporate the balloon in a compacted state.

Selected components of a swallowable intragastric balloon system of a preferred embodiment can include a silicone head with radioopacity ring, trimmed 30 D silicone septum, Nylon 6 inoculation spacer, compacted balloon, inner container (if self-inflating), and outer container as constituents of the system in unassembled form. A fully assembled outer container can include a vent hole aligned with a septum for puncture to inject liquid activation agent (if self-inflating) or a port for connection of tubing (if inflatable). As discussed further below, the components of particularly preferred systems possess the attributes described herein; however, in certain embodiments systems can be employed which utilize components having other attributes and/or values.

Devices according to the preferred embodiments are intended for ingestion by a patient and deployment without the need to resort to invasive methods. It is therefore desirable that the device of the preferred embodiments be operable to conform to a compact delivery state which can be swallowed by a patient with minimal discomfort. Once in the stomach, it is desirable for the device to assume a substantially larger deployed state. In order to achieve the transition from a delivery state to a deployed state the device is subjected to inflation.

In order to treat obesity or assist individuals with their weight loss goals, various embodiments of the intragastric devices described herein are preferably delivered to a patient's stomach and maintained in the patient's stomach in an inflated state, preferably for at least thirty days. In some embodiments, the inflated intragastric devices are maintained in a patient's stomach for a treatment duration of one to three months, and in some embodiments, the devices are maintained in a patient's stomach up to six months or more. A plurality of intragastric devices may be delivered to a patient's stomach during a treatment duration. For example, in some embodiments, up to two or three or more inflated intragastric devices (of the same size or of two or more different sizes) may be present in a patient's stomach at a point in time. At the end of treatment, the devices may be removed endoscopically. In other embodiments, the devices may deflate and pass through the lower gastrointestinal tract. In order to maintain a proper degree of inflation and reduce discomfort and/or side effects for a patient, the patient may be prescribed one or more prescription drugs to take regularly while the inflated intragastric device is in the patient's stomach. For example, in some embodiments, a proton pump inhibitor, an antiemetic, and/or a spasmolytic agent may be prescribed.

Inner Container

In order to initiate inflation in the self-inflating configuration, the inflation subcomponent may require outside inputs such as an activation agent. The activation agent is preferably injected using a syringe having a needle with a gauge diameter of from 25 to 32. The needle length is preferably from about 0.25 inches (0.6 cm) to 1 inches (2.54 cm) in length so as to create a flow rate that allows for delivery of the full volume of inflation agent within 30 seconds, but in a manner/stream/flow that does not physically damage the inner container, thereby causing premature $CO_2$ generation and inflation. The activation agent is preferably pure water, or a solution containing up to 50% concentration of anhydrous citric acid at 20° C., or the equivalent thereof at varying solution temperatures based on solubility of anhydrous citric acid. Preferably, the system is configured to have an occupyable void space in the central lumen of the balloon when in compacted form in the outer container of from about 0.3 ml to about 4.5 ml, such that a corresponding volume of activation agent can be injected into the void space.

In one embodiment, prior to folding, the free-floating inner container with inflation agent for $CO_2$ generation is preferably vertically aligned with the self-sealing valve system such that the septum/inoculation spacer is placed directly above the tip of the capsule. The balloon contains an inner container. A self-sealing valve system is adhesively adhered to the interior of the wall of the balloon, and the inverted configuration of the balloon is provided by inversion through a hole sealed with a patch. The top approximate ¼ of the balloon wall is folded over the inner capsule, and the pleats where the capsule is are creased similar to the pleats formed in the second step of making a paper airplane, then folded over to the left or to the right. The bottom approximate ¾ of the sphere is then accordioned using no more than 2 creases and folded over the capsule. The left half is then folded over the right half of the capsule or vice versa so that the wings touch. Then the material is rolled over until it creates a tight roll. The device is then placed inside the outer container.

In a self-inflating configuration, the balloon is folded so as to form a pocket around the inner capsule, to insure that the liquid injected through the self-sealing valve system is contained in an area less than 10% of the entire balloon surface area. It is not necessary to provide a pocket in the inflatable configuration, as no inner capsule is provided. The balloon is folded such that the number of total folds is minimized so as to minimize possible damage to the outer material or compromise of barrier properties. The number of total folds is preferably less than 10 folds. The balloon material is rolled when at all possible such that the number of creases required to fit the balloon in an outer container is minimized. This is done in effort to also to prevent lumen material damage. The self-sealing valve is also preferably constructed off-center of the balloon so as to minimize the number of folds that layer on top of each other.

In the self-inflating configuration, the material forming the wall of the balloon is processed and folded to maximize reaction efficiency by localizing the initiation agent injected into the balloon so that it is maintained proximal to the reactants within the inner container. The balloon is folded such that once the reaction initiates and the outer container separates, the balloon unfolds in a manner that creates the largest possible surface area, which prohibits the balloon from readily passing through the pyloric sphincter. The ratio of reactants in the inflation agent and activation agent are selected such that the pH of any remnant liquid inside the lumen of the balloon is acidic, with a pH of less than 6, such that any balloon leakage or breach that allows stomach acid to enter does not cause additional $CO_2$ generation and resulting unintentional re-inflation.

In a self-inflating configuration, an inflation agent is compressed, formed or otherwise held in a shape which provides good surface area availability for the reactants for $CO_2$ generation, while minimizing the space and/or volume sufficient to hold the inner container. Preferably, the inner container has a length (longest dimension) of from about 0.748 inches (1.9 cm) to 1.06 inches (2.7 cm) and a diameter or width of from about 0.239 inches (0.6 cm) to about 0.376 inches (1 cm). The volume of the inner container is preferably from about 0.41 ml to about 1.37 ml. The inner container is preferably in the form of a standard push-fit gelatin capsule but a gelatin tape may be used in lieu of a push-fit capsule. The container is preferably relied upon for containing the inflation agent; however, additional sealing or other encapsulation can be employed to control timing of inflation. Gelatin is particularly preferred for use as the inner container; however other materials can also be suitable for use, e.g., cellulose. In order to minimize the internal volume of the system, it is generally preferred to include only a single inner container; however, in certain embodiments two or more internal containers can advantageously be employed. Timing of self-inflation is selected based on a normal esophageal transit time and a normal time of gastric emptying of large food particles, such that the balloon does not inflate to a size that can block the esophageal passageway or prematurely pass through the pyloric sphincter. Timing is also controlled by compacting the balloon such that the activation agent is substantially localized in the balloon next to the inner capsule, creating an efficient $CO_2$ self-inflation method. Balloon inflation is initiated by the liquid activation agent causing degradation of the inner container, such that the inflation agent in the inner container contacts the liquid activation agent, thereby initiating the gas generation reaction.

Inflation Assembley

In certain preferred embodiments, the volume-occupying subcomponent is filled with a fluid using tubing which is subsequently detached and pulled away from the volume-occupying subcomponent. One end of the volume-occupying subcomponent has a port connected to tubing of sufficient length that when unwound can span the entire length of the esophagus, from mouth to stomach. This tubing is connected to the volume-occupying subcomponent with a self-sealable valve or septum that can tear away from the volume-occupying subcomponent and self-seal once the volume-occupying subcomponent is inflated. A physician or other health care professional secures one end of the tubing as the patient swallows the device. Once the device is residing within the stomach, the physician uses the tube to transmit a fluid, such as air, nitrogen, other gas(es), saline solution, pure water, or the like, into the volume-occupying subcomponent and thereby inflate it. After the volume-occupying subcomponent is fully inflated, the tubing is released and can be pulled out from inside the patient.

The tube may be released in a number of manners. For example, the tubing may be detached by applying a gentle force, or tug, on the tubing. Alternatively, the tubing may be detached by actuating a remote release, such as a magnetic or electronic release. Additionally, the tubing may be released from the volume-occupying subcomponent by an automatic ejection mechanism. Such an ejection mechanism may be actuated by the internal pressure of the inflated volume-occupying subcomponent. For example, the ejection mechanism may be sensitive to a specific pressure beyond which it will open so as to release any excess pressure and simultaneously release the tube. This embodiment provides a desirable feature through combining release of the tubing with a safety valve that serves to avert accidental over inflation of the volume-occupying subcomponent in the patient's stomach.

This automatic release embodiment also provides the benefit that the device inflation step may be more closely monitored and controlled. Current technology allows for a self-inflating intragastric volume-occupying subcomponent which generally begins to inflate in a four minute timeframe after injection with an activation agent such as citric acid. In this approach, the volume-occupying subcomponent may, in some instances, begin to inflate prior to residing within the stomach (e.g., in the esophagus), or, in patients with gastric dumping syndrome or rapid gastric emptying, the volume-occupying subcomponent may end up in the small intestine prior to the time that inflation occurs. Accordingly, in certain embodiments it can be desirable to inflate the volume-occupying subcomponent on command, once it is ascertained that the volume-occupying subcomponent is residing in the correct location.

In certain embodiments, it may also be advantageous for the volume-occupying subcomponent to inflate gradually or in several steps over time. For example, if gas escapes the volume-occupying subcomponent prior to the desired deflation time, it can be beneficial for the device to re-inflate in order to preserve it in its expanded state.

Outer Container

The balloon is preferably provided in a deflated and folded state in a capsule or other retaining, containing or coating structure ("outer container"). The outer container is preferably in the form of a standard push-fit gelatin capsule, with the push-fit relied upon for containing the deflated/folded balloon; however, a gelatin wrap can advantageously be employed in certain embodiments. Gelatin is particularly preferred for use as the outer container; however other materials can also be suitable for use, e.g., cellulose, collagen, and the like. Preferably, the outer container has a length (longest dimension) of from about 0.95 inches (2.4 cm) to 2.5 inches (6.3 cm) and a diameter or width of from about 0.35 inches (0.9 cm) to about 0.9 inches (2.4 cm). The volume of the inner container for the self-inflatable version is preferably from about 1.2 ml to about 8.25 ml. In the self-inflating configuration, the outer container is preferably configured with one or more holes, slits, passageways or other egresses, preferably on each end, which can act as vents such that any gas created due to inflation agent exposure to condensation or other ambient moisture present during processing does not cause premature separation or degradation of the inner container prior to 30 seconds after inoculation of the liquid activation agent, which may have an undesirable effect on reaction efficiency. Such egresses can also expedite dissolution of the outer container to prepare the balloon for inflation in the inflatable configuration. The process of the outer capsule degrading (e.g., separates, dissolves, or otherwise opens) is expedited by pressure build up caused by inflation (self-inflation or inflation via catheter) of the balloon. The outer capsule can be dipped in water for a brief time to soften the materials but not release the balloon prior to swallowing to minimize the time lapse between swallowing and balloon inflation. In the inflatable configuration, the outer container is provided with a hole to house the inflation tube needle assembly, wherein the diameter of the catheter needle housing is mechanically compatible with the diameter of the outer container hole such that the needle can be inserted into the self-sealing valve while maintaining therein the housed balloon to facilitate pushing or swallowing of the balloon assembly. In a preferred embodiment, the outer container is a capsule. The distal half of the capsule may be flared to prevent abrasion of the balloon materials by the leading edge of the capsule as the compacted balloon is inserted into the capsule. The capsule can also comprise two parts held together with a gel band and encompassing the folded balloon that allows for quicker separation of the capsule so that inflation can take place more expeditiously. The outer capsule degrades (e.g., separates, dissolves, or otherwise opens) due to contact with ingested fluid ingestion (e.g., water intake) and preferably degrades within 5 minutes or less, more preferably within 2 minutes or less, so as not to cause discomfort to the patient while the balloon/catheter tube is in place.

In a preferred embodiment, the device is fitted into a standard sized gelatin capsule. The capsule may be formed of a material that has a known rate of degradation such that the device will not be released from the capsule or otherwise deployed prior to entry into the stomach. For example, the capsule materials may include one or more polysaccharide and/or one or more polyhydric alcohols.

Alternatively, the device, in its delivery state, may be coated in a substance that confines the device in its delivery state while also facilitating swallowing. The coating may be applied by a dipping, sputtering, vapor deposition, or spraying process which may be conducted at an ambient or positive pressure. The balloon may also be encapsulated by wrapping gelatin tape around the balloon and then placing the wrapped balloon in a capsule, if so desired.

In certain preferred embodiments, the encapsulated or coated device is lubricated or otherwise treated so as to facilitate swallowing. For example, the encapsulated or coated device may be wetted, heated, or cooled, prior to swallowing by the patient. Alternatively, the encapsulated or coated device may be dipped in a viscous substance that will serve to lubricate the device's passage through the esophagus. Examples of possible coatings can be any substances with lubricious and/or hydrophilic properties and include glycerin, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments the coating or capsule is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the capsule may be weighted at a certain end in order for it to be oriented appropriately when it is administered, as it travels down the esophagus, and/or when it is in the stomach. The weighting components may include polymer materials or inflation reactants.

The swallowable, self-inflating intragastric balloon is provided with mechanisms to reliably control timing of self-inflation such that premature inflation while in the esophagus during swallowing is avoided and sufficient inflation once in the stomach so as to prevent passage through the pyloric sphincter is ensured. Normal esophageal transit time for large food particles has been documented as 4-8 seconds, and gastric emptying of large food particles through the pylorus does not occur for at least 15-20 minutes. The outer container is preferably configured to separate, dissolve, degrade, erode, and/or otherwise allow the deflated/folded balloon to begin unfolding not less than 60 seconds but not more than 15 minutes after inoculation with liquid activation agent. The inner container is preferably configured chemically, mechanically or a combination thereof to retard the initial $CO_2$ generating chemical reaction such that sufficient $CO_2$ to begin inflating the balloon is not available earlier than 30 seconds after inoculation with the liquid activation agent, but to permit generation of sufficient $CO_2$ such that at least 10% of the occupyable volume of the balloon is filled within 30 minutes, at least 60% of the occupyable volume of the balloon is filled within 12 hours, and at least 90% of the occupyable volume of the balloon is filled within 24 hours. This timing allows for injection of the activation agent into the outer container by the medical professional, passing the device to the patient, and swallowing by normal peristaltic means by the patient. This timing also prohibits potential passing of an uninflated balloon into the duodenum by the balloon being inflated to a sufficient size such that gastric emptying of the balloon cannot be easy, as objects more than 7 mm in diameter do not readily pass.

Balloon Delivery Components

Figure 49A:
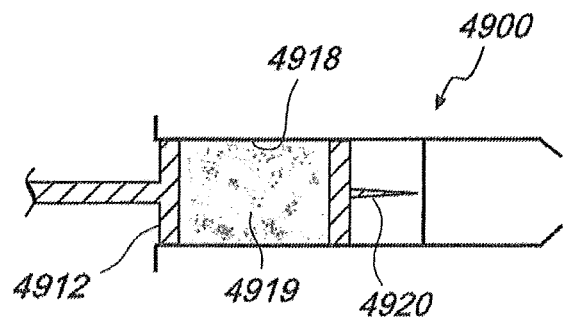
FIG. 49A-C depicts cross-sectional views of a delivery subcomponent 4900, in accordance with a preferred embodiment.
Figure 49B:
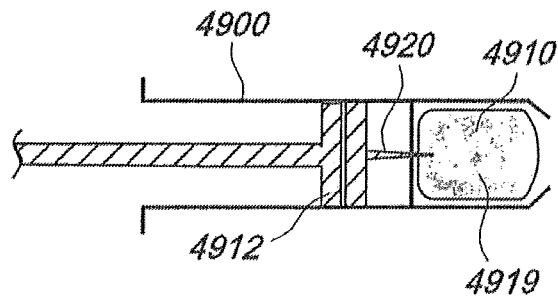
Figure 49C:
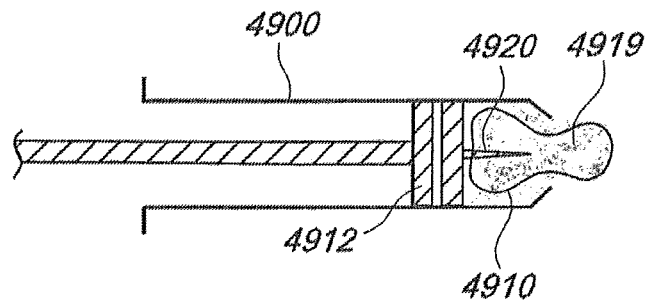

In certain embodiments, it may advantageous for an administrator of the device to use a delivery tool 4900 (see FIGS. 49A-C) for delivering an intragastric device 4910 to the back of the patient's throat, such as past the epiglottis, or for facilitating passage through the esophagus 5120 in the optimal orientation. The delivery tool 4900 may enable the device administrator to inject the device 4910 with one or more inflation agents as the device 4910 is being administered to the patient. In a preferred embodiment, such injection may be accomplished in the same mechanical action(s) of the administrator that are employed to release the device 4910 from the delivery tool 4900 into the mouth or esophagus. For example, with reference to FIG. 49A, the delivery tool 4900 may include a plunger 4912, a reservoir 4918 having a fluid or liquid 4919, and an injection needle 4920. As shown in FIGS. 49B and C, the administrator pushes the plunger 4912 which (either in sequence or approximately simultaneously) forces the injection needle 4920 into the device 4910 and thereby injects the liquid 4919 contained in reservoir 4918 into the device 4910. Subsequent application of force to the plunger 4912 pushes the device 4910 out of the delivery tool 4900 and into the desired location within the patient. Furthermore, the delivery tool 4900 may also include a subcomponent that administers an anesthetic or lubricant into the patient's mouth or esophagus to ease the swallowability of the device 4910.

It may be advantageous for the administrator of the device 4910 to have a structure for retrieving (not shown) the device if it were to get stuck in the patient's esophagus following administration. Accordingly, certain embodiments of the device 4910 in its delivery state may include a string (not shown) with one end attached to the device 4910 and with the other end able to be held by the administrator. The string may be attached to the device 4910 firmly enough to allow the administrator to exert enough force on the string to pull the device 4910 from the patient's esophagus if it is lodged therein. The string would be long enough to allow the device 4910 to reach the patient's stomach while still having the other end held by the administrator. The string may be attached to the device 4910 in such a manner that it detaches within minutes after the device 4910 is in the stomach. For example, the string may be attached to the device 4910 by means of a water or stomach acid soluble adhesive.

When swallowing a gastric balloon assembly 3000, the patient's epiglottis 5130 (see FIGS. 51A and 51B) generally folds backward and downward, to block the entrance to the larynx and thereby ensure that the assembly 3000 passes down the esophagus 5120 instead of the larynx 5115 and trachea 5110. As noted elsewhere herein, the gastric balloon assembly 3000 includes an encapsulated balloon 810 releasably engaged with a miniature inflation catheter 1110. The encapsulated balloon, which includes a capsule or outer container, may be up to about 6.3 cm long and up to about 2.4 cm in diameter. Due to this large size, some patients have extreme difficulty swallowing the assembly 3000 on their own. In particular, some patients have difficulty with gagging and even vomiting when swallowing the assembly 3000.

Figure 50:
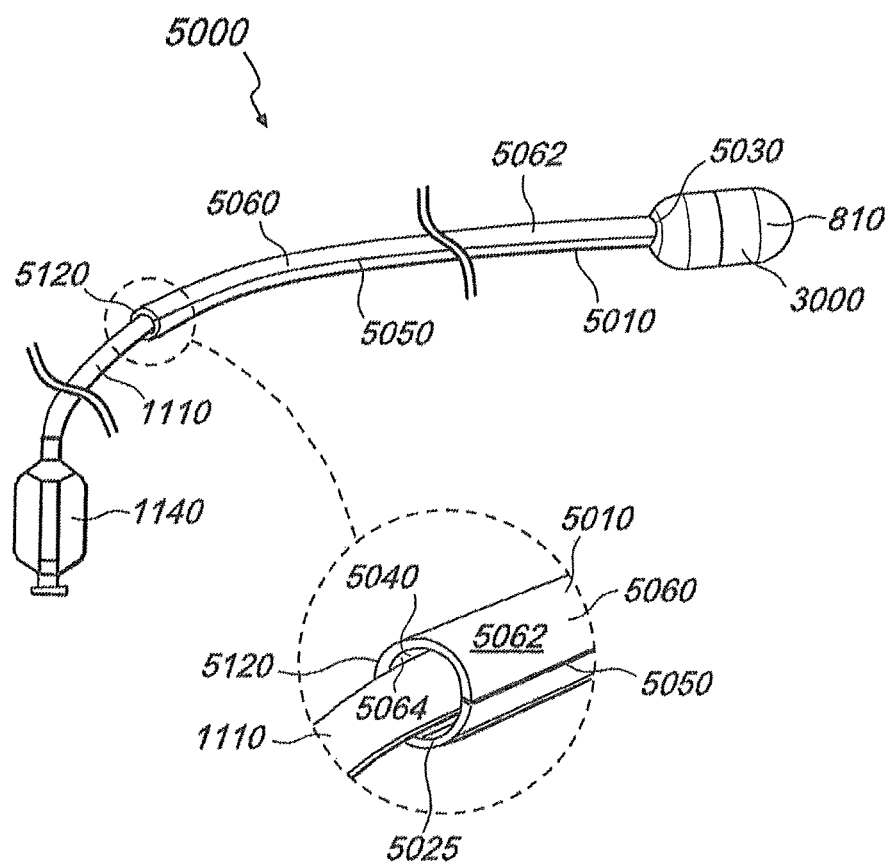
FIG. 50 depicts an embodiment of a rapid exchange push assist catheter 5000, in one embodiment.
Figure 51A:
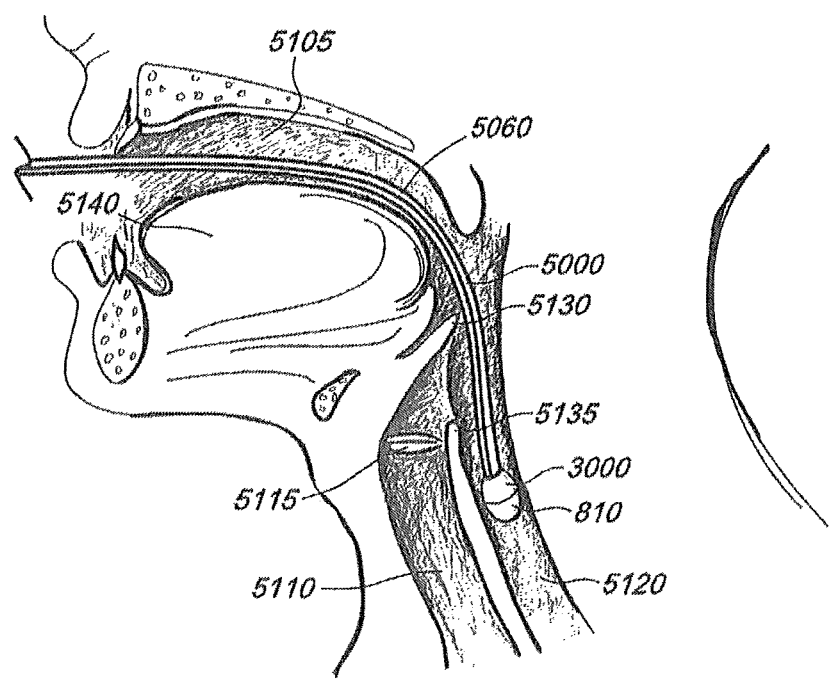
FIG. 51A is a schematic illustrating placement of a capsule 810 into a patient's esophagus 5120 using a rapid exchange push assist catheter 5000 in one embodiment, wherein the number 5105 denotes the mouth or oral cavity, 5110 denotes the trachea, 5115 denotes the vocal cords, 5120 denotes the esophagus, 5130 denotes the epiglottis, 5135 denotes the corniculate cartilage and 5140 denotes the tongue.
Figure 51B:
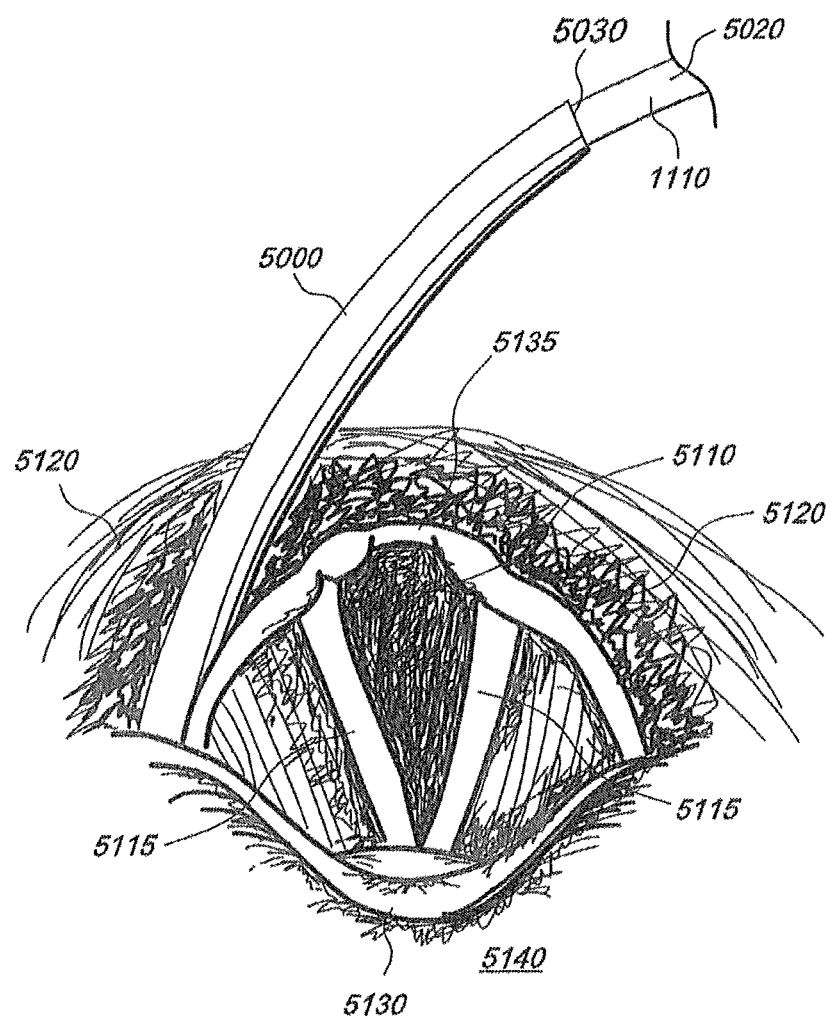
FIG. 51B is a schematic looking through a patient's mouth 5105 toward the esophagus 5120.
Figure 52:
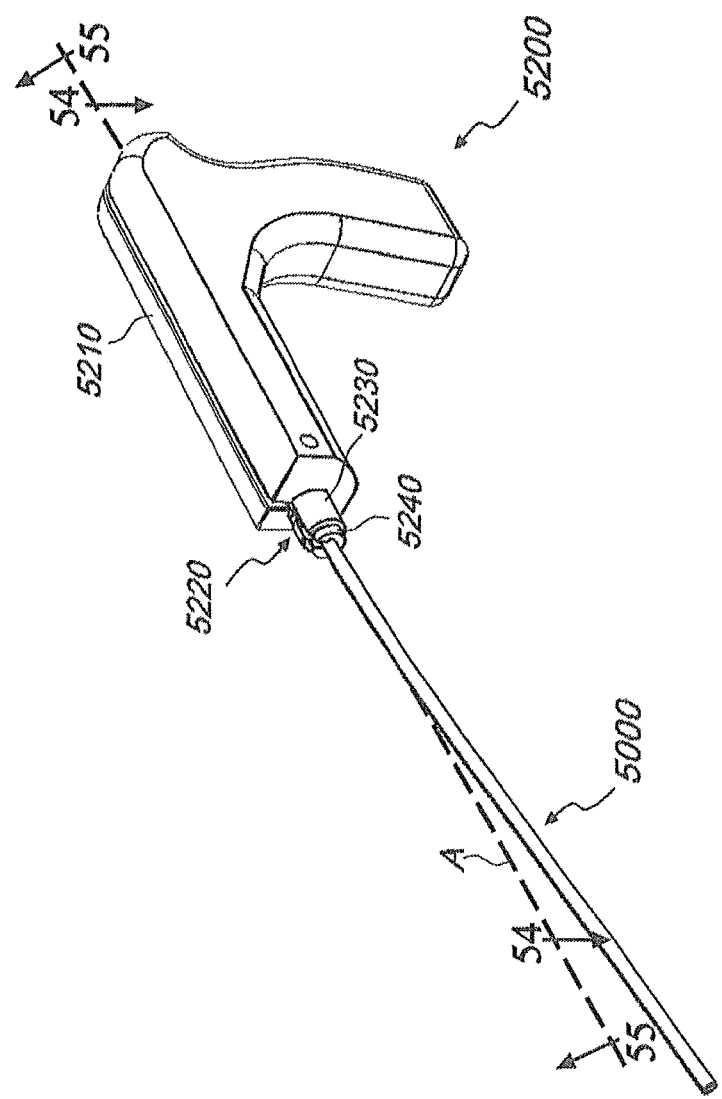
FIG. 52 is a perspective view of a rapid exchange push assist catheter system 5200 in an embodiment, the system 5200 including a push catheter 5000, a handle member 5210 and an engagement subassembly 5220, which includes a female component 5230 and a male component 5240.

To alleviate such gagging and vomiting, the administrator may help such patients swallow the assembly 3000 by spraying the back of the patient's esophagus 5120 with a numbing agent, such as is commonly used when a laryngoscopy or nasal endoscopy is performed, and then placing the capsule in the patient's throat, past the epiglottis 5135 using a rapid exchange push assist catheter 5000 delivery tool, an example of which is shown in FIGS. 50 through 51B and described below. It is noted that it could be dangerous for the patient to swallow the assembly 3000 without such assistance by the administrator, because numbing the throat may disrupt normal swallowing, thereby causing the swallowed assembly 3000 to pass into the trachea 5110 instead of the esophagus 5120 and choking the patient. Placing the assembly 3000 past the epiglottis 5130 with a swallow assist device such as the push assist catheter 5000 can minimize such risk of choking when the throat is numbed.

As depicted in FIG. 50, the rapid exchange push assist catheter 5000 includes an elongate catheter body 5010 extending from a first orifice 5020 defined by a first end surface or edge 5025 to a second orifice or opening 5030 defined by a second end surface or edge (not shown). The body 5010 includes a length to extend at least from outside the patient's mouth, through the mouth 5105 and into the esophagus 5120 and past at least the corniculate cartilage 5135 (see FIGS. 51A-B). In some embodiments, the body 5010 includes a length of at least 8 inches (20.3 cm). In some embodiments, the length of the body 5010 is between 9 inches (22.9 cm) or less and 14 inches (35.6 cm) or more, between 10 inches (25.4 cm) and 13 inches (33.0 cm), or between 11 inches (28.0 cm) and 12 inches (30.5 cm). In some embodiments, the length of the body 5010 is about 8 inches (20.3 cm), about 9 inches (22.9 cm), about 10 inches (25.4 cm), about 11 inches (28.0 cm), about 12 inches (30.5 cm), about 13 inches (33.0 cm), about 14 inches (35.6 cm), about 15 inches (38.0 cm) or longer. In some embodiments, the body 5010 is 8 inches (20.3 cm), 9 inches (22.9 cm), 10 inches (25.4 cm), 11 inches (28.0 cm), 12 inches (30.5 cm), 13 inches (33.0 cm), 14 inches (35.6 cm) or 15 inches (38.0 cm) long or more. In still other embodiments, the body 5010 includes a length sufficient to reach at least from outside the patient's mouth and into the patient's stomach (not shown).

A channel or through-bore 5040 extends through the catheter body 5010 so as to join the first and second openings or openings 5020 and 5030, respectively. The through-bore 5040 includes a diameter (e.g., an inner diameter) at least slightly greater than the outer diameter of an inflation catheter 1110 for use therewith. However, the through-bore diameter may be sufficiently large to receive a catheter connector 1140 therethrough. An elongate cut or slit 5050 extends the length of the body 5010 so as to join the first and second openings 5020 and 5030. Further, the slit 5050 extends through the body wall 5060 so as to join the wall outer surface 5062 with the wall inner surface 5064.

In some embodiments, the first end or first end surface 5025 includes a grasping structure or handle for holding the catheter 5000 and enabling the administrator to more deftly guide the second end 5030 and capsule 810 through the patient's mouth and to the back of the throat. Suitable grasping structures may include various grips and handles.

In some embodiments, the push assist catheter 5000 includes a threading device (not shown) for threading the inflation catheter 1110 of the gastric balloon assembly 3000 through the slit 5050 and into the through-bore 5040. The threading device widens or opens the slit 5050 an opening 5020 or 5030 and then slides along the length of the catheter body 5060, thereby moving the opened portion of the slit 5050. The inflation catheter 1110 is aligned along the slit 5050 and then threaded through or engaged with the threading device (not shown). The threading device is then moved along the body 5060, simultaneously opening the slit 5050 and pushing the inflation catheter 1110 through the slit opening and into the through-bore 5040.

When the inflation catheter 1110 is fully assembled into the through-bore 5040, the inflation catheter 1110 is gently or slightly pulled backwardly through the through-bore 5040, thereby tensioning the assembly 3000 against the second opening 5030. In some embodiments, the second opening includes a reversible attachment device (not shown), for releasably attaching the capsule 810 to the second opening 5030, such as by an interference fit. In some embodiments, the catheter 5000 further includes a mechanical attachment and release mechanism (not shown) that can secure the capsule 810 to the catheter body 5010 until activation of the release mechanism when the capsule 810 is positioned in the patient's esophagus 5120, such as described below. The inflation catheter 1110 extends from the second opening 5030, through the through-bore 5040 and out of the first opening 5020.

The rapid exchange push assist catheter body 5010 is formed of one or more polymers and is flexible, so as to allow for maneuvering through the oral cavity 5105 and throat, but also characterized by high column strength so as to prevent column buckling from occurring upon application of force. In some embodiments, the body 5010 is formed of two different durometer polymers, wherein a harder durometer polymer forms the majority of the body 5010 and a lower durometer polymer is incorporated into the body 5010 on each side of the slit 5050, thereby creating a rubber zone in the body wall 5060 extending the length of the slit 5050. In preferred embodiments, the rubbery edges of the slit 5050 are compressed against one another or overlap, so as to prevent the slit 5050 from opening during catheter use while also making it easier to pull the inflation catheter 1110 rapidly out of the catheter body 5060. The catheter body 5010 is also biocompatible and capable of withstanding body temperature. In some embodiments, the body outer surface 5062 includes an anesthetic or lubricant to facilitate insertion into the patient's throat. As part of the procedure, the patient can also swallow water or other suitable liquid so as to distend esophageal tissue for smooth passage down of the device.

The catheter body 5010 can have a diameter of between less than 2 French (0.67 mm) and greater than 20 French (6.67mm). In some embodiments, the diameter of the catheter body 5010 is between 2 French (0.67 mm) and 5 French (1.67 mm), between 5 French (1.67 mm) and 8 French (2.67), between 8 French (2.67 mm) and 11 French (3.67 mm), between 11 French (3.67 mm) and 14 French (4.67mm), between 14 French (4.67mm) and 17 French (5.67 mm), or between 17 French (5.67 mm) and 20 French (6.67 mm). The catheter body 5010 is of a sufficient length to push the balloon capsule 810 at least partially down the patient's throat. The inflation catheter 1110 extends into and through the through-bore 5040 between the openings 5020 and 5030. The slit 5050 extends along the length of the catheter body 5010 and can facilitate insertion into and removal of the inflation catheter 1110 from the catheter body 5010. Although shown as a straight cylindrical tube in FIG. 50, the push assist catheter 5000 may be structured in any shape that facilitates insertion into the throat. For example, in some embodiments, the push assist catheter 5000 may be S-shaped or partially S-shaped.

Referring now to FIGS. 51A-B, to assist the patient in swallowing the assembly 3000, the administrator threads or zips the inflation catheter 1110 through the slit 5050 such that the inflation catheter 1110 extends through the through-bore 5040 and out the first opening 5020 (see FIG. 50) and then gently pulls backwardly on the inflation catheter 1110 such that the capsule 810 is attached to or held on to the catheter second opening 5030. The administrator grasps the catheter 5000 near the first opening 5020, the administrator eases the capsule 810 through the patient's oral cavity 5105, around or over the epiglottis 5130 and past the corniculate cartilage 5035, and into the esophagus 5120. Once the capsule 810 is located in a desired position in the patient's esophagus 5120, the inflation catheter 1110 is quickly removed from the push assist catheter 5000 by sliding the push assist catheter 5000 out of the patient's mouth 5105 and along a length of the inflation catheter 1110. Once the push assist catheter 5000 is removed from the patient's mouth 5110, the inflation catheter 1110 is removed from the through-bore 5040 by rapidly yet gently pulling the inflation catheter 1110 through the slit 5050 until the two catheters 5000 and 1110 are separated from one another. In some embodiments, the push assist catheter 5000 includes a disengagement mechanism or subassembly (not shown), which when actuated disengages the inflation catheter 1110 from the push assist catheter 5000. Once the push assist catheter 5000 is removed, the patient can proceed with swallowing the capsule 810 until it reaches his/her stomach 3210 in the usual way (see FIG. 32). In some embodiments, the catheter body 5010 does not include a slit, and the push assist catheter 5000 is removed by sliding the inflation catheter 1110 so that the inflation catheter 1110 exits out of the opening 5030.

Figure 32:
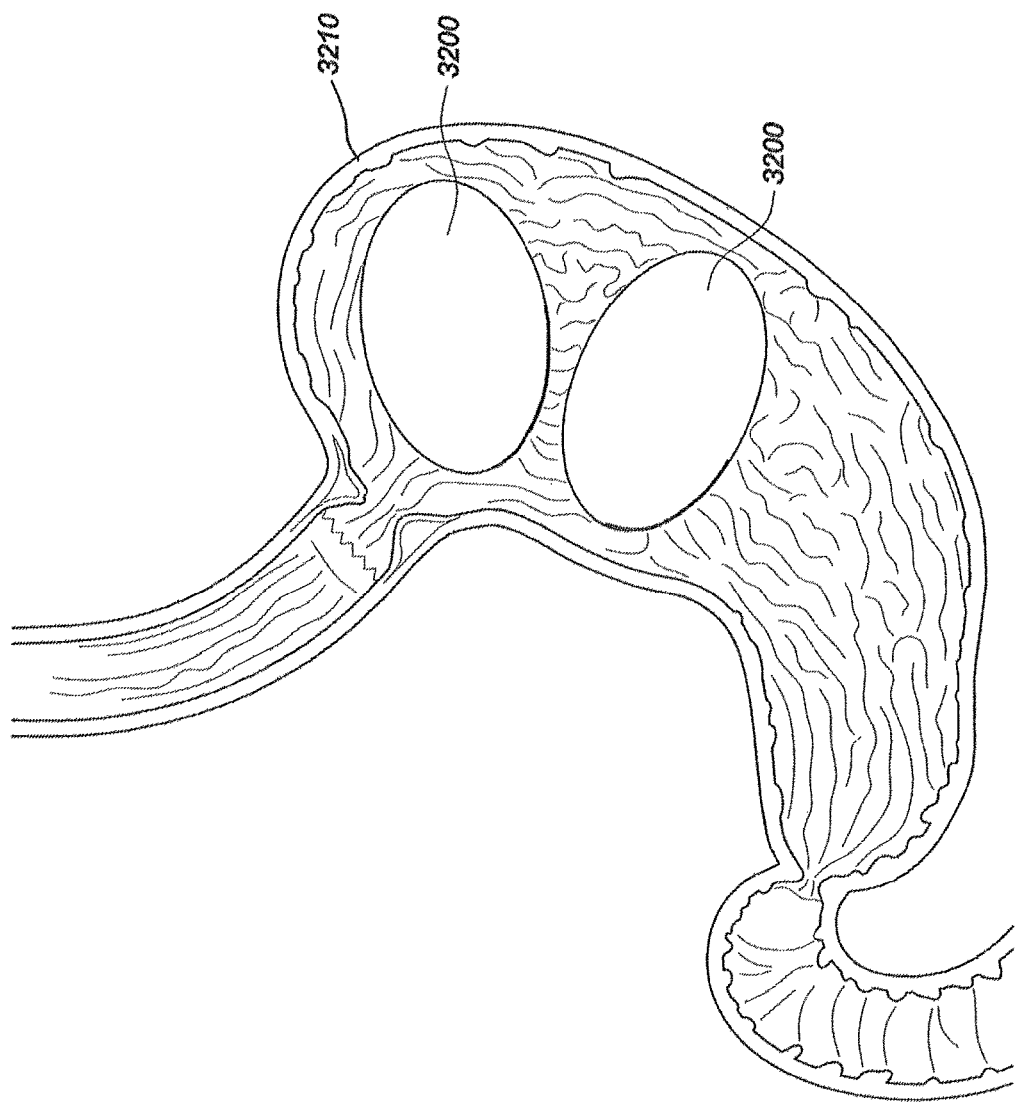
FIG. 32 depicts placement of two balloons 3200 in a patient's stomach 3210.

The rapid exchange push assist catheter 5000 can be configured to receive various types of inflation catheters 1110, including but not limited to single-lumen catheters, dual-lumen catheters, and miniature stiff-bodied inflation catheters, such as described elsewhere herein. The rapid exchange push assist catheter 5000 may also be configured for the placement of multiple balloons 3200, such as is shown in FIG. 32.

Referring now to FIGS. 52 through 62F, a rapid exchange push assist catheter system 5200 is provided in some embodiments to assist the patient in swallowing the assembly 3000. The rapid exchange push assist catheter system 5200 includes the rapid exchange push assist catheter 5000, a handle member 5210 and an engagement subassembly 5220, which includes a female portion 5230 and a male portion 5240. The system 5200 includes a longitudinal axis denoted by the letter A. The engagement subassembly 5200 is configured and arranged for threading the inflation catheter 1110 of the assembly 3000 into and engaging the rapid exchange push assist catheter 5000, which is described in greater detail below.

Figure 53:
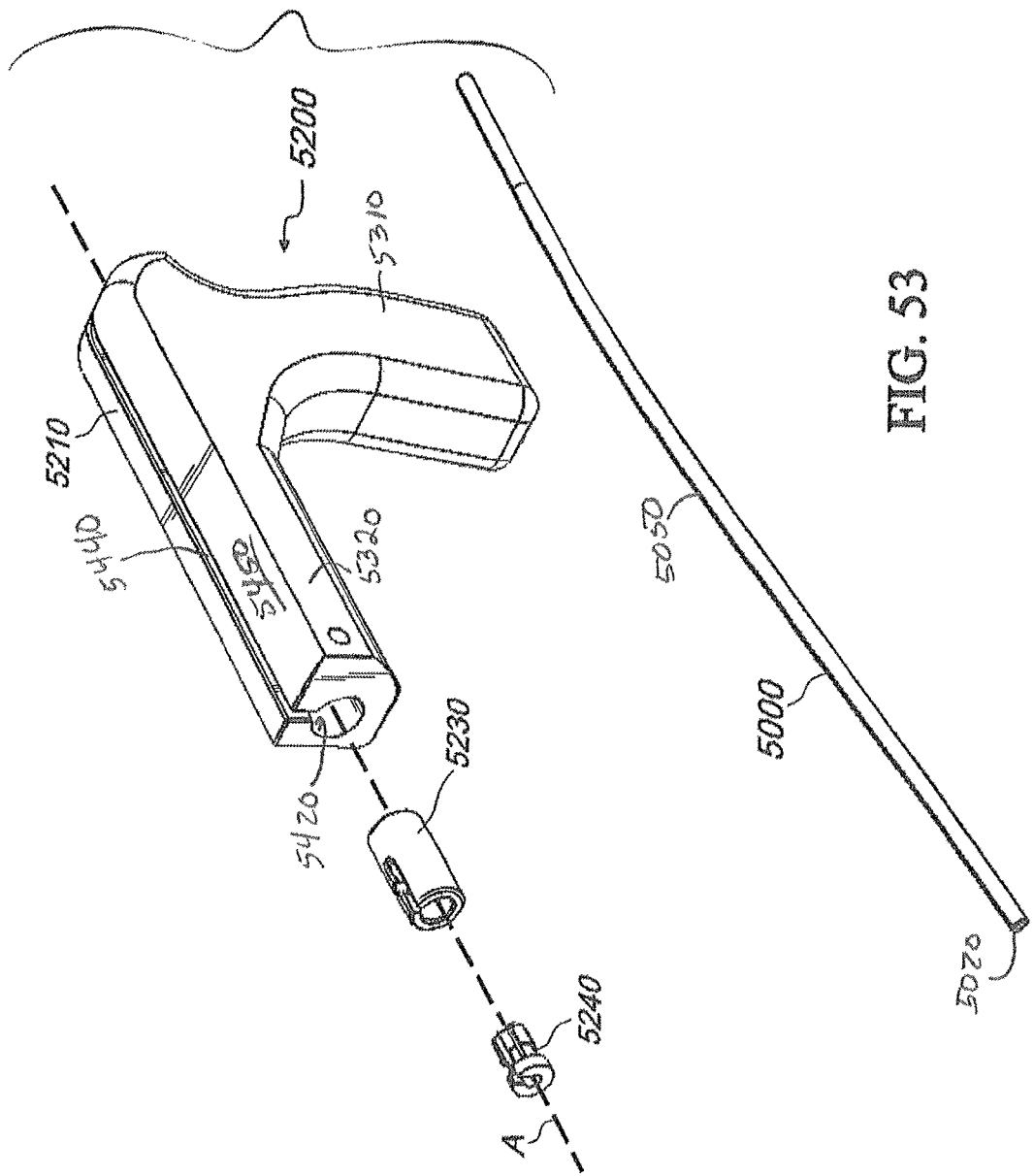
FIG. 53 is an exploded perspective view of the rapid exchange push assist catheter system 5200 of FIG. 52.
Figure 54:
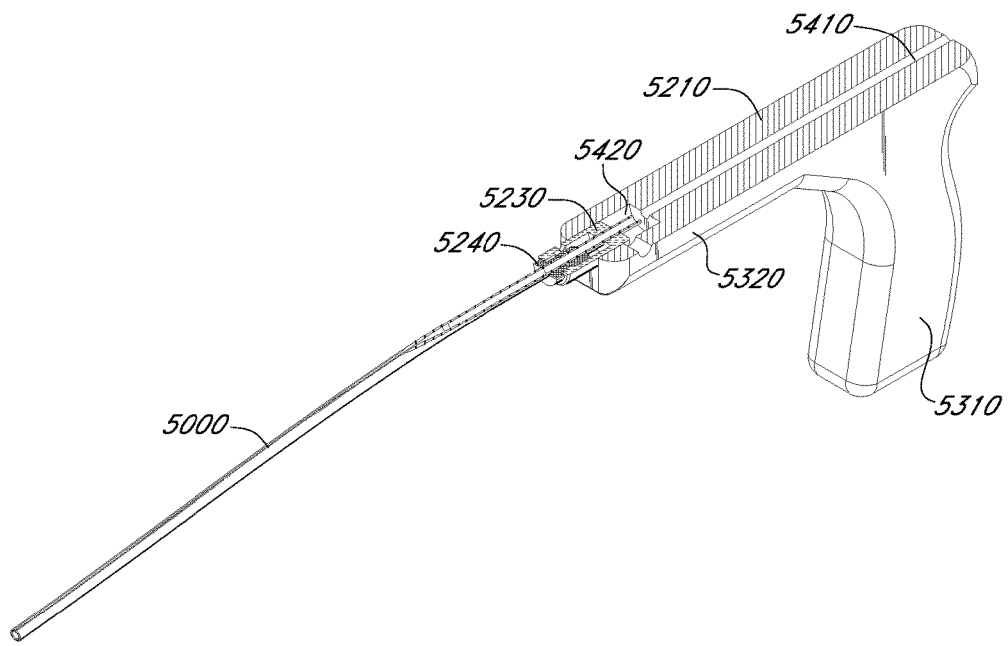
FIG. 54 is a cross-sectional view of the rapid exchange push assist catheter system 5200 of FIG. 52, wherein the cross-section is taken along line 54-54 of FIG. 52.
Figure 55:
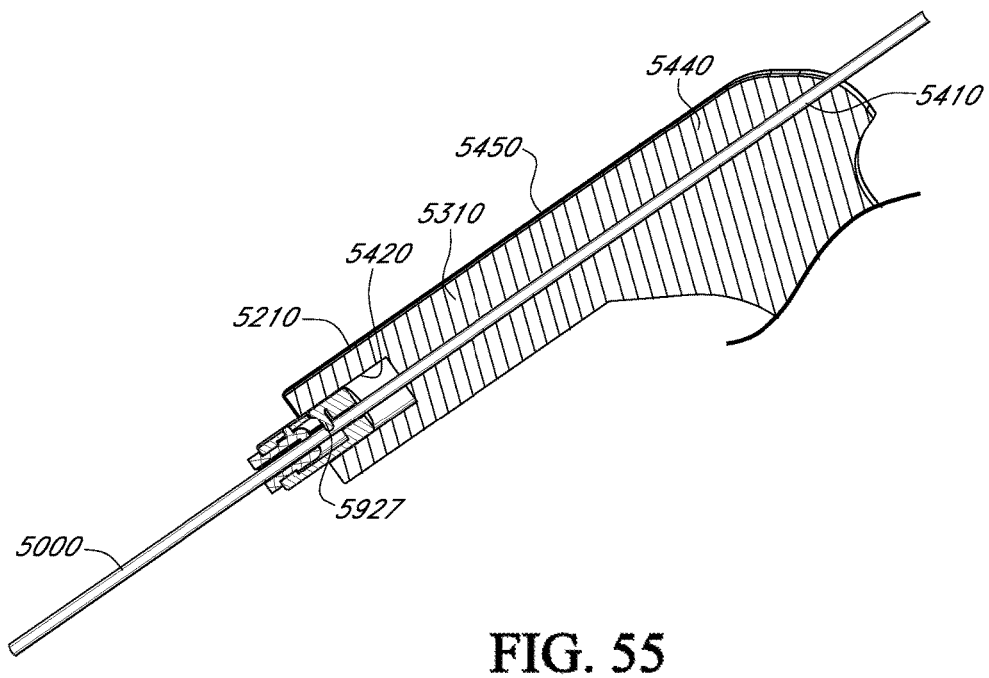
FIG. 55 is an enlarged cross-sectional view of the rapid exchange push assist catheter system 5200 of FIG. 52, with portions broken away, wherein the cross-section is taken along line 55-55 of FIG. 52.
Figure 56:
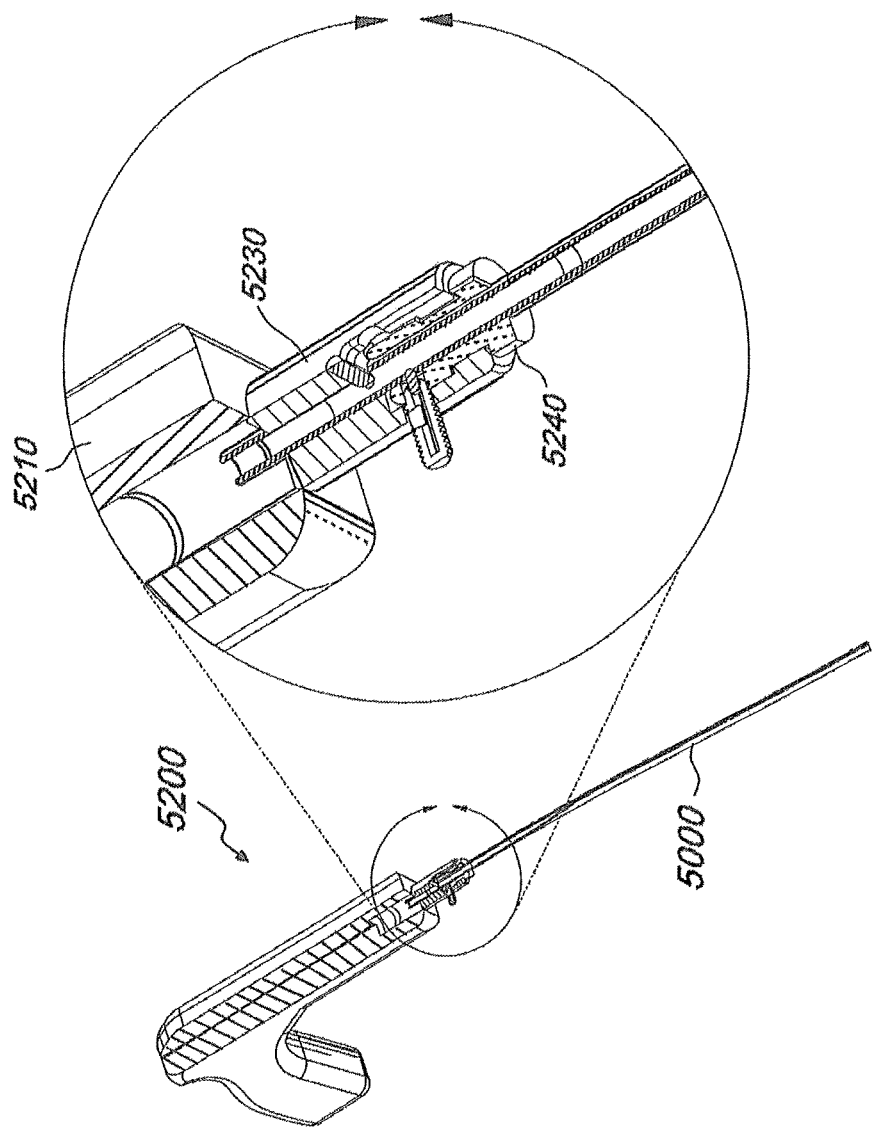
FIG. 56 is a quadrant-sectional view of the rapid exchange push assist catheter system 5200 of FIG. 52, with an enlarged view of the engagement subassembly 5200 in one embodiment.
Figure 57:
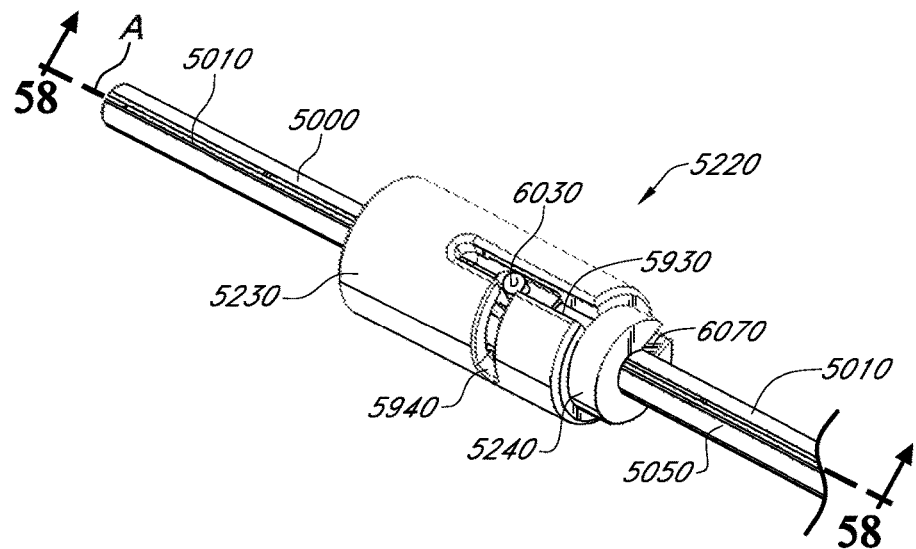
FIG. 57 is an enlarged perspective view of the engagement subassembly 5200 of FIG. 52 in a closed configuration and in engagement with the push catheter 5000.
Figure 58:
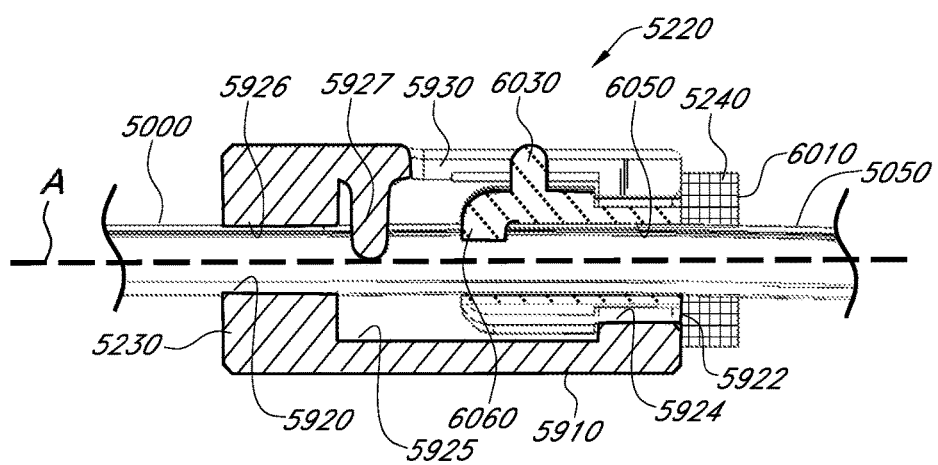
FIG. 58 is an enlarged cross-sectional view of the engagement subassembly 5200 and push catheter 5000 of FIG. 57, with the cross-section being taken along line 58-58 of FIG. 57.
Figure 61A:
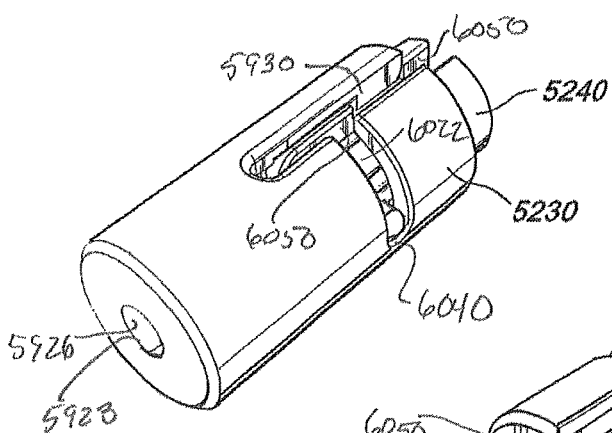
FIG. 61A is an enlarged rear perspective view of the engagement subassembly 5220 of FIG. 52, wherein the subassembly 5220 is in an opened configuration.
Figure 61B:
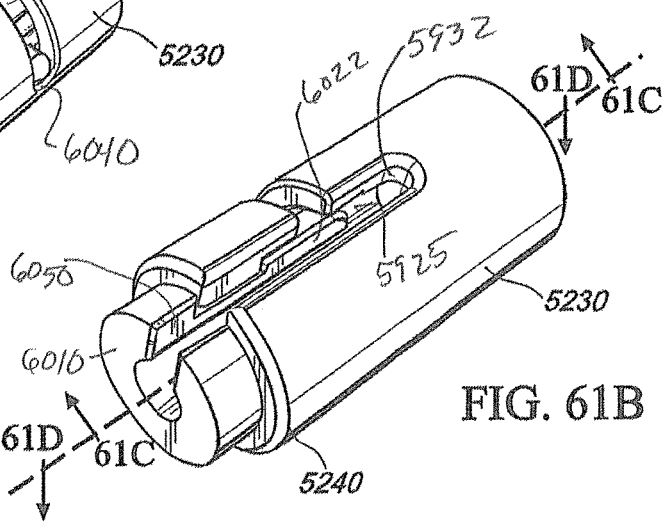
FIG. 61B is an enlarged front perspective view of the engagement subassembly 5220 of FIG. 61A.
Figure 61C:
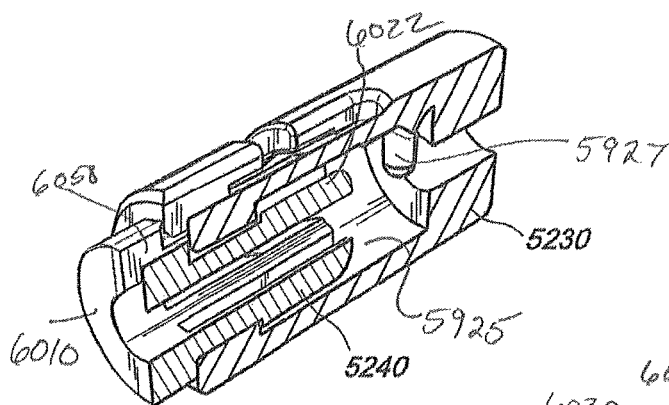
FIG. 61C is cross-sectional view of the engagement subassembly 5200 of FIG. 61B, with the cross-section being taken along line 61C-61C of FIG. 61B.
Figure 61D:
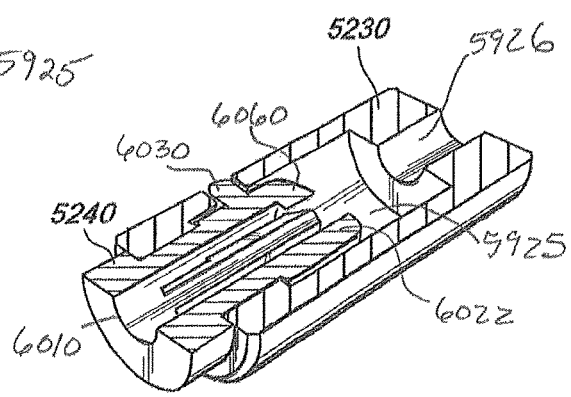
FIG. 61D is cross-sectional view of the engagement subassembly 5200 of FIG. 61B, with the cross-section being taken along line 61D-61D of FIG. 61B.
Figure 62A:
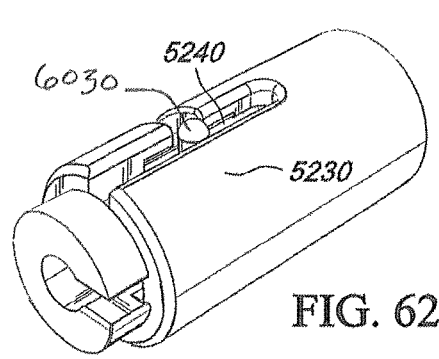
FIG. 62A is an enlarged front perspective view of the engagement subassembly 5220 of FIG. 52, wherein the subassembly 5220 is in the closed configuration.
Figure 62B:
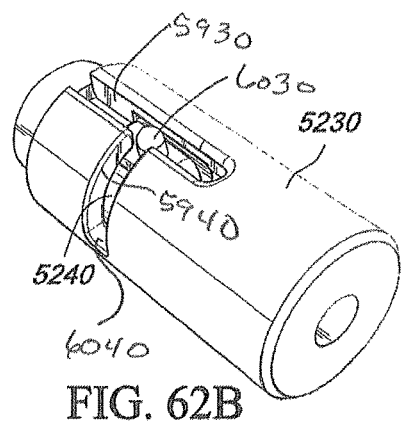
FIG. 62B is a rear perspective view of the engagement subassembly 5220 of FIG. 62A.
Figure 62C:
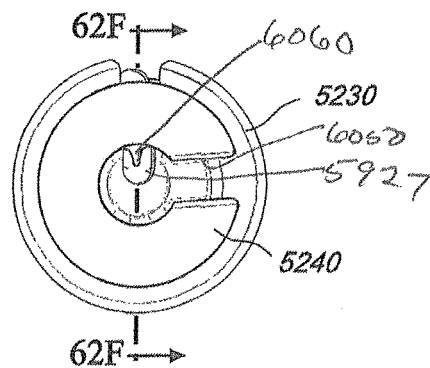
FIG. 62C is an enlarged front view of the engagement subassembly 5220 of FIG. 62A.
Figure 62D:
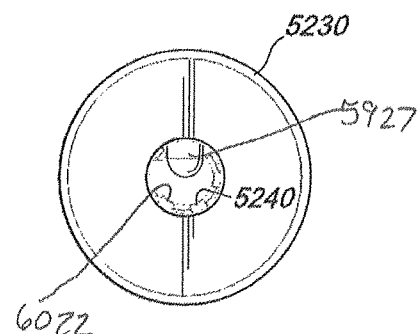
FIG. 62D is an enlarged rear view of the engagement subassembly 5220 of FIG. 62A.
Figure 62E:
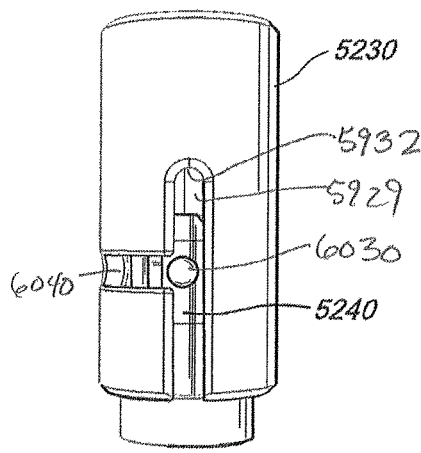
FIG. 62E is a top view of the engagement subassembly 5220 of FIG. 62A.
Figure 62F:
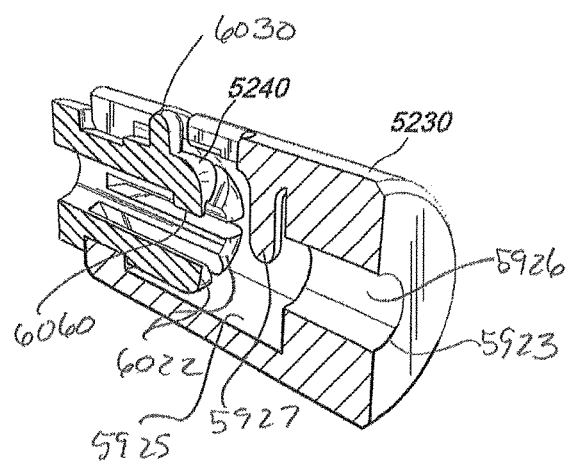
FIG. 62F is an enlarged cross-sectional view of the engagement subassembly 5220 of FIG. 62A, with the cross-section being taken along line 62F-62F of FIG. 62C.

As is seen most easily in FIGS. 53-55, the handle member 5210 includes a grip portion 5310 joined with an engagement portion 5320. The engagement portion 5320 includes a catheter receiving through-bore 5410 joined with an engagement chamber 5420, both of which are coaxial with axis A. The through-bore 5410 extends from a rear opening 5430 along axis A to the engagement chamber 5420 and is sized and shaped to receive the push catheter 5000 therethrough. The push catheter 5000 is inserted through the rear opening 5430 and pushed through the through-bore 5410 and into the engagement subassembly 5220, as described below. The engagement portion 5320 also includes a longitudinally extending access channel 5440 joining the upper surface 5450 of the engagement portion 5320 with the through-bore 5410 and the engagement chamber 5420, for inserting the inflation catheter 1110 into the through-bore 5410 and the engagement chamber 5420. The engagement chamber 5420 is sized and shaped to receive the engagement subassembly 5220 therein as is described in greater detail below.

As noted above, the engagement subassembly 5220 includes a female component 5230 and a male component 5340, which are most easily seen in FIGS. 57 through 62F. Referring now to FIGS. 59A through 59E, the female component 5320 includes a body 5910 sized and shaped to be rotatably received within the engagement chamber of engagement portion 5320. The body 5910 includes a longitudinally extending chamber 5920, a longitudinal guide structure 5930 joined with a perpendicular guide structure 5940. The chamber 5920 extends from the front and rear openings, 5922 and 5923, respectively, and includes coaxially aligned forward, middle and rear portions, which are denoted by the numerals 5924, 5925 and 5926 respectively, and a separating extension 5927 which extends inwardly from the rear end of the middle portion of the of the chamber 5920 of the female component 5230 toward the longitudinal axis A. As is most easily seen in FIG. 59E, the separating extension 5927 is located at the back end 5932 of the longitudinal guide structure 5930. When the push catheter 5000 is received into the through-bore 5410, it is pushed forwardly into the rear portion 5926 of the chamber 5920 and encounters the separating extension 5927. The first orifice 5020 of the push catheter 5000 may include an engagement notch (not shown) that engages the separating extension 5927 and guides the separating extension 5927 into the body slit 5050. Alternatively, the push catheter 5000 can be rotated in the through-bore 5410 of the handle member 5210 until the slit 5050 engages the separating extension 5927. As the push catheter 5000 is inserted through the chamber 5920, the separating extension 5927 progressively pushes the slit 5050 into an opened position for receiving the inflation catheter 1110 therein.

Referring now to FIGS. 60A through 60F, the male portion 5240 is structured so as to be received into and rotatably engages with the female portion 5230. In particular, the male portion 5240 includes a body 6005 with an external portion 6010 joined with an internal portion 6020. The external portion 6010 extends longitudinally out of the engagement subassembly 5220 so as to be actuatable or adjustable by the operator. The internal portion 6020 is sized and shaped to be rotatably received into and interlock with the forward and middle portions 5924, 5925 of the female portion 5230, such as is most easily seen in FIGS. 61C and 61D. For example, in the illustrated embodiment, the internal portion 6020 includes a plurality of beams 6022 that are contoured or otherwise sized and shaped to snap into and interlock with the chamber middle portion 5925.

The internal portion 6020 includes guide post 6030 that extends outwardly from one of the beams 6022 and that is sized and shaped to be sliding engaged with the perpendicular guide structure 5940 of the female component 5230, wherein, when the engagement portion 5220 is in an opened configuration (see FIGS. 61A-61D), the guide post 6030 is engaged with the rear wall 6040 of the perpendicular guide structure 5940, and when the engagement portion 5220 is in an closed configuration (see FIGS. 57, 58 and 62A-62F), the guide post 6030 is engaged with the longitudinal guide structure 5930. Accordingly, in this embodiment, the male portion 5240 can be rotated about the longitudinal axis A 90° with respect to female portion 5230.

The body 6005 of the male portion 5240 includes a longitudinally extending through-bore 6050 with a longitudinally running and inwardly extending zipper wedge 6060 and a longitudinally extending guide channel 6070. When the guide post 6030 is in the opened position, the longitudinal guide structure 5930 and the guide channel 6070 are vertically aligned with one another, and a first end of the inflation catheter 1110 can be inserted through both the longitudinal guide structure 5930 and the guide channel 6070 and into the push catheter through-bore 5040. In the illustrated embodiment, the capsule 810 is generally disposed at the front of the external portion 6010 of the male portion 5240, which may include a capsule engaging structure (not shown) and then the inflation catheter 1110 inserted through the aligned longitudinal guide structure 5930 and the guide channel 6070 and engaged in the push catheter through-bore 5040. After this step, the male portion 5240 is rotated to the closed position, wherein the guide post 6030 is engaged in the longitudinal guide longitudinal guide structure 5930, thereby locking the inflation catheter 1110 into the engagement subassembly 5220 and extending out of the handle engagement portion 5320, such as out of the rear opening 5430.

Once the engagement subassembly 5220 is in the closed position, the zipper wedge 6060 presses the inflation catheter 1110 into the through-bore 5040 of the rapid exchange push assist catheter 5000. The operator then gently pushes the push assist catheter 5000 through the rapid exchange push assist catheter system 5200, whereby the push assist catheter 5000 is engaged around the inflation catheter 1110. The operator can then remove the engaged push assist catheter 5000 and inflation catheter 1110, and insert the capsule 810 into the patient's esophagus 5120, such as described above. Alternatively, the operator can hold the rapid exchange push assist catheter system 5200 with the engaged inflation catheter 1110 and capsule 810 to place the capsule 810 in the patient's esophagus 5120. After the capsule is placed in the patient's esophagus 5120, the push assist catheter 5000 is removed, such as described above, and the patient swallows the capsule 810 and the inflation catheter 1110, such as described elsewhere herein. It is foreseen the rapid exchange push assist catheter system 5200 may include fewer, additional and/or alternative structures that can perform the same or similar functions.

Balloon

The volume-occupying subcomponent ("balloon") of the preferred embodiments is generally formed of a flexible material forming a wall which defines an exterior surface and an interior cavity. Various of the above-described subcomponents may be either incorporated into the wall or interior cavity of the volume-occupying subcomponent. As shown, volume-occupying subcomponent can vary in size and shape according to the patient's internal dimensions and the desired outcome. The volume-occupying subcomponent may be engineered to be semi-compliant, allowing the volume-occupying subcomponent to stretch or expand with increases in pressure and/or temperature. Alternatively, in some embodiments, a compliant wall offering little resistance to increases in volume may be desirable.

Spherical or ellipsoidal volume-occupying subcomponents are preferred in certain embodiments. Alternatively, the volume-occupying subcomponent may be constructed to be donut-shaped, with a hole in the middle of it, and may be weighted and shaped in such a way that it orients in the stomach to cover all or part of the pyloric sphincter, similar to a check valve. The hole in the middle of the volume-occupying subcomponent can then serve as the primary passage for the contents of the stomach to enter the small intestine, limiting the passage of food out of the stomach and inducing satiety by reducing gastric emptying. Volume-occupying subcomponent may be manufactured with different-sized donut-holes according to the degree that gastric emptying is desired to be reduced. Delivery, inflation and deflation of the volume-occupying subcomponent may be accomplished by any of the methods described above.

It is advantageous in certain embodiments for the volume-occupying subcomponent wall to be both high in strength and thin, so as to minimize the compacted volume of the device as it travels the esophagus of the patient. In certain embodiments, the volume-occupying subcomponent wall materials are manufactured with a biaxial orientation that imparts a high modulus value to the volume-occupying subcomponent.

In one embodiment, the volume-occupying subcomponent is constructed of a polymeric substance such as polyurethane, polyethylene terephthalate, polyethylene naphthalate, polyvinyl chloride (PVC), Nylon 6, Nylon 12, or polyether block amide (PEBA). The volume-occupying subcomponent may be coated with one or more layers of substances that modify (increase, reduce, or change over time) gas-barrier characteristics, such as a thermoplastic substance.

Preferably, the gas-barrier materials have a low permeability to carbon dioxide or other fluids that may be used to inflate the volume-occupying subcomponent. The barrier layers should have good adherence to the base material. Preferred barrier coating materials include biocompatible poly(hydroxyamino ethers), polyethylene naphthalate, polyvinylidene chloride (PVDC), saran, ethylene vinyl alcohol copolymers, polyvinyl acetate, silicon oxide (SiOx), acrylonitrile copolymers or copolymers of terephthalic acid and isophthalic acid with ethylene glycol and at least one diol. Alternative gas-barrier materials may include polyamine-polyepoxides. These materials are commonly acquired as a solvent or aqueous based thermosetting composition and are generally spray-coated onto a preform and then heat-cured to form the finished barrier coating. Alternative gas-barrier materials which may be applied as coatings to the volume-occupying subcomponent include metals such as silver or aluminum. Other materials that may be used to improve the gas impermeability of the volume-occupying subcomponent include, but are not limited to, gold or any noble metal, PET coated with saran, conformal coatings and the like, as listed, for example, in Tables 1a-b.

In certain preferred embodiments, the volume-occupying subcomponent is injection, blow or rotational molded. Either immediately following such molding, or after a period of curing, the gas-barrier coating may be applied if not already applied within the composite wall.

In another embodiment, the intragastric volume-occupying subcomponent is formed using a Mylar polyester film coating silver, aluminum or kelvalite as a metallicized surface, to improve the gas impermeability of the volume-occupying subcomponent.

In the event that the volume-occupying subcomponent's wall is composed of multiple layers of materials, it may be necessary to use certain substances or methods to connect, attach or hold together such multiple layers. Such substances can include a solvent or an ether-based adhesive. Such multiple layers may also be heat-bonded together. Once such layers are attached together to form (for example) a sheet of material to be made into a volume-occupying subcomponent, it may also be necessary to apply additional treatment steps to such material to allow it to seal together (for example, by application of a certain degree of heat and pressure) in order to be made into a volume-occupying subcomponent. Accordingly, it may be advantageous to include as an additional layer in the volume-occupying subcomponent certain materials that seal. For example, a volume-occupying subcomponent comprised of a combination of PET and SiOx layers, which impart favorable mechanical and gas impermeability characteristics to the volume-occupying subcomponent, may be sealed by including a layer of sealable polyethylene in such volume-occupying subcomponent.

According to another embodiment of the preferred embodiments, the functionality of the volume-occupying subcomponent and the deflation component is combined either in part or in whole. For example, the volume-occupying subcomponent may be formed of a substance that is degraded within the stomach over a desired period of time. Once the degradation process has formed a breach in the wall of the volume-occupying subcomponent, the volume-occupying subcomponent deflates, continues to degrade and passes through the remainder of the digestive tract.

Preferably, an automated process is employed that takes a fully constructed volume-occupying subcomponent, evacuates all of the air within the interior cavity and folds or compresses the volume-occupying subcomponent into the desired delivery state. For example, the evacuation of air from the volume-occupying subcomponent may be actuated by vacuum or mechanical pressure (e.g. rolling the volume-occupying subcomponent). In certain embodiments, it is desirable to minimize the number of creases produced in the volume-occupying subcomponent when in the delivery state.

In another embodiment, deflation of the volume-occupying subcomponent may be achieved through one or more injection sites within the wall of the volume-occupying subcomponent. For example, two self-sealing injection sites can be incorporated at opposite sides of the volume-occupying subcomponent. The volume-occupying subcomponent may be positioned within a fixture that employs two small-gauge needles to evacuate the air from the volume-occupying subcomponent.

In one embodiment, the self-sealing injection sites may further be used to insert chemical elements of the inflation subcomponent into the interior of the volume-occupying subcomponent. After injection of the chemical elements into the volume-occupying subcomponent, the same needles may be used to perform evacuation of the volume-occupying subcomponent.

It may be desirable that the volume-occupying subcomponent is packed into the delivery state under, for example, a negative vacuum pressure or under a positive external pressure.

The volume-occupying subcomponent wall materials may also be engineered to, once they are initially punctured or torn, tear relatively easily from the point of such puncture or tear. Such properties can, for example, be advantageous if deflation of the volume-occupying subcomponent were initiated by a tearing or puncturing of the volume-occupying subcomponent wall, since such initial tear or puncture may then increase in scope, hastening and/or maximizing the deflation process.

The volume-occupying subcomponent may also be coated by a lubricious substance that facilitates its passage out of the body following its deflation. Examples of possible coatings can be any substances with lubricious and/or hydrophilic properties and include glycerin, polyvinylpyrrolidone (PVP), petroleum jelly, aloe vera, silicon-based materials (e.g. Dow 360) and tetrafluoroethylene (TFE). The coating may be applied by a dipping, sputtering, vapor deposition or spraying process which may be conducted at an ambient or positive pressure.

The balloon composite wall materials can be of similar construction and composition as those described in U.S.

Patent Publication No. 2010-0100116-A1, the contents of which is hereby incorporated by reference in its entirety. The materials are able to contain a fluid, preferably in compressed or non-compressed gas form, such as, e.g., $N_2$, Ar, $O_2$, $CO_2$, or mixture(s) thereof, or atmospheric air (composed of a mixture of $N_2$, $O_2$, Ar, $CO_2$, Ne, $CH_4$, He, Kr, $H_2$, and Xe) that simulate gastric space concentrations. In certain embodiments, the balloon is able to hold the fluid (gas) and maintain an acceptable volume for up to 6 months, preferably for at least 1 to 3 months after inflation. Particularly preferred fill gases include non-polar, large molecule gases that can be compressed for delivery.

Prior to placement in the outer container, the balloon is deflated and folded. In the inverted configuration in a deflated state, the balloon is flat, with the inverted seam extending around the perimeter of the balloon. The self-sealing valve system is affixed to the inner wall of the lumen close to the center of the deflated balloon, with the inner container positioned adjacent to the self-sealing valve system. The walls of the balloon are then folded. As part of the balloon design, the self-sealing valve system is manufactured in a manner such that it can be and is preferably placed "off center" to minimize the number of folds upon themselves (e.g., doubling or tripling up) required to fit the balloon in the outer container. For example, the self-sealing valve system can advantageously be placed ½ r±¼ r from the center of the balloon, wherein r is the radius of the balloon along a line extending from the center of the balloon through the septum.

Tracking and Visualization Subcomponent

It may also be beneficial to implement tracking and visualization functionality into devices according to the embodiments. Due to the non-invasive nature of the present device, physicians may desire to determine, or confirm, the location and orientation of the device prior to inflation or during the course of treatment.

A radiographic marker may be applied to the volume-occupying subcomponent when the volume-occupying subcomponent is in a creased or folded state such that when the volume-occupying subcomponent is in its deflated state the marker appears concentrated when viewed on visualization equipment, and when the volume-occupying subcomponent is inflated the marker appears less concentrated when viewed on visualization equipment. Alternatively, a marker may be applied or incorporated into the volume-occupying subcomponent at multiple positions so as to facilitate identification and location of the various subcomponents of the device, such as a valve, head, or weight. The marker may be printed or painted onto a surface of the volume-occupying subcomponent or between layers of the material forming the volume-occupying subcomponent. Alternatively, a metal coating as described below may be used as a marker to identify and/or locate the volume-occupying subcomponent. Metal coatings for visualizing the volume-occupying subcomponent may include silver, gold, tantalum or any noble metal. Alternatively, the marker may be applied to an elastomeric sleeve that covers all or part of the volume-occupying subcomponent.

In another embodiment, the volume-occupying subcomponent incorporates a subcomponent that changes mechanically upon inflation of the volume-occupying subcomponent, which mechanical change can be visualized using x-ray or other visualization equipment. For example, a mechanical portion of the volume-occupying subcomponent containing a visualization marker may elongate upon an increase in pressure in the volume-occupying subcomponent.

Alternatively, a marker may be formed using a metallized mesh located between layers of the material from which the volume-occupying subcomponent is constructed. The pattern or patterns formed by the imbedded marker will appear when the volume-occupying subcomponent is in an inflated, deployed state.

It is envisioned that marker materials may be incorporated into the volume-occupying subcomponent to facilitate various visualization techniques such as, for example, MRI, CT and ultrasound.

The volume-occupying subcomponent may also contain a dye or marker that is released upon deflation to indicate that the volume-occupying subcomponent cavity has been breached. Such dye or marker may, for example, be apparent in the patient's urine as an indication that the volume-occupying subcomponent has begun to deflate.

In yet further embodiments, microchips and other components employing electronic modalities may be used to locate and identify a device. Microchips analogous to those utilized for the identification of pets may be used to communicate device specific information and its approximate location. For example, a Wheatstone or other bridge circuit may be incorporated into the device and, together with RF "ping and listen" technology may be used as part of a system to determine the device's approximate location and measure and communicate device specific information. Such device specific information can include internal volume-occupying subcomponent pressure, which can indicate the degree of inflation of the volume-occupying subcomponent.

In yet further embodiments, mechanical, chemical, visual and other sensors may be included as part of the device to measure, record and/or transmit information relating to the device and/or the patient's internal environment. For example, the device may contain a camera or any of the other imaging and transmission components of a PillCam device. As an additional example, the device may contain sensors that measure, record and/or transmit information relating to stomach pH, stomach pressure, hormone levels, organ health, and organ safety.

Valve System

In preferred embodiments, a self-sealing valve system is attached to the balloon (e.g., on its inside surface) that is "universal" or compatible with the swallowable catheter and a physician-assisted catheter. The valve system serves to allow for balloon inflation using a miniature catheter that includes a needle assembly and also provides a mechanism for detachment of the catheter after inflation has been completed.

FIGS. 1A-D depict views representing a design of a self-sealing valve system which contains a self-sealing septum housed within a metallic concentric cylinder. In the inflatable configuration, the self-sealing valve system is preferably adhered to the underside of the balloon material such that only a portion of the valve protrudes slightly outside of the balloon surface to ensure a smooth surface. The valve system for the inflatable configuration can utilize the same self-sealing septum designed for the self-inflating configuration. The septum preferably consists of a material possessing a durometer of 20 Shore A to 60 Shore D. The septum is inserted or otherwise fabricated into the smaller cylinder of the concentric metallic retaining structure (FIGS. 2A-D) that is preferably cylindrical in shape. The smaller cylinder within the larger cylinder controls alignment of the catheter needle sleeve/needle assembly with the septum, provides a hard barrier so that the catheter needle does not pierce the balloon material (needle stop mechanism), and provides compression such that the valve/septum re-seals after inflation and subsequent needle withdrawal.

The concentric valve system can also provide radio opacity during implantation and is preferably titanium, gold, stainless steel, MP35N (nonmagnetic, nickel-cobalt-chromium-molybdenum alloy) or the like. Non-metallic polymeric materials can also be used, e.g., an acrylic, epoxy, polycarbonate, nylon, polyethylene, PEEK, ABS, or PVC or any thermoplastic elastomer or thermoplastic polyurethane that is fabricated to be visible under x-ray (e.g., embedded with barium).

Figure 3C:
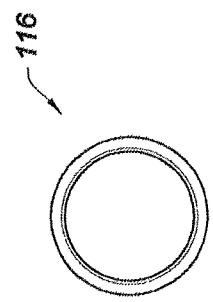
FIGS. 3A-C depict a perspective view (FIG. 3A), a side view (FIG. 3B), and a top view (FIG. 3C) of the ring stop 116 of the self-sealing valve system 100 of FIGS. 1A-D. The ring stop 116 is an additional ring placed at the distal end of the inner cylinder 118' to provide additional compression of the septum 114 between the ring stop 116 and the lip 118''', so as to ensure the septum material is dense enough to re-seal itself after engagement with a needle.
Figure 3A:
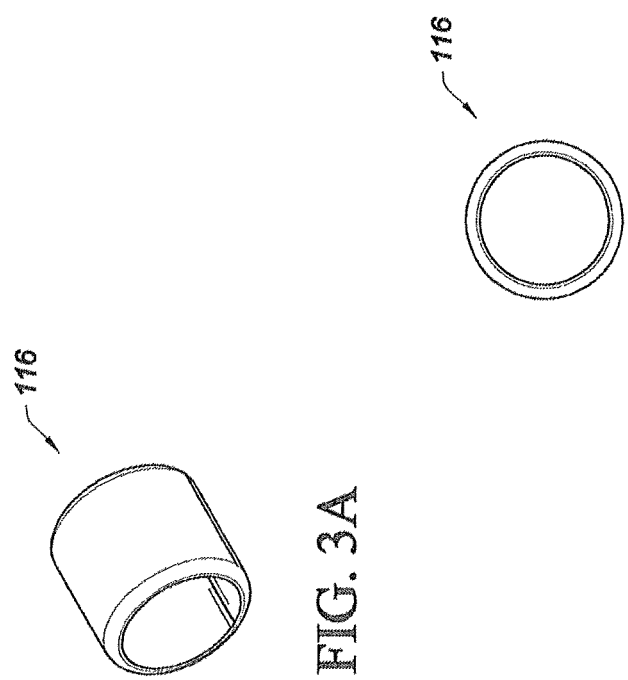
Figure 3B:
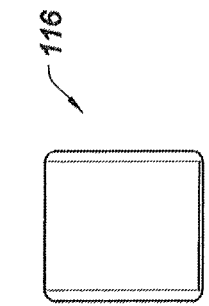
Figure 4B:
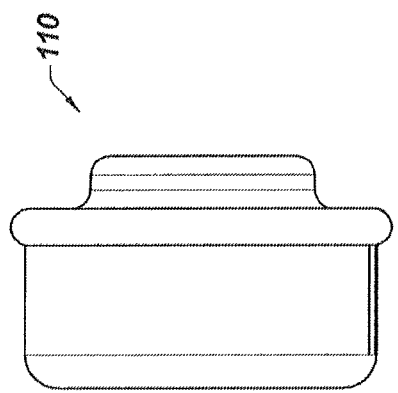
FIGS. 4A-D depict a perspective view (FIG. 4A), a side view (FIG. 4B), a top view (FIG. 4C) and a cross-sectional view (FIG. 4D) of the polymeric inner cylinder 110 of the self-sealing valve system 100 of FIGS. 1A-D. The cross-sectional view of FIG. 4D is taken along line 4D-4D of FIG. 4C.
Figure 4A:
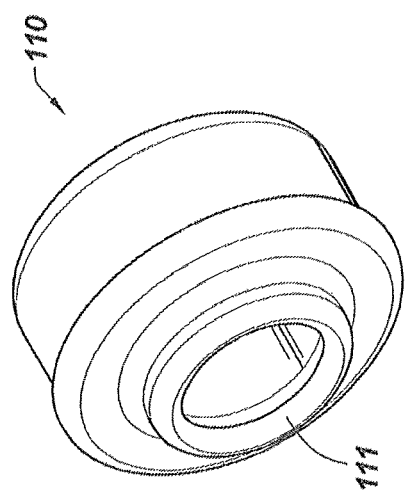
Figure 4D:
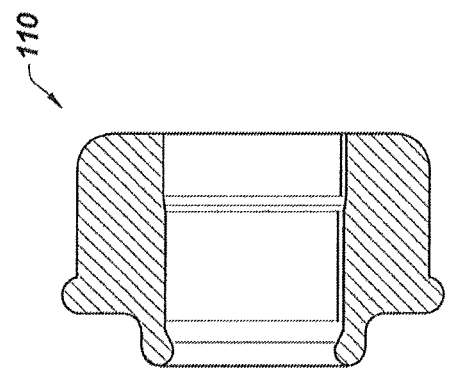
Figure 4C:
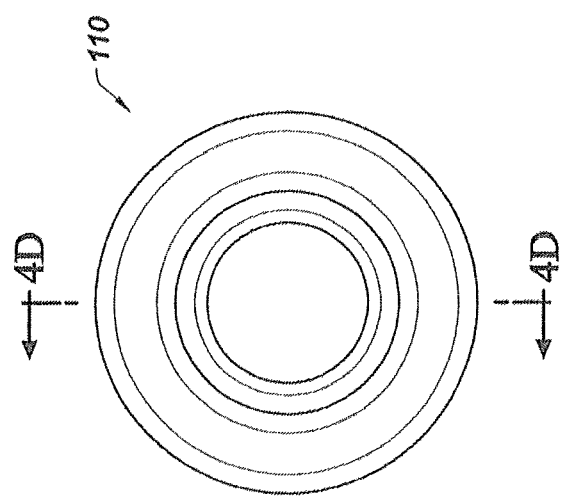

The septum can be cone shaped, so that the compressive forces are maximized for self-sealing after inflation. The self-sealing septum allows air to be evacuated from the balloon for processing/compacting and insertion into the outer container, and allows for piercing by an inflation agent syringe needle (self-inflating configuration) or inflation catheter needle (inflatable configuration), and then subsequent withdrawal of the inflation agent syringe needle or detachment of the inflation catheter and withdrawal of the catheter needle significantly limiting gas leakage outside of the balloon during the inflation process and needle withdrawal/catheter detachment. The septum is inserted into the valve using a mechanical fit mechanism to provide compression. An additional ring (FIGS. 3A-C) can be placed at the distal end of the inner cylinder to provide additional compression to ensure the septum material is pre-loaded so as to re-seal itself. The ring is preferably metallic in nature, but can also be a non-metallic polymeric material such as an acrylic, epoxy, or thermoplastic elastomer or thermoplastic polyurethane. The ring material is preferably the same material as the cylinder, titanium, but can also be gold, stainless steel, MP35N or the like.

Figures 5A, 5B, 5C:
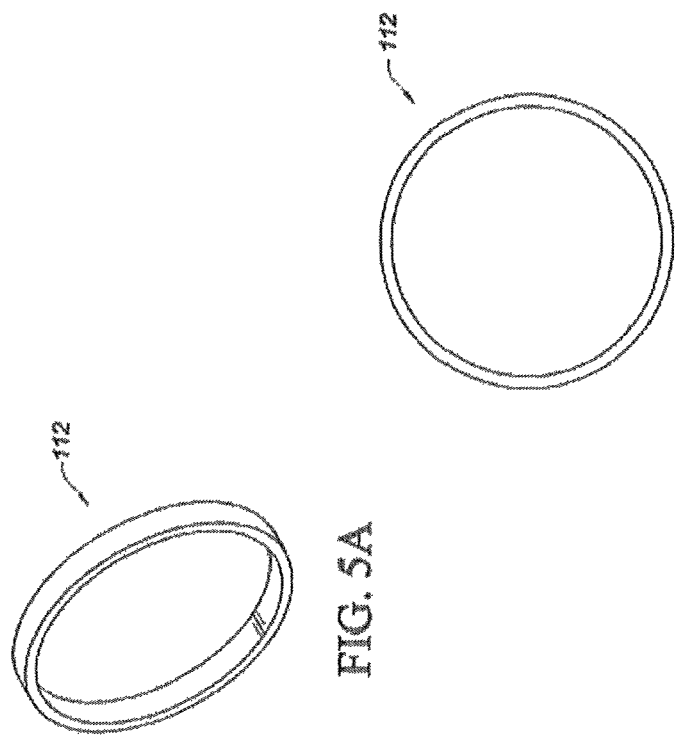
FIGS. 5A-C depict a perspective view (FIG. 5A), a side view (FIG. 5B), and a top view (FIG. 5C)—the retaining ring 112, of the self-sealing valve system 100 of FIGS 1A-D, which further enhances the seal between the metal and the valve silicone.

In an inflatable configuration, a larger, outer cylinder (FIGS. 4A-D) of the concentric valve housing contains a slightly harder durometer material than the inner cylinder (50 Shore A or greater), but is also preferably silicone. The purpose of using a harder durometer material is to ensure sealing when connected to the needle sleeve for inflation. The silicone located in the outer ring of the concentric valve is adhered to the balloon from the inside surface. The entire outer cylinder is filled and a small circular lip of this same material is provided that is slightly larger than the diameter of the inner cylinder and extends to the outside surface of the balloon. The lip is compatible with the bell shaped needle sleeve and provides sealing to enhance connection of the valve to the catheter to withstand the inflation pressures applied and also increases the ejection distance or attachment force of the catheter. This silicone lip preferably does not protrude past the balloon surface more than 2 mm to ensure that the balloon surface remains relatively smooth and does not cause abrasion or ulcerations of the mucosa. It is designed to provide compressive forces against the needle sleeve of the catheter for inflation and detachment whereby when connected to the needle sleeve of the inflation catheter, the connection coupling can preferably withstand a pressure of 35 PSI during inflation. The seal is then broken during detachment using hydraulic pressure that is preferably more than 40 PSI but less than 200 PSI to separate the coupling. An additional retaining ring (FIGS. 5A-C) preferably made of the same material as concentric valve, can be included in the valve system to further enhance the seal between the metal and the valve silicone and provide additional mechanical support to ensure proper mechanical fit and are intended to disrupt slippage of the silicone material from the hard (metallic) valve system (causing an increase in tensile force).

The valve structure for the inflatable configuration uses a mechanical fit mechanism to provide the functions of the self-sealable valve for inflation by the catheter and subsequent catheter detachment; however, primer and/or adhesive may be used to provide additional support in construction of the assembly. The configuration can be modified by modifying the surfaces of the metal components, making them more sticky or slippery e.g. more or less conducive to adhesion, to provide the desired mechanical/interference fit. The interference fit between the valve and the catheter can be modified to change the pressure requirements for inflation and/or detachment. Additional assemblies can include overmolding the metallic portions or the concentric system in silicone such that additional support rings to ensure the mechanical fit and the tensile strength and forces required to sustain the assembly during catheter inflation and detachment can be omitted.

The total valve diameter in the inflatable configuration is designed to fit a miniature catheter system that does not exceed 8 French (2.7 mm, 0.105 inches) in diameter. The total diameter does not exceed 1 inch (2.54 cm) and is preferably less than 0.5 inches (1.27 cm), to facilitate swallowing. Additional valves can be added, if desired; however, it is generally preferred to employ a single valve so as to maintain the volume of the deflated/folded balloon (and thus the outer container dimensions) as small as possible. The valve system is preferably attached to the balloon and bonded such that a shear force greater than 9 lbs (40 N) is required to dislodge the valve system.

In a self-inflating configuration, the valve system can be attached to the balloon (e.g., on its inside surface) without the use of an opening, orifice, or other conduit in the wall of the balloon. The valve system can utilize a septum with a durometer of 20 Shore A to 60 Shore D. The valve can be inserted or otherwise fabricated into a retaining structure that has a higher durometer, e.g., 40 Shore D to 70 Shore D or more. The retaining structure can be fabricated from a silicone, rubber, soft plastic or any suitable non-metallic polymeric material such as an acrylic, an epoxy, a thermoplastic elastomer, or thermoplastic polyurethane. Preferably, a structure, such as a ring, that can be metallic or non-metallic but radio opaque (e.g., barium) and visible under X-ray, can be embedded in the retaining structure. Using a mechanical fit mechanism of two structures of different durometers, one softer (septum) with a large diameter, can be inserted into a snug, a higher durometer structure creates compressive forces in the once open orifice to enable $CO_2$ retention and reduce susceptibility for $CO_2$ gas leaks. The metallic ring for radio-opacity also helps to support compressive forces on the septum. The self-sealing septum allows air to be evacuated from the balloon for processing/compacting and inserting in the outer container, and also allows for the inflation agent to be injected into the outer container for inflation initiation. Additional septums can be provided, if desired; however, it is generally preferred to employ a single septum so as to minimize the volume of the deflated/folded balloon (and thus the outer capsule) to as small as possible. The valve system is preferably attached to the inside of the balloon such that a shear force greater than 9 lbs (40 N) is required to dislodge the valve system. A silicone head and radio opaque ring of a self-sealing valve system can be employed, as can a wedge-shaped septum.

In the self-inflating configuration, an inoculation spacer is preferably incorporated to guide a needle into the self-sealing valve for injection of liquid activation agent into the lumen of the balloon and to prevent the needle from penetrating the wall of the deflated/folded balloon elsewhere such that pressure within the lumen of the balloon cannot be maintained. The inoculation spacer also facilitates preventing liquid activation agent from penetrating the inner container or the folded balloon material, thereby focusing the activation agent in an appropriate manner to properly mix the reactants for $CO_2$ generation according to the criteria described above. The inoculation spacer is generally in the form of a tube or cylinder. The inoculation spacer is preferably attached to the inner container and/or the self-sealing valve system with an adhesive or other fixing means; however, in certain embodiments the inoculation spacer can be "free-floating" and maintained in position by the folding or rolling of the walls of the balloon. The inoculation spacer can comprise any suitable material that can be passed after separation, erosion, degradation, digestion, and/or dissolution of the outer container; however, preferable materials include non-metallic materials with a minimum Shore D durometer of 40 or more, any metallic material, or a combination thereof. A cupped needle stop (inoculation spacer) can be employed in preferred embodiments.

Balloon

In a preferred embodiment, a self-inflating balloon is fully sealed 360 degrees around. In the self-inflating configuration, with injection of an inflation agent by needle syringe, there are preferably no external openings or orifices to the central lumen. In the inflatable configuration, a valve structure (either protruding, recessed, or flush with the surface of the balloon) is provided for providing an inflation fluid to the central lumen. The balloon can have a "noninverted", "inverted", or "overlapped" configuration. In a "noninverted" configuration, the seams or welds and seam allowance, if any, are on the outside of the inflated balloon. In an "overlapped" configuration, layers are overlapped, optionally with one or more folds, and secured to each other via welds, a seam, adhesive, or the like, resulting in a smooth external surface. In an "inverted" configuration, the balloon has a smooth external surface with seams, welds, adhesive bead, or the like inside the inflated balloon. In order to create a balloon with an inverted configuration, e.g., a balloon with no external seam allowance (no wall material between the edge of the balloon and the weld, seam, or other feature joining the sides together), two balloon halves are joined together in some fashion (e.g., adhered using adhesive or heat or the like based on the balloon material used). One of the balloon halves encompasses an opening to allow for the balloon to be pulled through itself after adherence of the two halves and to have the seams of the balloon on the inside. The opening created is preferably circular but can be any similar shape, and the diameter of the opening preferably does not exceed 3.8 cm; however, in certain embodiments a larger diameter may be acceptable. A patch of material is adhered (adhesively, heat welded, or the like, based on the material used) to cover the original balloon-half opening. The inversion hole thus created that is subsequently patched is small enough that the forces exerted during inflation do not compromise the material used to maintain fluid in the balloon. The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 cm$^3$ to 350 cm$^3$ (at 37° C. and at internal nominal pressure and/or full inflation), an internal nominal pressure (at 37° C.) of 0 psi (0 Pa) to 15 psi (103421 Pa), and a weight of less than 15 g. The self-inflating balloon is configured for self-inflation with $CO_2$ and is configured to retain more than 75% of the original nominal volume for at least 25 days, preferably for at least 90 days when residing in the stomach. The inflatable balloon is configured for inflation with an appropriate mixture of gases so as to deliver a preselected volume profile over a preselected time period (including one or more of volume increase periods, volume decrease periods, or steady state volume periods).

The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 cm$^3$ to 350 cm$^3$ (at 37° C. and at internal nominal pressure and/or full inflation), an internal nominal pressure (at 37° C.) of 0 psi (0 Pa) to 15 psi (103421 Pa), and a weight of less than 15 g. In certain embodiments wherein a stable volume over the useful life of the device is preferred, the balloon is configured to maintain a volume of at least 90% to 110% of its original nominal volume. In other embodiments, it can be desirable for the balloon to increase and/or decrease in volume over its useful life (e.g., in a linear fashion, in a stepwise fashion, or in another non-linear fashion).

Inner Container

The inner container for the self-inflating balloon is contained within the lumen of the balloon and contains the $CO_2$ generator for balloon self-inflation. The $CO_2$ generator comprises an inflation agent mixture housed within the container. Preferably, from about 10% to about 80% of the total inflation agent used comprises powdered citric acid, with the remainder comprising powdered sodium bicarbonate. Sufficient inflation agent is provided such that upon completion of the $CO_2$ generating reaction, the balloon achieves inflation at the nominal inflation pressure described above. Preferably, a total of from about 0.28 to 4 grams inflation agent mixture is employed, depending upon the balloon size to be inflated; preferably up to 1.15 grams of sodium bicarbonate is used with the remainder being powdered citric acid to generate 300 cm$^3$ of $CO_2$ at nominal pressure.

Inflation Assembly for Manual Balloon Inflation

An intragastric balloon system that is manually inflated by a miniature catheter can be employed in certain embodiments. The system preferably remains "swallowable." The balloon for delivery is in a compacted state and is attached to a flexible, miniature catheter, preferably no larger than 4 French (1.35 mm) in diameter. The catheter is designed such that a portion of the catheter can be bundled or wrapped upon itself for delivery with the encapsulated balloon, allowing the patient to swallow both catheter and balloon for delivery to the stomach. The balloon can contain a self-sealable valve system for attachment of the catheter and inflation of the balloon once it reaches the stomach cavity. The proximal end of the catheter can be left just outside of the patient's mouth, permitting connection to an inflation fluid container that can house the preferred inflation fluid (gas or liquid). After inflation the catheter can be detached from the balloon valve and pulled back through the mouth. This method allows for the intragastric balloon to maintain its swallowability but allow for inflation by a fluid source or a mixture of fluid sources via the catheter. Alternatively, a more rigid, pushable system can be employed wherein the balloon valve is compatible with either the swallowable, flexible catheter or the pushable, rigid catheter assembly.

The inflation catheters (swallowable or administrator-assisted pushable) described herein are configured to deliver the balloon device orally and without any additional tools. The administration procedure does not require conscious sedation or other similar sedation procedures or require endoscopy tools for delivery. However, other versions of the device can be used in conjunction with endoscopy tools for visualization or can be adapted such that the balloon device can be delivered nasogastrically as well.

Figure 6:
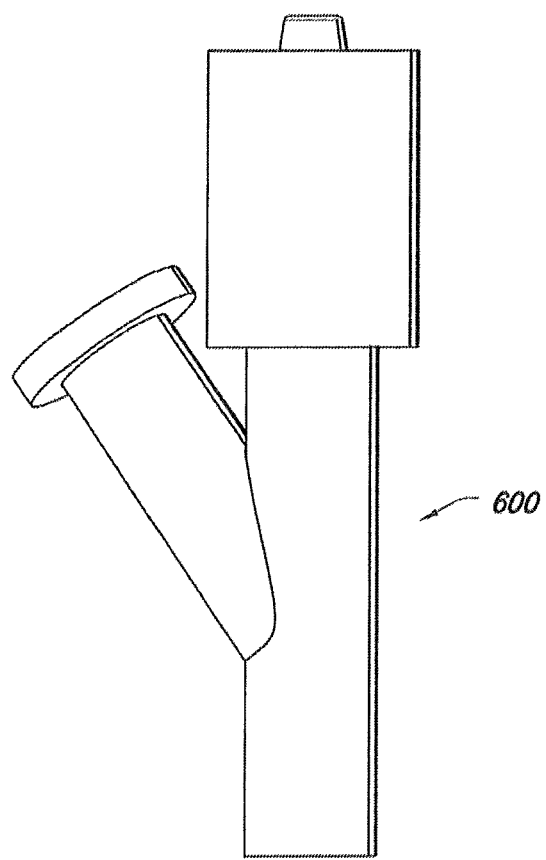
FIG. 6 depicts a connector 600 for a dual lumen catheter.
Figure 7:
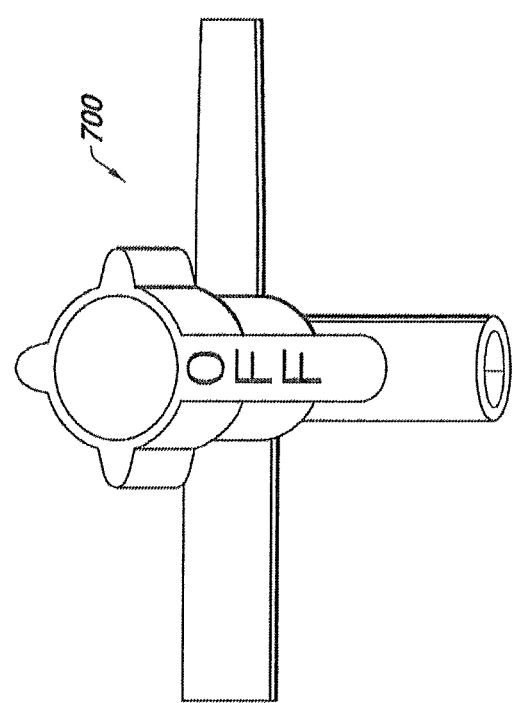
FIG. 7 depicts an inflation valve 700. The inflation valve 700 is a 3-way valve configured for attachment to a single lumen catheter and that allows a method of exclusion for inflation and detachment of the balloon.
Figure 8A:
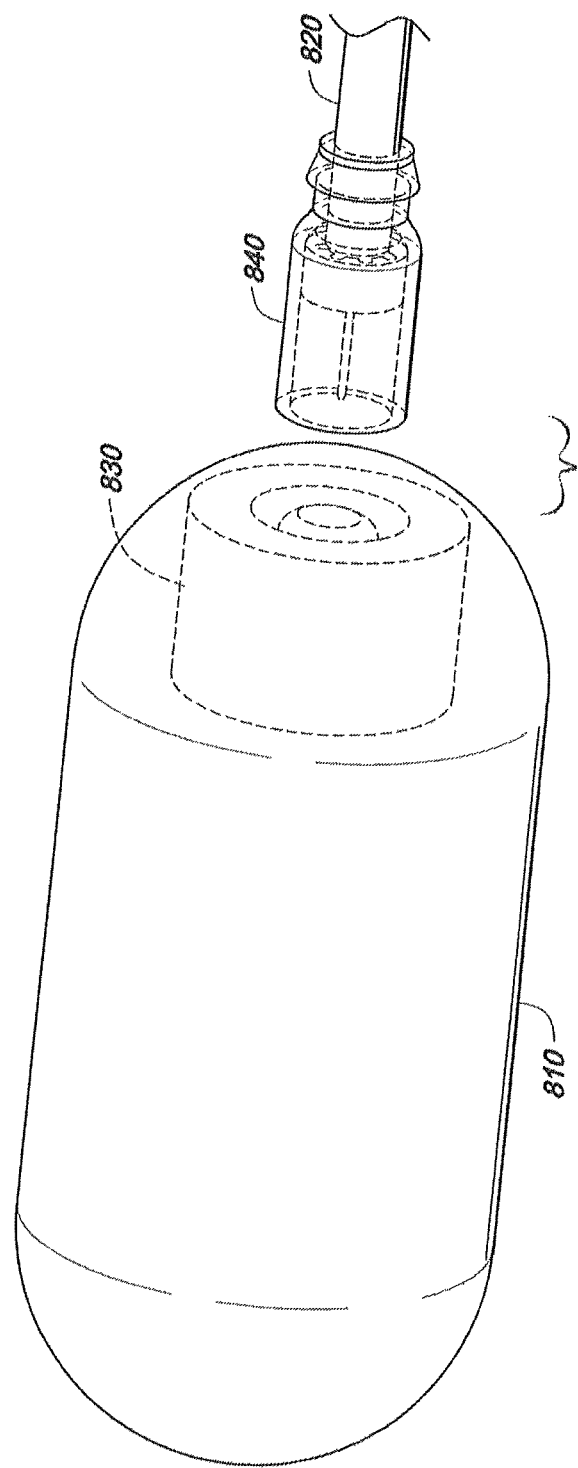
FIGS. 8A-B depict a universal balloon valve 800 (shown in phantom) attached to an intragastric balloon (not shown) encased within a capsule 810. The universal balloon valve 800 is adapted for connection to an inflation catheter 820 with a bell-shaped needle sleeve 840, portions of which are shown in phantom so as to show greater detail thereof.
Figure 8B:
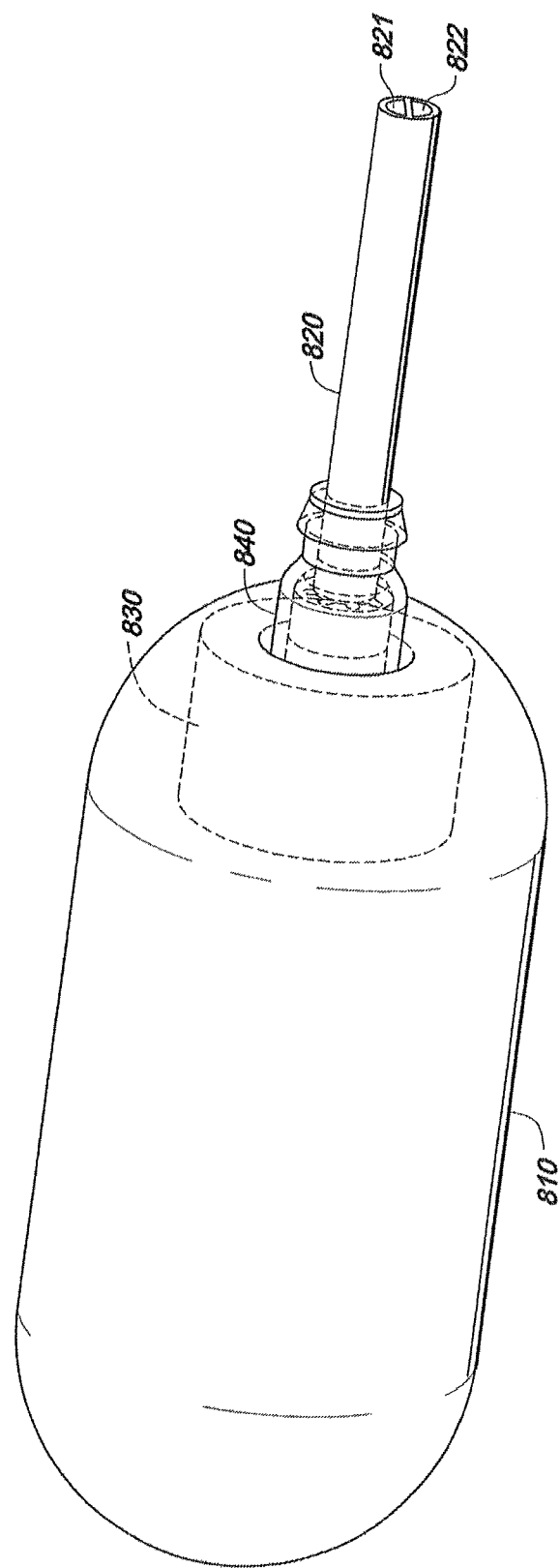

In operation, the proximal end of the inflation catheter is connected to a valve or connector that allows for connection to the inflation source or the disconnect source, this is preferably a connector or inflation valve (FIG. 6 and FIG. 7, respectively). The connector materials may consist of polycarbonate or the like and can connect to a single or multi-lumen catheter tube. The distal end of the inflation catheter is connected to the universal balloon valve of the balloon that has been compacted and housed within a gelatin capsule or compacted using gelatin bands (FIG. 8A-B). The catheter tube is preferably from 1 French (0.33 mm) to 6 French (2 mm) in diameter. The catheter is preferably long enough to extend out past the mouth (connected to the inflation connector or valve) and transverse the esophagus down to at least the middle of the stomach—approximately 50-60 cm. Measurement ticks can be added to the tubing or catheter to aid in identifying where the end of the tube is located. Timing for inflation can be initiated by having the tube contain a pH sensor that determines a location difference between the esophagus (pH 5-7) and the stomach (pH 1-4) based on the different pH between the two anatomical sources, or can be derived or verified from the expected pressure in a contained (i.e., esophagus) versus a less-constrained space (i.e., stomach). The tube can also contain nitinol that has a tunable transmission to the body temperature, taking into account the timing for swallowing. The tube can also be connected to a series of encapsulated or compacted balloons on a single catheter. Each can be inflated and released separately. The number of balloons released can be tune-able to the patient's needs and desired weight loss.

In certain embodiments, a catheter with the balloon at the distal end (inflated with air) is employed to temporarily and firmly hold the balloon in place. A small deflated balloon catheter can be positioned through the head of the gastric balloon (e.g., a "balloon within the balloon"), and then inflated with air during delivery to firmly hold the capsule and balloon in place and prevent spontaneous detachment of balloon from the catheter. This balloon catheter can incorporate a dual channel that can also allow the bigger gastric balloon to be inflated (by gas or liquid). Once the gastric balloon has been satisfactorily inflated, the small air balloon catheter can be deflated and pulled out of the valve (allowing the valve to self-seal), and out of the body, leaving the inflated gastric balloon in the stomach.

In other embodiments, the catheter may be coated to enhance swallowability or is impregnated or treated with a flavored version and/or one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

Dual Lumen Catheter

Figure 9A:
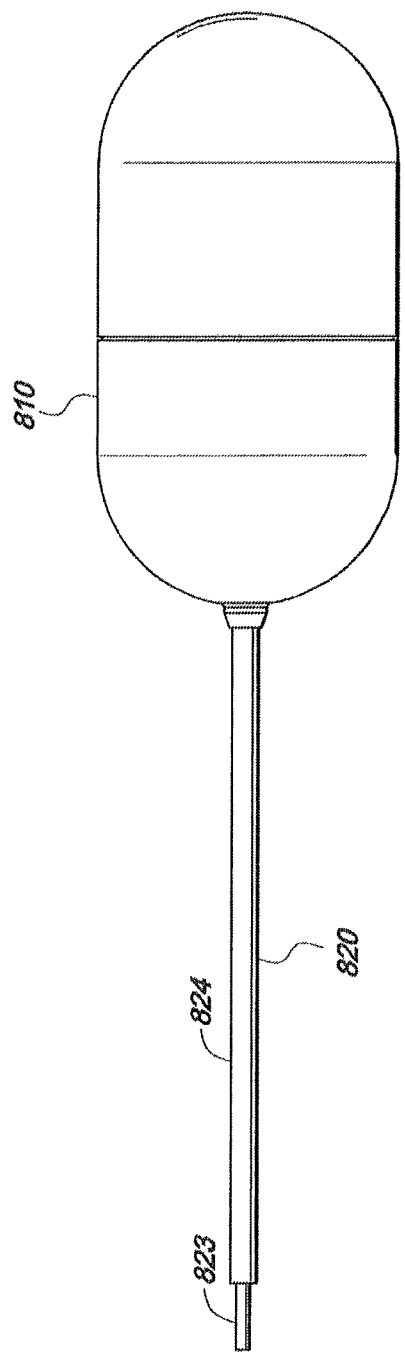
FIGS. 9A-C depict a side view (FIG. 9B), a bottom view (FIG. 9B) and a top view (FIG. 9C) of another dual lumen catheter 820 coupled to a balloon (not shown) encapsulated within a gel capsule 810, sometimes referred to as a "gel cap", wherein the dual lumen catheter 820 includes a thin first catheter 823 disposed within a slightly larger second catheter 824.
Figure 9C:
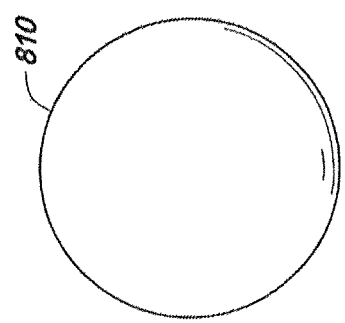
Figure 9B:
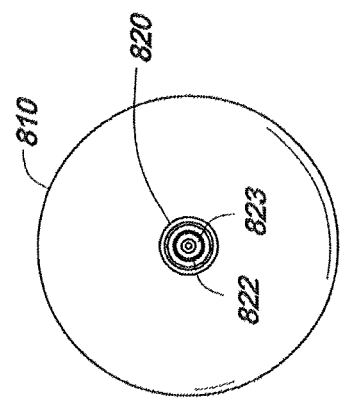
Figure 10B:
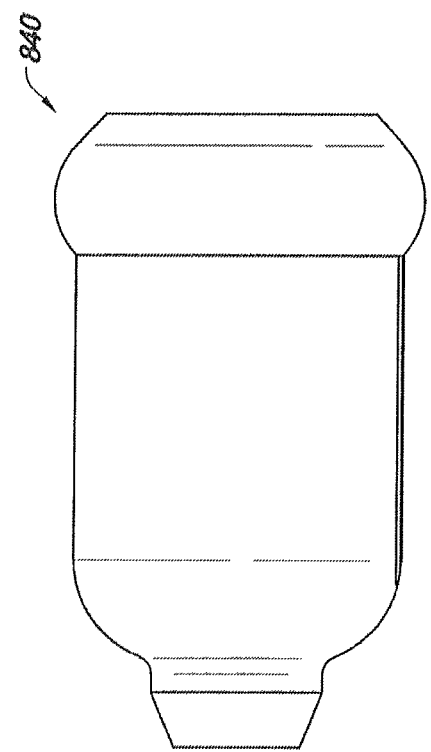
FIGS. 10A-D depict a perspective view (FIG. 10A), a side view (FIG. 10B), a top view (FIG. 10C), and a cross-sectional view (FIG. 10C) of another bell-shaped needle sleeve 840, wherein the cross-section of FIG. 10D is taken along line 10D-10D of FIG. 10C.
Figure 10A:
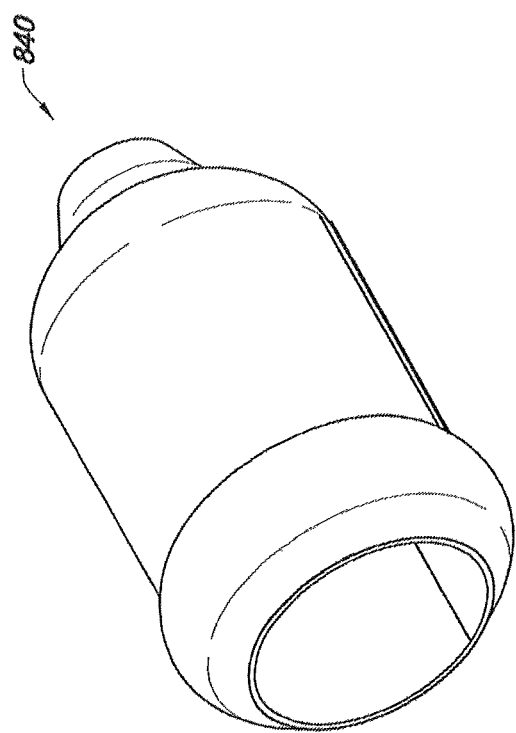
Figure 10D:
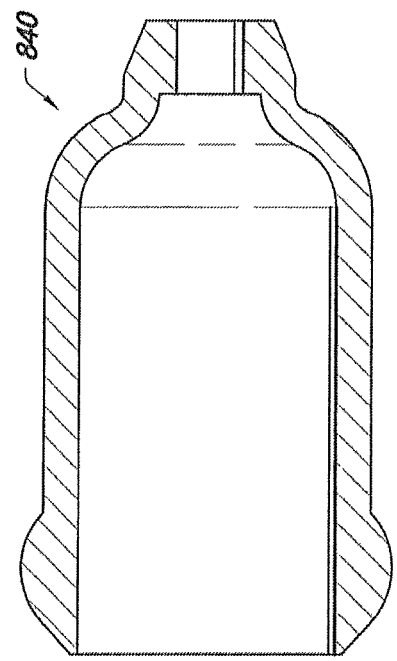
Figure 10C:
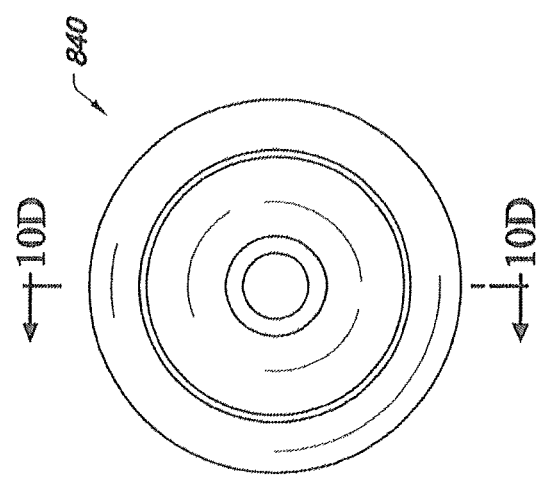

In a preferred embodiment, a swallowable dual lumen catheter is provided. The dual lumen catheter (FIGS. 9A-C) has two lumens with a diameter of the complete assembly no larger than 5 French (1.67 mm), preferably no larger than 4 French (1.35 mm). The inner lumen preferably does not exceed 3 French (1 mm) and functions as the inflation tube, and the outer lumen preferably does not exceed 5 French (1.67 mm) and functions as the disconnection tube. The catheter assembly is connected to a needle assembly, described in more detail below, at the distal end and to a dual port inflation connector at the proximal end. The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible and have moderate tensile strength and a significant amount of hoop strength to handle applied pressures. The lumens are preferably round and co-axial and free-floating so as to provide flexibility. The dual lumen assembly also preferably requires no adhesive or glue. Alternative lumen configurations can include two D-lumens or a combination of a D-lumen and round lumen, and can be used in stiffer configurations of the final catheter assembly. Preferred materials for the tubing include a thermo-resistant polyethylene tubing such as PEBAX® or a thermo resistant polyurethane tubing such as PEL-LETHANE™, PEEK or Nylon. The tubing can also be manufactured out of bioresorbable materials such as polylactic acid (PLA), poly-L-aspartic acid (PLAA), polylactic/glycolic acid (PLG), polycaprolactone (PCL), DL-lactide-co-ε-caprolactone (DL-PLCL) or the like, wherein the tube can be released after inflation and detachment and swallowed as normal.

At the distal end of the catheter assembly, the inner lumen or inflation tube is attached to the needle assembly that is used to puncture the balloon's self-sealing valve, preferably located at one of the apexes of the balloon housed inside of a gelatin capsule as outer container. The outer lumen is connected to the needle sleeve and provides connection force between the catheter assembly and balloon providing the tensile strength to withstand starting inflation pressures of preferably up to 10 psi and preferably no more than 35 PSI while maintaining the assembly together. The needle sleeve is configured to mechanically couple with the balloon valve assembly. The needle is preferably made of metal, preferably stainless steel or the like, with a maximum size of 25 gauge (0.455 mm), preferably no smaller than 30 gauge (0.255 mm) for inflation timing purposes. The needle sleeve is preferably a soft material such as nylon or the like, or can also be polycarbonate, polyethylene, PEEK, ABS or PVC. The needle sleeve covers the length of the needle in its entirety, such that the body is protected from the needle and the needle can only pierce the balloon septum. Preferably the needle sleeve is flush or extends out slightly more than the needle length. The needle is inserted into the balloon septum prior to swallowing and maintains a retention force of approximately 0.5 lb when coupled to the silicone area of the balloon valve. The needle sleeve is preferably slightly bell shaped (FIGS. 10A-D) or contains a circular relief or lip so that when inserted into the silicone area of the valve a lock and key mechanism is created to increase the tensile strength of the assembly and enhance the sealing for inflation.

At the proximal end, the catheter assembly is connected to a Y-adapter assembly preferably made of polycarbonate. The y-adapter is "keyed" so that the inflation gas and connection fluid are connected to the catheter assembly appropriately and travel down the correct lumen.

Prior to inflation, priming of the disconnection lumen may be employed using a liquid. For example, the outer lumen is first flushed with 2 cm$^3$ of water, saline, DI water or the like prior to balloon inflation. Thereafter, the inflation source container is attached to the connector leading to the inner lumen. The inflation source container works on the premise of the ideal gas law and a pressure decay model. For a given compressed gas formulation, the device is designed to equalize such that a higher starting pressure is used to inflate the balloon than is the resulting end pressure of the balloon. The starting pressure and volume are dependent upon the gas formulation selected, as well as the length of the catheter and the starting temperature (typically ambient temperature) and ending temperature (typically body temperature).

After inflation, the balloon is detached from the catheter assembly using hydraulic pressure. A syringe filled with water, DI water, or preferably saline is attached to the female end of the Y-assembly. The syringe contains 2 cm$^3$ of liquid and when the syringe plunger is pushed in, enough hydraulic pressure is exerted such that the needle is ejected from the balloon valve.

Single Lumen Catheter

Figure 11A:
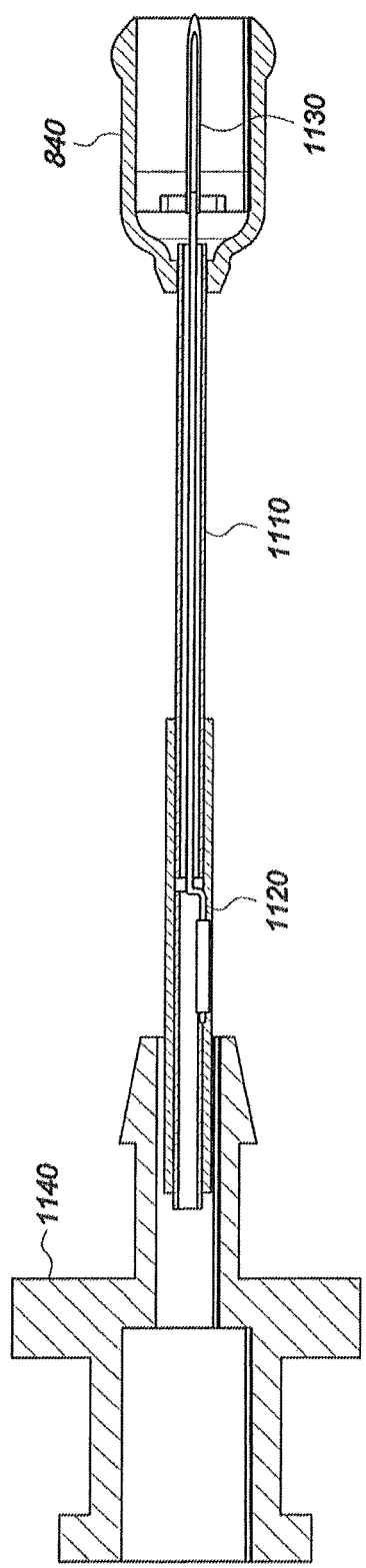
FIGS. 11A-C depict various embodiments of a single lumen catheter 1110.
Figure 11B:
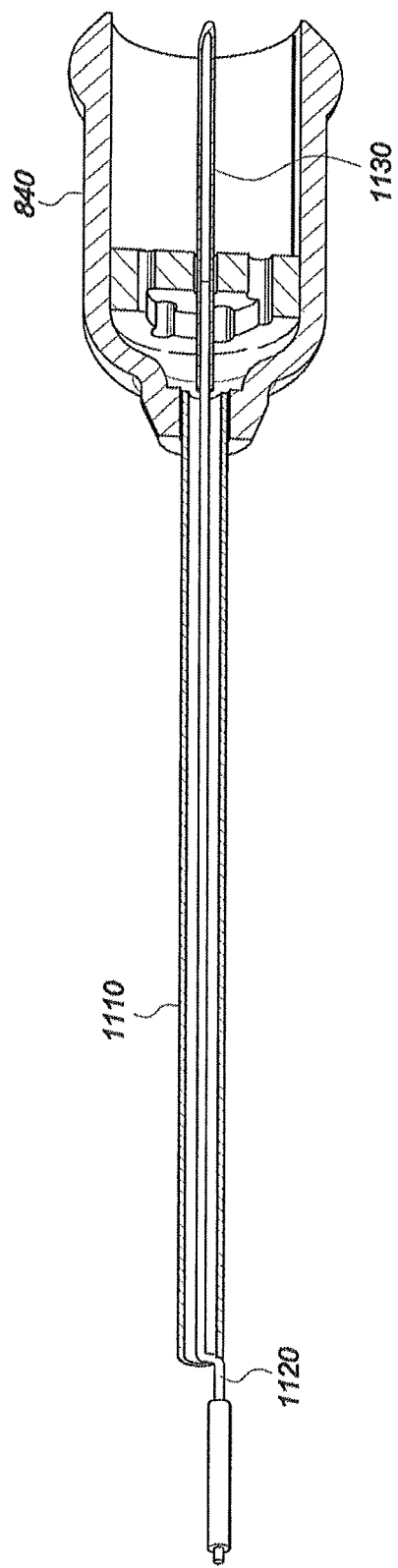

To further reduce the diameter of the inflation catheter, thereby increasing swallowability comfort of the balloon capsule and catheter, a single lumen catheter (FIG. 11A-C) can be employed that does not exceed 3 French (1.0 mm) in diameter (0.033 inches).

The needle/needle sleeve assembly is similar in design to that of the dual lumen catheter described herein. However, with the single lumen system, the distal end of the catheter lumen connects to the needle sleeve only and there is no second catheter inside. Instead, a single thread attached to a needle hub runs co-axially the length of the catheter to aid in tensile strength for detachment and overall flexibility.

The needle sleeve is slightly bell shaped or contains a circular relief or lip so that when inserted into the silicone head of the valve a lock and key mechanism is created to increase the tensile strength of the assembly, enhance the sealing for inflation, and since this is a single lumen assembly, the lip increases the force required to remove the needle from the valve so this does not occur haphazardly during the inflation process.

The proximal end of the catheter is connected to an inflation valve (FIG. 7), preferably a 3-way valve, or any valve that allows for using a method of exclusion for inflation and detachment of the balloon. The distal end of the catheter contains the needle sleeve, which is made of nylon or other similar source. The needle is metallic and preferably stainless steel.

The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible and resistant to necking or buckling or kinking. For a single lumen system, the catheter tubing is preferably made of PEBAX® or PELLETHANE® (an ether-based polyurethane elastomer), but can also comprise bioresorbable materials such as PLA, PLAA, PLG, PCL, DL-PLCL or the like, wherein the tube can be released after inflation and detachment and swallowed as normal. The threadlike wire (FIG. 11B) inside the catheter tubing attached to the needle is preferably a nylon monofilament, but Kevlar or nitinol wire or other suitable materials can also be used.

Figure 11C:
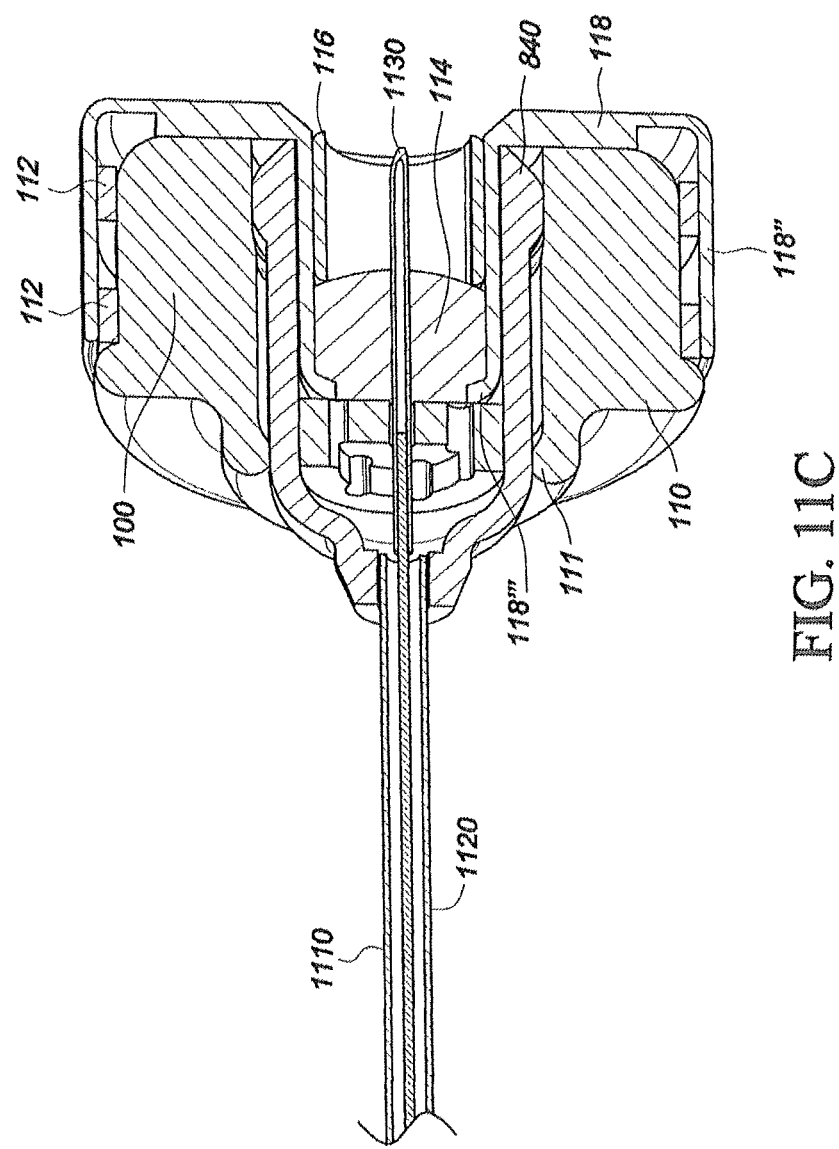
Figure 12B:
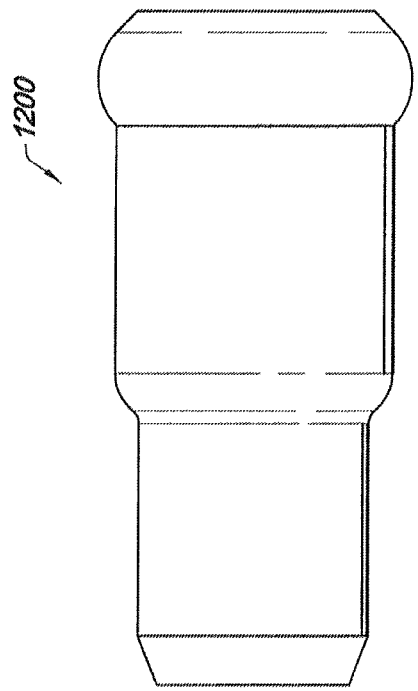
FIGS. 12A-D depict a perspective view (FIG. 12A), a side view (FIG. 12B), a top view (FIG. 12C), and a cross-sectional view (FIG. 12C, the cross-section being taken along line 12D-12D of FIG. C) of another needle sleeve 1200, which is configured to accommodate a larger diameter tube.
Figure 12A:
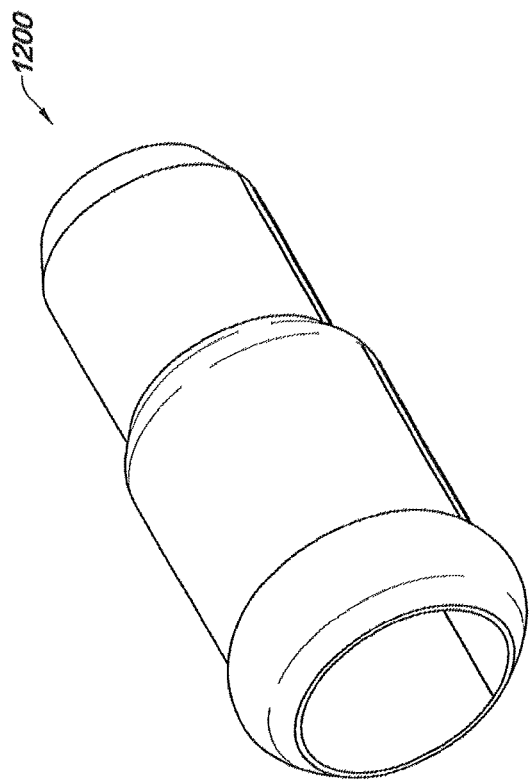
Figure 12C:
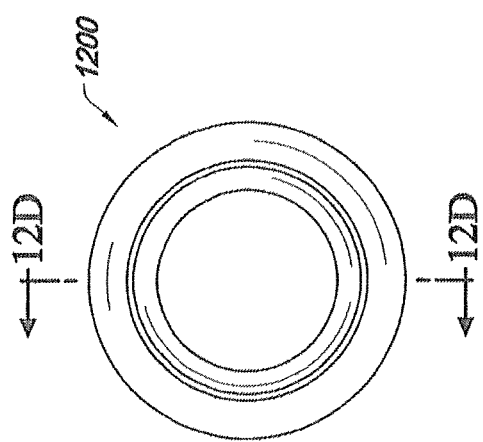
Figure 12D:
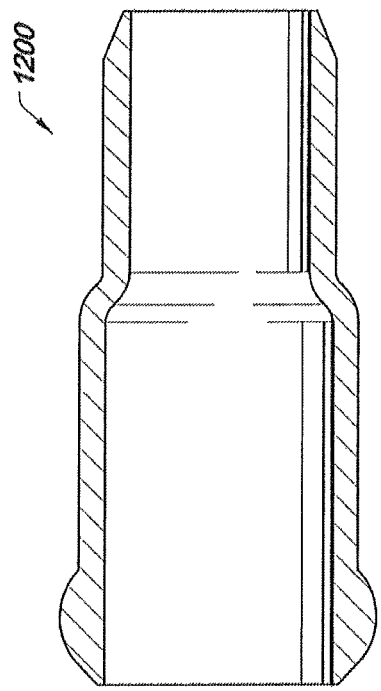

To inflate the balloon, the distal end of the catheter is attached to the balloon capsule where the needle protrudes through the self-sealable valve (FIG. 11C). The container is swallowed and a portion of the inflation catheter remains outside of the mouth. The inflation source container is connected to the proximal end of the inflation valve, where the port for inflation gas is chosen by excluding the other ports. The inflation fluid (preferably compressed nitrogen gas or a mixture of gases) travels down the single catheter lumen, whereby the inflation gas selects the path of least resistance, or more specifically through the needle cavity and into the balloon. The balloon is preferably inflated in less than 3 minutes.

To detach and withdraw the needle from the balloon valve, 2 cm$^3$ or other suitable volume of water or other liquid is injected into the catheter at a high pressure. Since water has a high surface tension and viscosity, it occludes the needle pathway and the pressure is transferred to the outside needle sleeve, thereby breaking the fit between the needle sleeve and the balloon valve.

If it is desired to place a substance inside the balloon, such as water or acid or any alternative liquid, it can be done by using a lower pressure to inject the liquid.

Miniature Stiff-Bodied Inflation Catheter

In certain embodiments, a stiff-bodied inflation catheter can be employed, which can be placed orally or transnasally. This system can be from 1 French (0.33 mm) to 10 French (3.3 mm), preferably 8 French (2.7 mm) in diameter. A larger diameter is typically preferred to enhance pushability, with wall thickness also contributing to pushability and kink resistance. The length of the tube can be approximately 50-60 cm. As discussed above, measurement ticks can be added to the tubing to identify where the end of the tube is located, or a pH or pressure sensor on the catheter can be employed to detect location of the balloon.

This system for inflation/detachment is similar to the dual lumen system described above, but with a larger needle sleeve to accommodate the larger diameter tube (FIGS. 12A-D). Materials that can be used in the lumen include, e.g., expanded polytetrafluoroethylene (EPTFE) for the outer lumen and polyetheretherketone (PEEK) for the inner lumen. To also enhance pushability, a strain relief device can be added to the distal and proximal ends. It is particularly preferred to have strain relief at the distal end, e.g., 1 to 8 inches, preferably 6 inches, to ensure the catheter bypasses the larynx and follows into the esophagus. The proximal end can have strain relief as well, e.g., to ensure fit of the connector. The preferred material for the strain relief is a polyolefin. The method for inflation/detachment is the same method as for the dual lumen configuration where the outer lumen connects to the needle sleeve and the inner lumen connects to the needle. Stiffening members are strategically placed along the length of the catheter shaft to provide the correct amount of flexibility and pushability to properly place the device in the patient. As part of the procedure, the patient can swallow water or other suitable liquid so as to distend esophageal tissue for smooth passage down of the device. Patients can also be administered an anesthetic at the back of the throat to numb the area and lessen the gag reflex.

The tube can also be connected to a series of encapsulated or compacted balloons on a single catheter such that a total volume of up to 1000 cm$^3$ or more can be administered, as necessary. Each can be inflated and released separately. The number of balloons released can be tunable to the patient's needs and desired weight loss.

Figure 13:
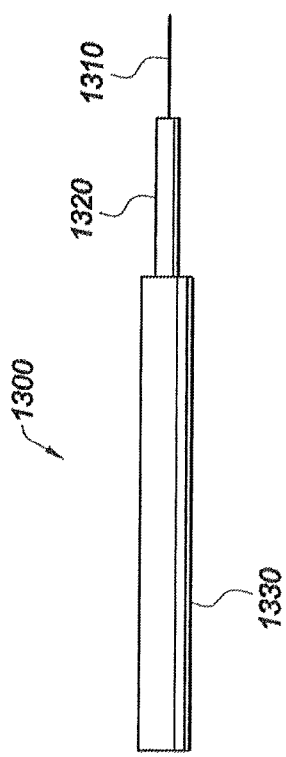
FIG. 13 depicts a variable stiffness catheter 1300 for administering a gastric balloon, the catheter 1300 including a first portion 1310 having a first stiffness, a second portion 1320 having a second stiffness and a third portion 1330 having a third stiffness.

In addition, a catheter can be used for administering a gastric balloon that is similar to balloon catheters used in angioplasty termed "over-the-wire" or rapid exchange catheters (FIG. 13). In this case where the patients attempts to swallow the catheter but fails so the stiff catheter or physician assisted catheter can slide over the flexible catheter and the balloon can be pushed down in the same manner as the physician-assisted catheter. Different materials can be used to provide the varying degrees of flexibility or one material that is fabricated with different diameters across the length to vary the degree of stiffness can be used.

Inflation Fluid Container

Figure 14A:
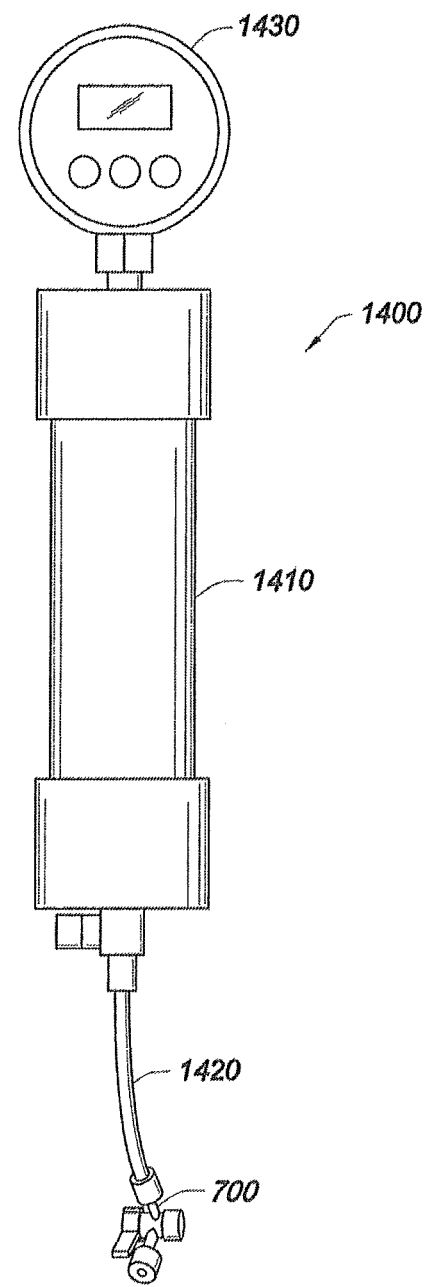
FIGS. 14A-C depict an inflation fluid container system 1400, in one embodiment, including an inflation fluid (or source) container 1410, a valve 700, an extension tube connector 1420 to the catheter (not depicted) and a pressure gauge 1430.
Figure 14B:
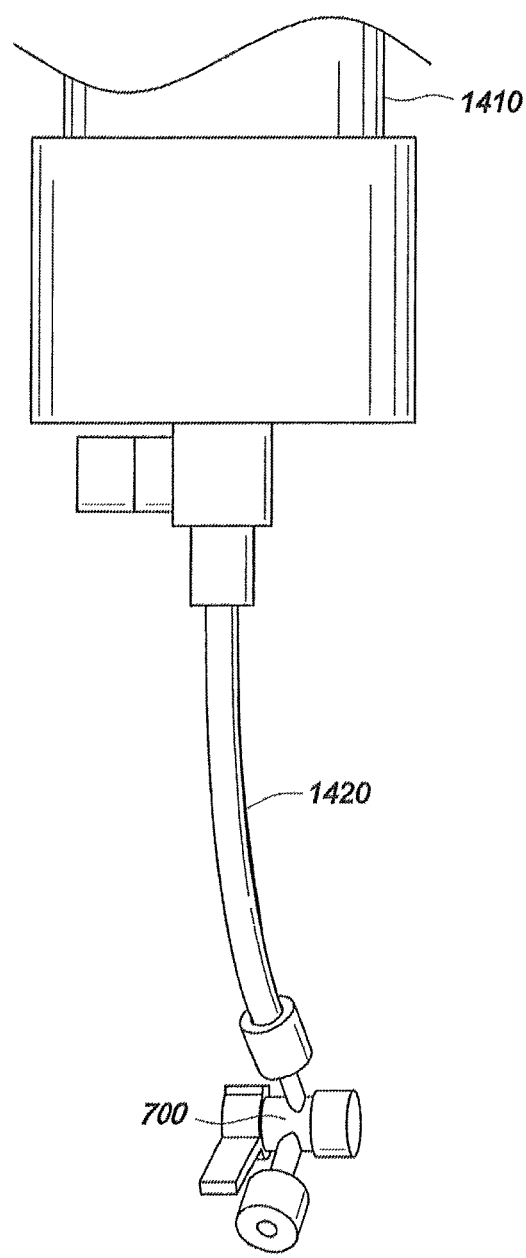
Figure 14C:
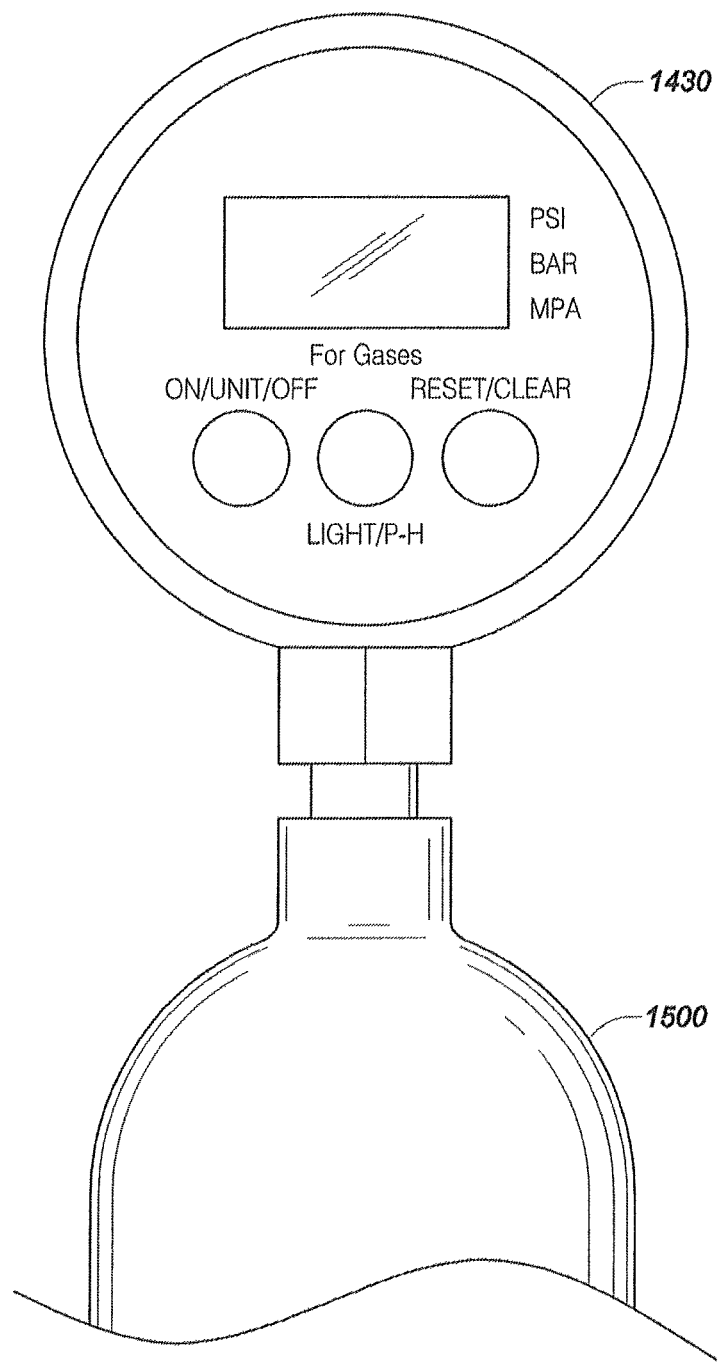
Figure 15:
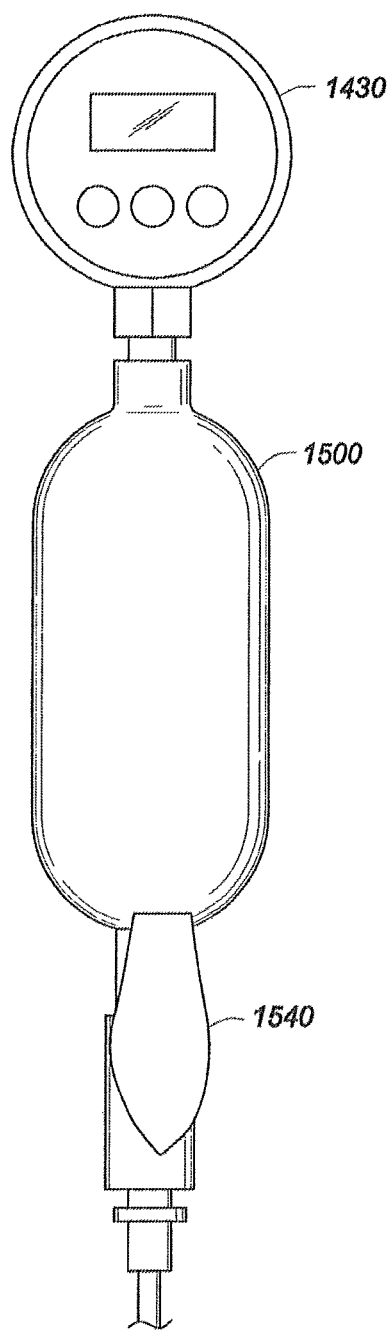
FIG. 15 depicts another inflation fluid container system 1400, in another embodiment, including a stainless steel inflation fluid container 1500 with a pressure gauge 1430 and a valve 1430.

The inflation fluid container is employed to control the amount or volume of fluid placed inside of the balloon. The inflation fluid container can be in the form of a canister made of, e.g., a polymeric material such as polyvinylchloride (PVC), tin coated steel, stainless steel, aluminum, aluminum alloy, brass, or other suitable material. The container can also be in syringe form. The materials employed are able to contain a fluid, preferably in gas form, e.g., compressed or non-compressed $N_2$, Ar, $O_2$, $CO_2$, or mixture(s) thereof, or compressed or non-compressed atmospheric air (a mixture of $N_2$, $O_2$, Ar, $CO_2$, Ne, $CH_4$, He, Kr, $H_2$, and Xe). The balloon composite wall materials and respective diffusion gradients and gas permeability characteristics are used to select a fluid for inflation of the intragastric balloon. The inflation fluid container materials are selected to ensure there is no diffusion or leakage of the fluid before it is connected to the connector or valve of the inflation catheter. The inflation fluid container system (FIGS. 14A-C) includes a connector (FIG. 14B) to the catheter and a pressure gauge (FIG. 14C). The inflation fluid container can be fabricated from any suitable material, e.g., stainless steel (FIG. 15). It can also contain a smart chip that notifies the healthcare professional of whether inflation is successful or if the balloon should be detached due to an error in the system.

Figure 16:
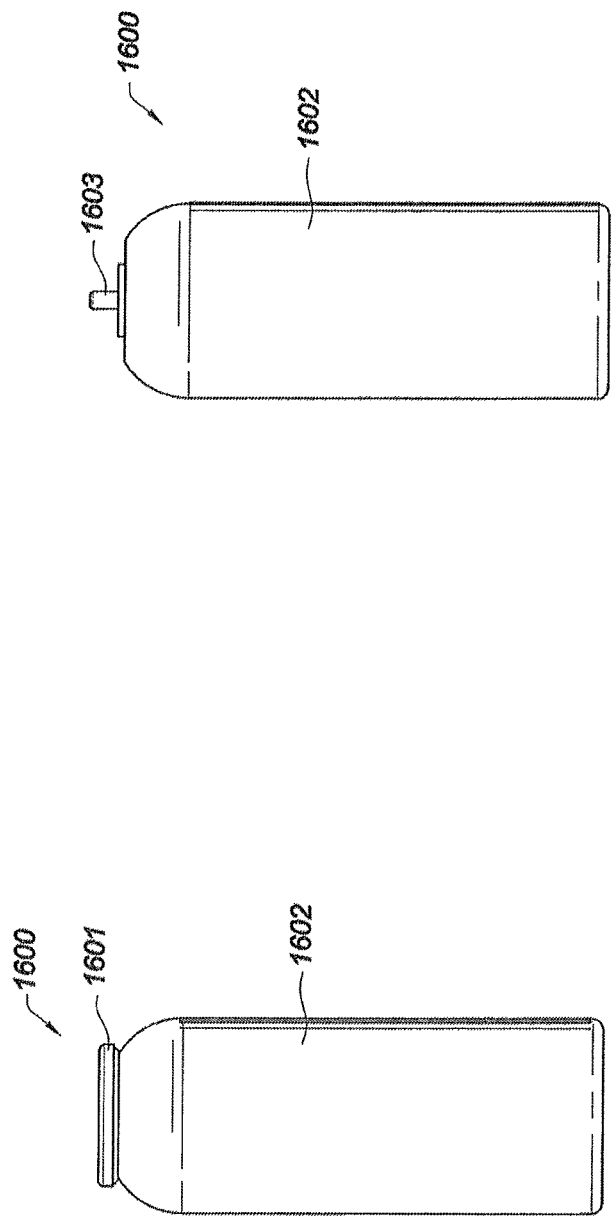
FIG. 16A depicts a disposable inflation fluid container 1600 in a closed configuration with a cap 1601 closing a fluid container 1602.
FIG. 16B depicts the disposable inflation fluid container 1600 of FIG. 16A in an opened configuration, wherein a straw 1603 extends upwardly from the fluid container 1602, for dispensing an inflation fluid within the container 1602.

In some embodiments, for example, in FIGS. 16A and 16B, the inflation fluid container is in the form of a canister or container (flexible or stiff-bodied), squeezable bag, compliant balloon-like tube or the like. As with other embodiments described above, the canister or container has walls formed of stainless steel, pure aluminum, aluminum alloy, brass, or other suitable barrier material. The walls surround and define an inner reservoir or cavity. The canister may include an actuator which enables a delivery system to be activated to provide the gas, a valve cup configured to retain valve components in an arrangement, a spring, a stem connecting the actuator and the spring, a stem gasket that seals the opening around the valve stem, a tube or straw which extends from the valve to the bottom of the can, allowing the gas under pressure to flow out of the canister, and a housing which holds the spring and connects the tube or straw to the valve assembly. An aperture is typically disposed within one of the walls, providing an opening into the inner reservoir. The canister includes a cap (FIG. 16A) configured to seal the aperture to prevent fluid from escaping the inner reservoir during storage. When the cap is removed, a straw is visible (FIG. 16B). A portion of the straw protrudes externally from the canister; the remainder of the straw extends through the aperture and into the inner reservoir. The straw may be formed of polypropylene, polyethylene, nylon, or other suitable polymeric material. The canister of some embodiments is configured to release an inflation fluid from the inner reservoir via the straw when a low pressure gradient fluid path is opened toward the balloon.

In some embodiments, it is desirable to inflate the intragastric balloon using an inflation fluid container having a known internal pressure or quantity of gas. For example, in some embodiments, it is desirable to begin with an inflation fluid container configured to have a volume of, e.g., 50 $cm^3$ or less to 400 $cm^3$ or more, or from 100 $cm^3$ to 200 $cm^3$ or 300 $cm^3$, or from 125 $cm^3$ to 175 $cm^3$, or approximately 150 $cm^3$. In other embodiments, other volumes of gas may be selected. In some embodiments, the inflation fluid container is filled at the site of the procedure, for example, by connecting the inflation fluid container to a tank of compressed gas prior to the procedure and filling the inflation fluid container until a desired volume or pressure is reached. The pressure can be monitored using a pressure gauge. In other embodiments, the inflation fluid container comes pre-filled with the desired amount of fluid. In such embodiments, a location's altitude (and resultant atmospheric pressure) should be taken into account in order to provide an inflation fluid container having the desired volume of gas. Inflation fluid containers may be designed with different sizes, colors, or other distinctive marking indicating the altitude range for which each is tailored.

To maintain "swallowability" of the balloon and to ensure comfort of the patient during the procedure, it is preferred to minimize the amount of time the catheter is placed in the mouth/esophagus. Timing of inflation can be selected so as to minimize time in place. The outer container-catheter assembly, once swallowed, takes approximately 3 to 120 seconds to reach the stomach. Once in the stomach, the inflation fluid container can be attached to a valve or port of the catheter system. Inflation timing can be controlled by selecting the length of catheter, diameter of the catheter tube, the starting temperature, and the starting pressure. Using the Ideal Gas Law for nitrogen and Boyle's Law ($P_1V_1=P_2V_2$) the amount of starting volume/pressure can be derived, where starting pressure takes into account the final target pressure at body temperature. It is desired to have an inflation time after swallow of less than 5 minutes, and preferably 2-3 minutes, before balloon detachment and catheter withdrawal. The inputs use to derive inflation of the balloon (preferably in less than 3 minutes) include inflation container volume, type of inflation fluid (preferably a compressed gas or compressed gas mixture), starting pressure, catheter length and diameter, and desired end volume and pressure of the balloon. Thus, due to differences in diameter, a smaller 1 French or 2 French diameter catheter system requires a lower starting pressure to achieve the same target balloon volume and pressure in the same time frame as a larger 4 or 5 French diameter catheter, assuming use of the same compressed gas formulation. In general, it is understood that starting with a lower pressure with the same flow rate/volume can increase the inflation time.

Figure 17:
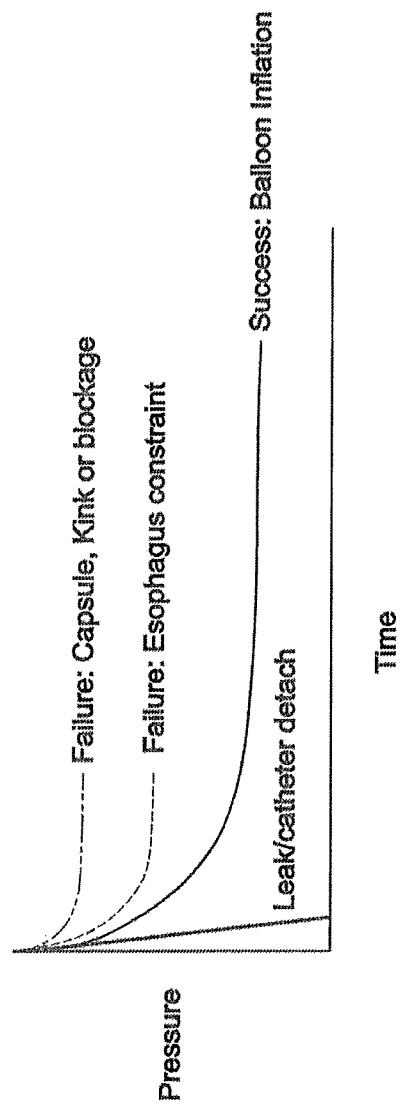
FIG. 17 is a graph depicting pressure as a function of time (pressure decay), obtained from feedback from an inflation source container.

The inflation source container can provide feedback to the end user based on a pressure decay system. Where there is an expected starting pressure and expected ending pressure to indicate whether the balloon is inflated properly, there is no need for endoscopic visualization (see FIG. 17). Each scenario of expected pressure outputs depicted in FIG. 17 can have its own tolerances around it to reduce possibilities of false positives, and the inflation fluid container can provide feedback based on these tolerances as to the status of balloon inflation and detachment. The inflation container contains additional low volume bolus of pressure that is released to determine device location and then is followed by a second, larger bolus intended to inflate the balloon. The gas release could be done in 1, 2, 3 or a plurality of boluses based on the events intended to be detected. This is derived based on the Ideal Gas Law, where there is an expected end pressure based on the fixed volume of the balloon. If the pressure remains high and doesn't decay as expected, this can indicate a failure in the system (e.g., the balloon container did not dissolve, the balloon is expanding in the esophagus because there is, e.g., a kink in the tube or other failure in the catheter system).

For example, for a successful decay using nitrogen only as the inflation fluid, the starting pressure is 22-30 PSI to inflate a balloon to 250 $cm^3$ and 1-2.5 psi (0.120 $kg/cm^2$) for a nylon-based material. To indicate successful balloon inflation, a math chip can be added to the inflation source container that provides at least one of a visual, audible, or tactile notification, or otherwise transmits a notification to a healthcare professional or administrator of whether inflation is successful or if there is an error in the system based on the pressure curve and a set of predetermined pressure tolerances and expected timing of inflation.

Figure 18:
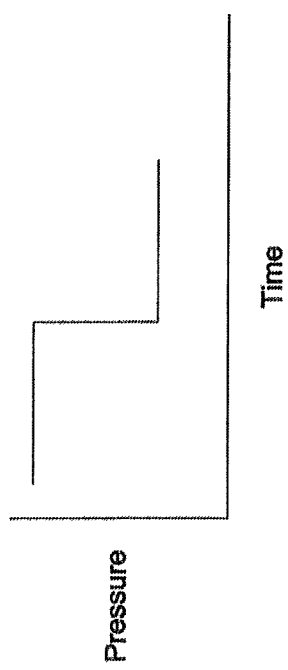
FIG. 18 depicts the expected decay curve for pressure sources using a spring mechanism or a balloon-within-balloon mechanism.

Alternatively, the balloon can be filled based on a starting pressure by using a spring mechanism, a balloon-within-balloon mechanism, or other pressure source. These mechanisms can potentially result in more predictable/consistent pressure decay curves, and again can have accompanying, predetermined tolerances for feedback back to the end user. FIG. 18 depicts the expected decay curve for these methods of pressure sources, and again would have accompanying, predetermined tolerances for feedback back to the end user.

Inflation Fluid Dispenser

Figure 19A:
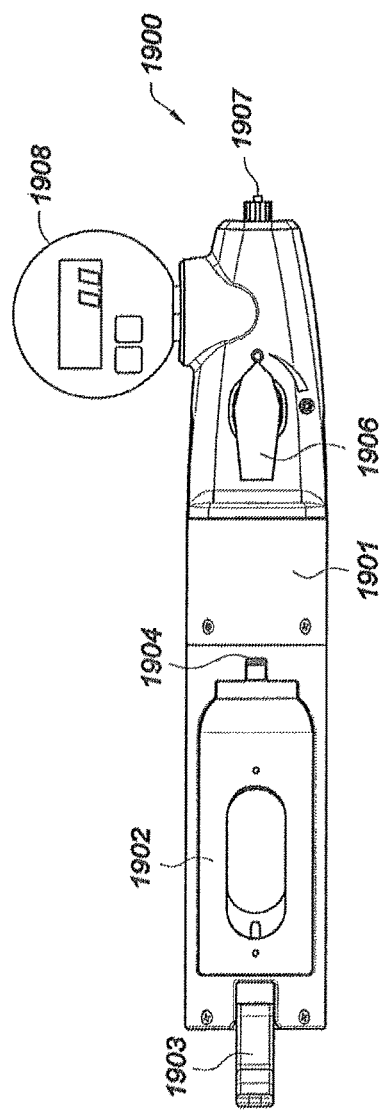
FIG. 19A is a front view of an inflation fluid dispenser 1900, in another embodiment, including a housing 1901 with a receiving space 1902 sized and shaped for receiving therein a disposable inflation fluid container 1600, such as shown in FIGS. 16A-B, a securement latch 1903 for securing the disposable inflation fluid container 1600 within the receiving space 1902, a proximal gas inlet with a spring 1904 for engaging the straw 1604 of the disposable inflation fluid container 1600, a lever or valve 1906, a distal outlet port 1907 and a pressure gauge 1908.
Figure 19B:
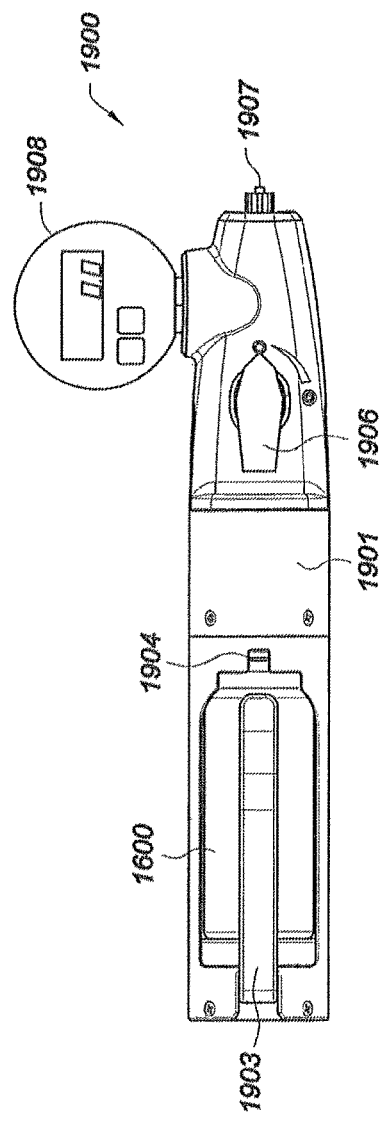
FIG. 19B depicts the inflation fluid dispenser 1900 of FIG. 19A with a disposable inflation fluid container 1600 received in the receiving space 1902 and the securement latch 1903 engaged so as to secure the disposable inflation fluid container 1600 within the receiving space 1902.

In some embodiments, a canister, such as the canister of FIGS. 16A and 16B, is coupled to an inflation fluid dispenser in order to deliver an inflation fluid to the intragastric balloon or other inflatable intragastric device. One such inflation fluid dispenser is shown in FIGS. 19A and 19B. The inflation fluid dispenser includes a housing configured to couple to the canister. Some embodiments have a securement latch, a receiving space fitted to receive a canister, a threaded engagement feature, and/or other features configured to securely couple the housing to the aerosol canister.

The housing may also include a spring positioned to contact the straw of the aerosol canister when the aerosol canister is in its secured position within the housing. In such embodiments, as the canister is brought into the secured position, the spring applies a force onto the straw in the direction of the canister, causing a preliminary quantity of inflation fluid to be released from the canister. In some embodiments, the release of a preliminary quantity of inflation fluid is designed to lower the inflation fluid within the aerosol canister to a desired starting volume or pressure. In some embodiments, the material, size, and strength of the spring are selected such that the amount of force exerted by the spring, and the resultant preliminary quantity of inflation fluid released, are predetermined. The material, size, and strength of the spring can be selected according to the elevation and average atmospheric pressure of the location in which the inflation fluid dispenser will be used. In this manner, the inflation fluid dispenser can be calibrated for use in particular regions or elevation ranges, and a canister of a standard size and fill volume can be used regardless of location.

The housing may also have an inner wall defining a channel, which extends at least partially through the housing. In such embodiments, a proximal inlet of the channel is positioned around the straw of the canister when the canister is securely coupled to the housing. The spring, if present, may be disposed within the proximal inlet. A distal outlet of the channel is positioned at a distal end of the inflation fluid dispenser and is configured as a port to which a catheter or other flexible tubing can be connected. In various embodiments, a valve is disposed in the channel between the proximal inlet and distal outlet and is configured to transition between a closed position and an open position. In the closed position, the valve blocks the flow of fluid between the proximal inlet and the distal outlet. In the open position, the flow of fluid is not blocked. Accordingly, in the open position, an inflation fluid can flow from an inner reservoir of the aerosol canister, through the straw of the canister and the channel of the inflation fluid dispenser, and out the distal outlet to a catheter, intragastric device, and/or other component coupled to the port.

In some embodiments, the inflation fluid dispenser includes a lever disposed on an outer surface of the housing and mechanically coupled to the valve. A medical professional can move the lever between a first and a second position to transition the valve between the open and closed positions. In other embodiments, the inflation fluid dispenser may include a button, key, toggle, or switch disposed on an outer surface of the housing and electrically coupled to the valve. When manipulated by a medical professional, the button, key, toggle, or switch may send an electrical signal to the valve to open or close. In still other embodiments, any suitable valve control mechanism configured for manipulation by a user may be present in the inflation fluid dispenser.

In some embodiments, a pressure gauge is coupled to the housing and configured to detect the gauge pressure within the channel between the valve and the distal outlet. In some such embodiments, the pressure gauge includes a digital display; in other embodiments, the pressure gauge has a card and mechanical dial indicator.

Figure 20:
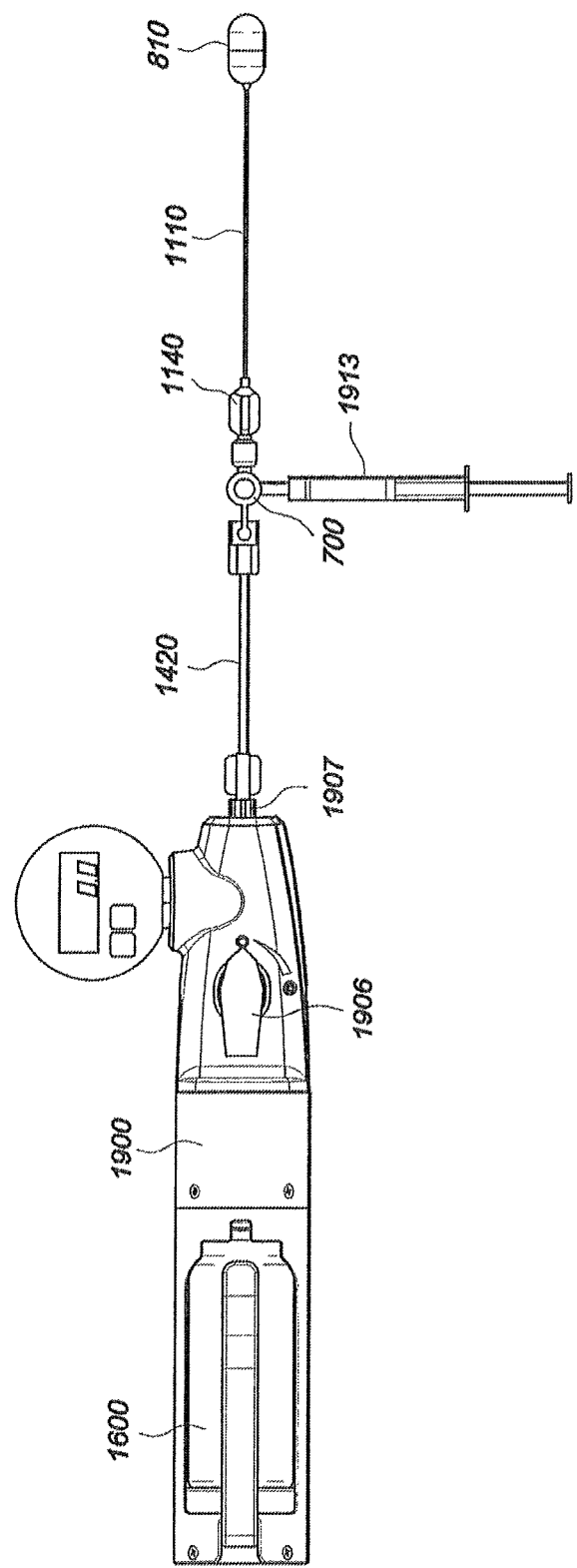
FIG. 20 depicts an inflation system 2000 for inflating a gastric balloon (not shown) including an inflation fluid container 1600, an inflation fluid dispenser 1900, an extension tube 1420, a valve 700, an inflation catheter 1110, a syringe 1913, and a capsule 810 encasing a balloon (not shown).

In some embodiments, the inflation fluid dispenser and canister (or other inflation fluid container) form part of a larger inflation system used to deliver the inflation fluid to the inflatable intragastric device. One example of an inflation system is provided in FIG. 20. In some such embodiments, flexible tubing and a substantially encapsulated intragastric device are coupled to the inflation fluid dispenser and inflation fluid container. The flexible tubing may include a catheter, a synthetic rubber extension tube, or other bendable, elongated device having an inner lumen. In some embodiments, the flexible tubing includes both an extension tube and a catheter connected via spokes of a stopcock having a three-way valve. A syringe may be connected to a third spoke of the three-way valve. Each of these components of the system is described in detail above.

In one method of delivering an inflatable intragastric device into a patient's stomach, the inflation fluid dispenser is first coupled to the inflation fluid container. In some embodiments, this coupling is performed with the dispenser's valve in an open position. The inflation fluid dispenser may contain a barometric pressure compensation valve that accounts for temperature, altitude, starting pressure; where based on the current altitude settings adjusts for the final starting gas number of moles required to inflate a balloon to its target pressure (constant, but can range from 1-5 psi). This compensation is done at coupling and may cause a preliminary amount of inflation fluid to be vented from the distal outlet of the channel when the inflation fluid container comes into contact with, and experiences a force from, a spring positioned in the proximal inlet of the channel based on differences in the environment of the manufacturing settings and the current environment the device is being utilized in (e.g., altitude). In some embodiments having a pressure gauge, when the valve is open, the pressure of the inflation fluid container can be monitored. In some embodiments, it is desired for inflation fluid to be vented from the inflation fluid container until the pressure within the container reaches 250 kPa, 300 kPa, or any value therebetween. In other embodiments, the desired pressure within the inflation fluid container is between 257 and 297 kPa, inclusive of said values. Once the inflation fluid container is securely coupled to the dispenser and the desired pressure has been reached, the valve may be closed.

In some embodiments, the extension tube, stopcock, catheter, syringe, and the at least partially encapsulated intragastric device are attached to each other, and a proximal end of the extension tube is attached to the port on the distal end of the dispenser. With the three-way valve of the stopcock in a position which allows for fluid connection between the extension tube and the catheter, fluid will flow between the channel of the dispenser (downstream from the dispenser's valve), the extension tube, the catheter, and the encapsulated intragastric device until an equilibrium is reached. The reading of the pressure gauge should be generally reflective of the pressure within the intragastric device.

In some methods of delivering the inflatable intragastric device into a patient's stomach, the patient swallows the substantially encapsulated intragastric device in order to deliver it to the stomach. In various embodiments, the catheter remains connected to the intragastric device and extends from the stomach, through the esophagus, and at least into the patient's mouth. In some embodiments, the swallowing and positioning of the intragastric device is monitored using a radiographic imaging method, such as, for example, fluoroscopy.

Once in the stomach, the capsule surrounding the intragastric device of various embodiments begins to dissolve. In some embodiments, the capsule dissolves in less than ten minutes. In some embodiments, the capsule dissolves within thirty seconds to four minutes. In some embodiments, the detected pressure will drop to below 10 kPa when the capsule dissolves. In some embodiments, the detected pressure will drop below 7 kPa upon dissolution. In various embodiments, the process of filling the inflatable intragastric device can begin upon dissolution of the capsule. In order to fill the inflatable intragastric device with an inflation fluid, the valve of the dispenser is transitioned to an open position. Inflation fluid will flow substantially from the relatively high-pressured inner reservoir of the inflation fluid container to the relatively low-pressured inner cavity of the inflatable intragastric device until an equilibrium pressure is achieved in the system. In some embodiments, approximately 150 cm$^3$ of a gas in unconstrained atmosphere that is constrained to 28 psi or approximately 450 cc at atmospheric pressure. For example, $N_2$, will be transferred into the intragastric device. In some embodiments, the intragastric device will achieve a final volume within the stomach of approximately 250 cc. In other embodiments, the intragastric device will achieve a final volume within the stomach of 50 to 400 cc, and preferably 90 to 300 cc, or any individual value or range therebetween. The intragastric device of some embodiments will achieve a final pressure of 5 kPa, 20 kPa, or any value therebetween. In a preferred embodiment, the final pressure within the intragastric device is between 8.3 kPa and 17.2 kPa, and more preferably, the final pressure of the intragastric device is 13.8 kPa. The intragastric device of some embodiments reaches a desired final pressure in less than five minutes. In some embodiments, the final pressure is reached in approximately two minutes.

In some embodiments of the method, once the pressure of the system has stabilized and reached an equilibrium, the catheter can be separated from the intragastric device and removed from the patient. In some embodiments, the syringe is used to separate the catheter from the intragastric device. The three-way valve is moved into a position in which the syringe is in fluid connection with the catheter and intragastric device. The syringe's plunger is pushed rapidly to expel a fluid from the syringe into the inner cavity of the balloon at a force sufficient to dislodge the catheter from the intragastric device (as described in more detail above).

Composite Wall

The materials selected for the composite wall of the balloon may be optimized to maintain the original inflation gas without significant diffusion, or may also allow for diffusion of the gases located in the gastric environment, e.g., $CO_2$, $O_2$, argon, or $N_2$ to diffuse through the wall of the balloon to inflate, partially or wholly, once the balloon is placed in the stomach. A fluid (a liquid or gas) can also be added inside of the balloon using the inflation catheter(s) described herein to change diffusion direction of the balloon composite wall and when it reaches stasis based on the internal and external environment.

A gastric balloon inflated by nitrogen, $CO_2$ gas, a single fluid (gas) or a mixture of gasses employs a composite wall that provides barrier properties (fluid retention), properties imparting resistance to pH and moisture conditions in the gastric environment or the environment within the central lumen of the balloon, and structural properties to resist gastric motility forces, abrasion of the balloon wall in vivo, and damage during manufacturing and folding of the balloon. Certain materials employed in the balloon materials are able to withstand a hostile gastric environment designed to break down foreign objects (e.g., food particles). Some of the variables that the gastric environment encompasses are as follows: gastric liquid pH of from 1.5-5; temperature of approx. 37° C.; a relative humidity of 90-100%; ingress of gastric space gas content; and constant gastric motility external pressures of from 0-4 psi at variable frequencies and cycle times based on the fed state of the stomach. The external pressure imparted by gastric motility can also cause abrasions on the surface of the balloon. The inside of the balloon lumen may contain moisture from a solution injected in the balloon for timing of auto-deflation or any moisture that has transferred across the membrane due to the external humid environment. In addition to these environmental stresses the wall materials meet biocompatibility requirements and are constructed such that the total thickness of the wall (barrier material) is thin enough to be compacted and placed inside of a swallowable-sized container ("outer container") without significant damage or lodging. The outer container is small enough to transcend the esophagus (which has a diameter of approximately 2.5 cm). The wall or barrier material is also heat formable and sealable for balloon construct and maintains a bond strength that can contain internal gas pressures of up to 10 psi generated by the initial inflation pressure as well as pressure due to the ingress of gas molecules from the stomach cavity until the system's gas environment reaches stasis. The film properties that are evaluated to determine suitability for use in the composite wall of the balloon include pH resistance, water vapor transmission rate, gas barrier properties, mechanical strength/abrasion properties, temperature resistance, formability, flex-crack (Gelbo) resistance, surface energy (wettability) compliance, and heat bond potential.

The various layers in the composite wall can impart one or more desirable properties to the balloon (e.g., fluid retention, resistance to moisture, resistance to acidic environment, wettability for processing, and structural strength). A list of polymer resins and coatings that can be combined into a multi-layer preformed system ("composite wall") is provided in Tables 1a-b. These films can be adhesively bonded together, co-extruded, or adhered via tie layers or a combination thereof to obtain the desired combination of properties for the composite wall, as discussed below. The materials identified as film coatings in Tables 1a-b are provided as coatings applied to a base polymer film, e.g., PET, Nylon, or other structural layer.

TABLE 1a

Film Resins

| | Characteristics | | |
|---|---|---|---|
| | Good Structural/ Behavior/ Mechanical Strength/ Compliance | Good Fluid Retention Barrier Properties | Good Manufacturability/ Surface Energy Properties |
| FILM RESINS | | | |
| Polyethylene Terephthalate (PET) Polytrimethylene Terephthalate (PTT) | X | X | |
| Liquid Crystal Polymer (LCP) | X | X | |
| Polytrimethylene naphthalate (PTN) | X | X | |
| Polyethylene naphthalate (PEN) | X | X | |
| Polyimide (PI) | X | X | |
| Linear Low Density Polyethylene (LLDPE) | | | X |
| Ethylene Vinyl Alcohol (EVOH) | | X | |
| Polyamide: Nylon (PA) and Nylon-6 (PAG)/Nylon 12 | | X | X |
| High Density Polyethylene (HDPE) | | | X |
| Polypropylene (PP) | | | X |
| Polyurethane | | | X |
| PVDC (Saran) | | X | X |
| Polyether Block Amide (Pebax) | | | X |
| Polyvinyl Alcohol (PVOH) | | X | |
| Silicone | X | | X |

TABLE 1b

Film Coatings

| | Characteristics | | |
|---|---|---|---|
| | Good Structural/ Behavior/ Mechanical Strength/ Compliance | Good Fluid Retention Barrier Properties | Good Manufacturability/ Surface Energy Properties |
| FILM COATINGS | | | |
| Silicon Dioxide (SiO2) | | X | |
| Aluminum Oxide (Al₂O₃) | | X | |
| Nanopolymers (Nano/Clay) | | X | |
| External Organic Coatings (e.g., epoxy amine) | | X | |
| Inorganic Coatings (e.g., Amorphous Carbon) | | X | |
| Oxygen Scavengers | | X | |
| Parylene C | | X | |

Fluid Retention Layers

In preferred embodiments, a blended polymer resin using multiple layers is employed to maintain the inflated balloon's shape and volume by retaining the inflation fluid for the duration of the intended use. Certain barrier films, widely used in the food packaging and plastic bottling industries, can advantageously be employed for this purpose in the composite wall of the balloon. Preferably, the barrier materials have a low permeability to carbon dioxide (or other gases, liquids, or fluids that are alternatively or additionally used to inflate the volume-occupying subcomponent). These barrier layers preferably have good adherence to the base material. Preferred barrier coating materials and films include polyethylene terephthalate (PET), linear low density polyethylene (LLDPE), ethylene vinyl alcohol (EVOH), polyamides such as Nylon (PA) and Nylon-6 (PA-6), polyimide (PI), liquid crystal polymer (LCP), high density polyethylene (HDPE), polypropylene (PP), biocompatible poly(hydroxyamino ethers), polyethylene naphthalate, polyvinylidene chloride (PVDC), saran, ethylene vinyl alcohol copolymers, polyvinyl acetate, silicon oxide (SiOx), silicon dioxide ($SiO_2$), aluminum oxide ($Al_2O_3$), polyvinyl alcohol (PVOH), nanopolymers (e.g., nanoclay), polyimide thermoset film, EVALCA EVAL EF-XL, Hostaphan GN, Hostaphan RHBY, RHB MI, Techbarrier HX (SiOx-coated PET), Triad Silver (silver metallized PET), Oxyshield 2454, Bicor 84 AOH, acrylonitrile copolymers, and copolymers of terephthalic acid and isophthalic acid with ethylene glycol and at least one diol. Alternative gas-barrier materials include polyamine-polyepoxides. These materials are typically provided as a solvent-based or aqueous-based thermosetting composition and are typically spray-coated onto a preform and then heat-cured to form the finished barrier coating. Alternative gas barrier materials that can be applied as coatings to the volume-occupying subcomponent include metals such as silver or aluminum. Other materials that may be used to improve the gas impermeability of the volume occupying subcomponent include, but are not limited to, gold or any noble metal, PET coated with saran, and conformal coatings.

One method that is used in the packaging industry to delay diffusion of the inflation fluid is to thicken the material. Thickening the material is generally not preferred, as the total composite wall thickness preferably does not exceed 0.004 inches (0.010 cm) in order for the balloon to be foldable into the desired delivery container size for swallowing by a patient.

A multilayer polymer film that is able to withstand the gastric environment over the course of the usable life of the balloon includes linear low density polyethylene (LLDPE) adhesively bonded to a Nylon 12 film. Alternatively, an additional film layer with barrier properties, such as PVDC can be added to the composite wall.

The layers providing gas barrier properties are preferably situated as inner layers in the composite wall as they are less mechanically robust than resins that are considered "structural" such as Nylon and the like.

Structural Layers

Layers such as polyurethane, Nylon, or polyethylene terephthalate (PET) can be added to the composite wall for structural purposes, and are preferably placed as outermost (proximal to the gastric environment or proximal to the central lumen of the balloon) layers, provided that the pH resistance of such layers can withstand the acidic environment of the stomach or the central lumen of the balloon.

Fabrication of the Composite Wall

The various layers of the composite wall, including the gas barrier layers, need not be situated in any particular order, but those of superior resistance to acidity, temperature, mechanical abrasion, and superior biocompatibility profile are preferably employed as layers contacting the gastric environment. Those with superior resistance to, e.g., acidity and temperature, are preferably employed as layers contacting the central lumen of the balloon.

The various layers of the wall can include a single layer or up to 10 or more different monolayers; however, a film thickness of from 0.001 inches (0.0254 cm) to 0.004 inches (0.010 cm) thick is desirable such that the resulting balloon compacted to fit into a swallowable capsule. The resulting composite wall preferably has good performance specifications with respect to each category listed in Tables 1a-b.

Films that are co-extruded are advantageously employed, as some adhesives may contain leachables that are undesirable from a biocompatibility perspective. In addition, coextrusion allows for better blending such that the materials maintain their original properties when combined in this fashion and are less likely to be subject to delamination when exposed to gastric motility forces.

Combining films with similar properties, e.g., two film layers with excellent gas barrier properties, in a composite wall is advantageous for use in a gastric balloon containing nitrogen, oxygen, $CO_2$ or a mixture thereof as the inflation gas or where the external environment the product is to be placed in, contains a mixture of gases including $CO_2$, e.g., the stomach. A primary advantage of such composite films is that restrictions on film thickness can be observed without sacrifice of gas barrier properties. Such a configuration also contributes to reducing the effects of processing damage (e.g., manufacturing and compacting) and damage due to exposure to in vivo conditions (e.g., gastric motility forces).

In a particularly preferred embodiment, the composite wall includes a plurality of layers. The first layer is an outer protective layer that is configured for exposure to the gastric environment. This layer is resistant to mechanical forces, exposure to water (vapor), abrasion, and high acidity levels. Nylon or more specifically, Nylon 12 is particularly preferred for the layer exposed to the gastric environment, and is especially resistant to mechanical forces.

In an alternative embodiment, polyurethane is RF welded to saran to yield a 6-7 mil thick composite wall. In another embodiment, a five layer system is provided comprising a layer of saran sandwiched between two polyurethane layers. Between the saran layer and each of the polyurethane layers is a tie layer. The layers can be welded together, co-extruded or adhered using an adhesive. This tri-layer is then co-extruded to Nylon on each side, and then a final sealing layer (polyethylene or the like) is added to one of the nylon layers for the total composite wall. A representative example of material combinations that are commercially available or manufacturable is provided in Table 2. The orientation of the layers (innermost—in contact with the central balloon lumen, or outermost—in contact with the gastric environment) is also indicated if more than two layers are described to support a suggested composite wall.

Most of the film resins listed in Table 2 provide some degree of gas barrier properties. Therefore, many can be used solely to form the balloon wall as a monolayer film; however they can also be used in conjunction with other film resins to meet the desired gas retention and mechanical specifications for the useful life of the balloon based on the inflation gas and external environment the balloon is to be placed in. These film resins can also be coated with gas barrier coatings listed in Tables 1a-b. Additional film layers can be added to form the total composite wall. While such additional layers may not impart substantial barrier properties, they can provide structural and/or mechanical properties, protection for the other layers of the composite wall that are susceptible to water vapor, humidity, pH, or the like, or other desirable properties. The film layers can be assembled using various adhesives, via co-extrusion, via lamination, and/or using tie layers and such to create a composite wall that meets the requirements of an intragastric balloon suitable for use for at least 25 days, or up to 90 days or more, with the specified gas retention properties. Table 2 provides a list of layers and layer combinations suitable for use in composite walls for an intragastric balloon. The composite description, resin abbreviation, configuration (single layer, bilayer, trilayer, or the like) and trade name of commercially available combinations are listed. The number of layers indicated does not include any adhesive layers or tie layers used to fabricate the composite wall, such that a 6-layer composite wall may, for example, have two or three adhesive layers and/or tie layers that make up the total composite wall, and therefore the total number of layers can be eight or nine in final form. The term "layer" as used herein is a broad term, and is to be given its ordinary and customary meaning to a person of ordinary skill in the art (and is not to be limited to a special or customized meaning), and refers without limitation to a single thickness of a homogenous substance (e.g., a coating such as SiOx, or a layer such as PET), as well as to a supporting layer having a coating thereon (wherein a "coating" is, e.g., a material typically employed in conjunction with substrate that provides structural support to the coating layer). For example, a PET-SiOx "layer" is referred to herein, wherein a layer of Si-Ox is provided on a supporting PET layer.

TABLE 2

| Example Film Composite Walls* | Abbreviation | Trade name |
|---|---|---|
| polyethylene terephthalate | PET | Mylar |
| metallized oriented polyethylene terephthalate | metallized OPET | Custom |
| polyvinyl alcohol coated oriented polypropylene | PVOH coated OPP | Bicor |
| metallized biaxially oriented nylon 6 | metallized OPA6 | Custom |
| Biaxally oriented Nylon/ethylene vinyl alcohol/biaxally oriented Nylon | OPA/EVOH/OPA | Honeywell Oxyshield Plus |
| Nylon/ethylene vinyl alcohol/Low Density Polyethylene | Nylon/EVOH/LDPE | Custom |
| polyvinylidene chloride coated oriented polyethylene terephthalate | PVDC/OPET | Mylar |
| polyvinylidene chloride coated oriented polypropylene | PVCD/OPP | Custom |
| polyvinylidene chloride coated biaxally oriented Nylon 6 | PVCD/OPA6 | Honeywell Oxyshield |

TABLE 2-continued

| Example Film Composite Walls* | Abbreviation | Trade name |
|---|---|---|
| high density polyethylene/ethylene vinyl alcohol | HDPE/EVOH | Custom |
| polypropylene/ethylene vinyl alcohol laminate | PP/EVOH | Custom |
| polyethylene terephthalate/ethylene vinyl alcohol | PET/EVOH | Custom |
| metallized oriented polypropylene | metallized OPP | Custom |
| sealable PVDC coated oriented polypropylene | PVDC coated PP | Custom |
| polyvinylidene fluoride | PVDF | Custom |
| Polyvinyl chloride | PVC | Custom |
| polyvinyl fluoride | PVF | Tedlar |
| polychlorofluoroethylene | PCTFE | ACLAR UltRx, SupRx, Rx |
| amine-based epoxy coated Nylon | epoxy coated PA6 | Bairocade |
| polyvinyl chloride-polyvinylidene chloride copolymer | PVC-PVDC | Custom |
| medium density polyethylene | MDPE | Custom |
| Nylon/Polypropylene | Nylon/PP laminate | Custom |
| Nylon-High Density Polyethylene | Nylon-HDPE laminate | Custom |
| Nylon 12/Ethyl Methyl Acrylate/Polyvinylidene Chloride/Ethyl Methyl Acrylate/Nylon 12/Linear Low Density Polyethylene + Low Density Polyethylene | Co-extruded Nylon 12-encapsulated PVDC-Nylon 12-LLDPE + LDPE | Custom Co-extruded blend |
| Multi-layer Nylon 12/Linear Low Density Polyethylene + Low Density Polyethylene | Co-extruded multi-layer Nylon 12-LLDPE + LDPE | Custom Co-Extruded Blend |
| acetylene plasma coating on polyester | PET/A | Custom |
| difluoroethylene coating on polyethylene terephthalate | PET/DA | Custom |
| oriented polypropylene | OPP | Custom |
| cast propylene | CPP | Custom |
| high density polyethylene | HDPE | Custom |
| cyclic olefin copolymer | COC | Custom |
| oriented polystyrene | OPS | Custom |
| Fluorinated Ethylene Propylene | FEP | Custom |
| difluoroethylene coating on low density polyethylene | LDPE/D | Custom |
| difluoroethylene coating on polypropylene | PP/D | Custom |
| acetylene plasma coating on polypropylene | PP/A | Custom |
| acetylene plasma coating on low density polyethylene | LDPE/A | Custom |
| polybutylene terephthalate polyether glycol copolymer | TPC-ET | Hytrel |
| polyether block amide TPE | PEBA | Pebax |
| oxide coated biaxally oriented Nylon | oxide coated PA | Honeywell Oxyshield Ultra |
| Nanoclay/nylon | MXD6/Nanoclay | Imperm/Aegis OXCE |
| Polyethylene Terephthalate/Silicone Dioxide | PET/SiOx | BestPET/TechBarrier |
| Polyethylene Terephthalate/Oxygen scavengers | PET + 02 Scavengers | MonoxBar |
| Modified Polyethylene Terephthalate | Modified PET | DiamondClear |
| Polyethylene Terephthalate/Nylon 6 | PET/MXD6 | HP867 |
| Amorphous polyvinyl alcohol | Amorphous PVOH | Nichigo G-Polymer |
| Nylon 6/Ethyl vinyl alcohol/Linear Low Density Polyethylene | Nylon 6/EVOH/LLDPE | Custom |
| Ethyl vinyl alcohol/Poly-Propylene/Ethyl vinyl alcohol | EVOH/PP/EVOH | Custom |
| Ethyl vinyl alcohol/Nylon | EVOH/Nylon | Custom |
| Polyethylene/Ethyl vinyl alcohol/Polyethylene | PE/EVOH/PE | Custom |
| Polyethylene/Ethyl vinyl alcohol/Polyethylene Terephthalate | PE/EVOH/PET | Custom |

TABLE 2-continued

| Example Film Composite Walls* | Abbreviation | Trade name |
|---|---|---|
| Silicon dioxide-coated Polyethylene Terephthalate/Linear Low Density Polyethylene/Ethyl vinyl alcohol/Linear Low Density Polyethylene | PET-SiOx/LLDPE/EVOH/LLDPE | Custom |
| Aluminum Oxide-coated Polyethylene Terephthalate/Polyethylene | PET-Al$_2$O$_3$/LLDPE | Custom |
| Polyethylene/Ethyl vinyl alcohol/Linear Low Density Polyethylene | PE/EVOH/LLDPE | Custom |
| Polyethylene Terephthalate/Polyethylene/Polyethylene/Bi-axially oriented Ethyl vinyl alcohol | PET/PE/OEVOH/PE | Custom |
| Polyethylene Terephthalate/Polyethylene/Ethyl vinyl alcohol/Ethyl vinyl alcohol/Ethyl vinyl alcohol/Polyethylene | PET/PE/EVOH/EVOH/EVOH/PE | Custom |
| Polyethylene Terephthalate/Polyethylene/Nylon 6/Ethyl vinyl alcohol/Nylon 6/Polyethylene | PET/PE/Nylon 6/EVOH/Nylon 6/PE | Custom |
| Silicon dioxide-coated Polyethylene Terephthalate/Polyethylene/Ethyl vinyl alcohol/Polyethylene | PET-SiOx/PE/EVOH/PE | Custom |
| Polyethylene/Ethyl vinyl alcohol/polyvinylchloride | PE/EVOH/PVDC | Custom |
| Polyethylene Terephthalate/Linear Low Density Polyethylene/Ethyl vinyl alcohol/Linear Low Density Polyethylene | PET/LLDPE/EVOH/LLDPE | Custom |
| Kurrarister C-coated Polyethylene Terephthalate/Polyethylene/Ethyl vinyl alcohol/Polyethylene | PET-Kurrarister-C/PE/EVOH/PE | Custom |
| Polyethylene Terephthalate/Polyethylene/Nylon 6/Ethyl vinyl alcohol/Nylon 6/Polyethylene | PET/PE/Nylon 6/EVOH/Nylon 6/PE | Custom |
| Nylon 6/Ethyl vinyl alcohol/Polyvinylchloride/Low Density Polyethylene | Nylon 6/EVOH/PVDC/Nylon 6/LDPE | Custom |
| Polyimide | PI | Custom |
| Polyimide/Linear Low Density Polyethylene | PI/LLDPE | Custom |
| Polyimide/Polyvinylchloride | PI/PVdC | Custom |
| Polyimide/Polyvinylchloride/Linear Low Density Polyethylene | PI/PVdC/LLDPE | Custom |

In particularly preferred embodiments, the composite wall has a thickness of 0.005 inches or less (5.0 mil or less); however, in certain embodiments a thicker composite wall may be acceptable. Generally it is preferred that the composite wall have a thickness of no more than 0.004 inches (4.0 mil).

Fabrication of the Balloon

To ensure good mechanical strength of the balloon, the balloon is preferably formed and sealed such that the edges of the pieces used to form the balloon are overlapping. This can be accomplished by any suitable method. For example, two flat sheets of material can be placed in a frame with magnetized edges to hold the two sheets in place. Slack can be added to the piece of film to orient the material such that it maintains its properties after the forming process. The frame can be placed over a mold that represents a hemisphere the balloon. The material, with slack put in it prior to pressure being applied, re-orients the material such that it is more evenly distributed around the hemisphere shape. The material is preferably thickest in the middle and is made thinner on the sides where it will be welded to a second piece to create a sphere or ellipsoid having a substantially uniform wall thickness. For example, starting with a 0.0295" film, the middle of the film or subsequent apex has an ending film thickness of 0.0045" and the edges have an ending thickness of 0.0265" for subsequent overlapping during the welding process.

Figure 21A:
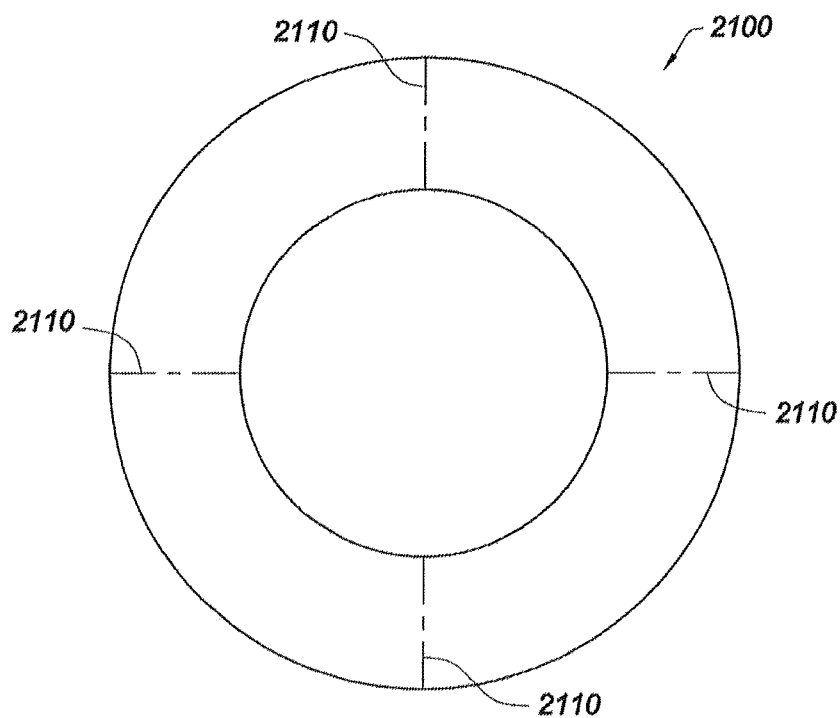
FIGS. 21A-B depict a top view (FIG. 21A) and side view (FIG. 21B) of an embodiment of a gastric balloon 2100, for use with an inflation system 2000 such as is shown in FIG. 20, showing the configuration of balloon seams 2110 for fabricating a balloon which resists bursting in vivo.
Figure 21B:
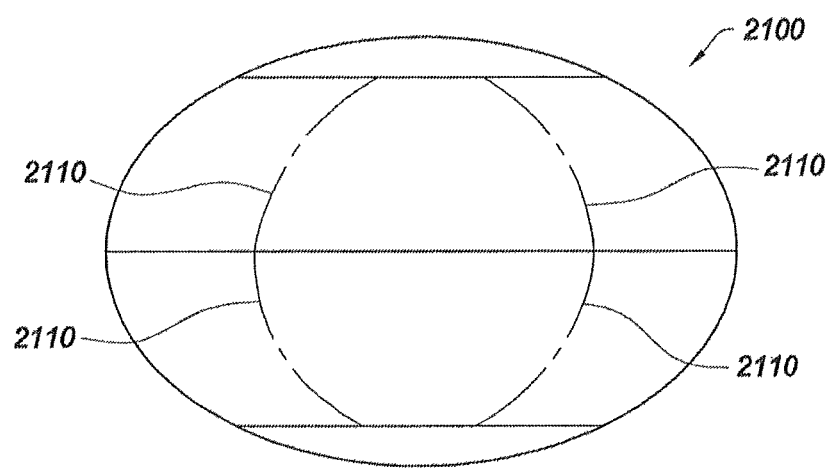

The valve can be adhered to the (e.g., polyethylene, PE) side of one of the hemispheres and protrude out of the opposite (e.g., nylon) side. One hemisphere typically consists of Nylon as the outermost layer and the second hemisphere typically has polyethylene (sealing web) as the outermost layer. The edges of the two hemispheres are preferably aligned such that they overlap by at least 1 mm and no more than 5 mm. Alignment and overlay of the two hemispheres is done to compensate for the thinning at the edges during the thermoforming process, which in turn inhibits seam bursts in vivo. Each half of the spheroid is placed on a fixture and the excess from the forming process is trimmed. On a multi-layer film, the sealing layer, a PE or similar layer is bonded to the sealing layer of the second film half. To do this the film of the hemisphere that has the nylon exposed to the external environment is folded up along the edges of the sphere on one half (see FIGS. 21A-B) such that it can be bonded to the hemisphere with the polyethylene on the outermost layer.

The two film pieces are then sealed using a roller bonder or a band heater. In the roller bonder, a pneumatic cylinder provides the compression, the heater provides the sealing heat, and a motor that moves the bonder around the area controls the time that is required to ensure proper sealing. In the band heater, there is a heating element, an expandable plug that provides the compression, and a timer. The band is a metal, preferably copper and a spool-like fixture provides the compression needed. Using film layers of different melt temperatures helps ensure integrity of the barrier layers of the final balloon configuration. If two similar materials are welded, then an insulator can be employed. In a preferred embodiment, one sphere is provided with the Nylon layer facing out and the second sphere has a PE layer facing out.

Balloons with Resistance to Spontaneous Deflation

The largest percentage of intragastric balloon malfunctions is due to spontaneous deflations. Spontaneous deflations can occur due to (1) external puncture of the intragastric balloon due to gastric motility forces, (2) over inflation of the balloon due to increased internal pressure of the balloon from uptake of the gastric environment of the gasses and water vapor and (3) under inflation of the balloon that leads to fatiguing of the excess material and subsequent puncture of the balloon. By managing these two variables and tuning these variables to withstand the dynamic gastric environment, the balloon system can be tailored to ensure it remains inflated throughout its useful life. Instances of spontaneous deflation in this intragastric balloon can be minimized by selection of the starting inflation gas in conjunction with selection of the composite wall materials and construction. Selection of the permeability characteristics with respect to water vapor transmission and gas permeability of the composite wall so as to take advantage of the properties of the gastric space contents can enable the rate of diffusion of gases into and out of the balloon to be controlled. This method allows for a tunable method for prevention of under inflation and over inflation.

Another phenomenon seen with gastric balloons and obesity in general is stomach accommodation. In the process of stomach accommodation, the stomach grows to accommodate the space occupying device or excess food that is ingested. In the process of stomach accommodation, the volume of a stomach containing an intragastric balloon grows over time, such that the patient becomes hungrier. However, by controlling gas diffusion and water vapor transmission across the balloon wall over time, the balloon size can also be increased over time by selecting the starting inflation gas(es) and water and other in vivo gas permeability characteristics of the film so as to maintain weight loss. In addition to spontaneous deflations, selecting the permeability characteristics of the composite wall in conjunction with the starting gases and utilizing the transfer of gases and water inside of the balloon from the gastric environment, the balloon can be designed to grow over its useful life in response to stomach accommodation.

Experiments were performed wherein various starting inflation gases were selected in conjunction with varying external gas environments that mimic the stomach gas and water environment in vivo. The stomach environment consists of water, acid (hydrochloric acid), a mixture of gases, and chyme (the semifluid mass of partly digested food expelled by the stomach into the duodenum). Stomach gas usually arises from swallowing air during eating. The composition of air is nitrogen ($N_2$) 78.084%; oxygen ($O_2$) 20.9476%; argon (Ar) 0.934%; carbon dioxide ($CO_2$) 0.0314%; neon (Ne) 0.001818%; methane ($CH_4$) 0.0002%; helium (He) 0.000524%; krypton (Kr) 0.000114%; hydrogen ($H_2$) 0.00005%; and xenon (Xe) 0.0000087%.

Five gases constitute greater than 99% of the gases in gastrointestinal system: $N_2$, $O_2$, $CO_2$, $H_2$ and methane, with nitrogen predominating. Gastric $pCO_2$ closely parallels local (splanchnic) arterial and draining venous blood $pCO_2$ values. Neutralization of stomach acid can also generate gas. For example, when the stomach acid reacts with bicarbonates (e.g., as are present in certain antacids) in the digestive juices, the chemical process creates $CO_2$, which is normally absorbed into the blood stream. Digestion of food in the intestines, mainly through fermentation by colonic bacteria, generates $CO_2$, $H_2$, and methane. Microbes appear to be the sole source of all of the hydrogen and methane produced in the intestine. These arise from fermentation and digestion of nutrients (polysaccharides from fruits and vegetables are not digested in the small intestines). Small quantities of a few other gases, including hydrogen sulfide, indoles, and ammonia can also be generated.

Controlled self-inflation of the intragastric balloon in the in vivo environment can be achieved by using a semi-permeable or permeable composite wall in the balloon and initially filling the balloon with a preselected single gas, such as $N_2$ or $O_2$. The balloon utilizes differences in concentrations of gases and water concentration differences between the internal balloon environment and the external environment in vivo (GI/stomach) to increase and/or decrease the volume and/or pressure over time. To achieve a controlled decrease in volume and/or pressure, a wall can be employed that has a relatively higher permeability to the single gas used to inflate the balloon than to other gases present in the in vivo gastrointestinal environment. For example, if nitrogen gas is employed as the inflation gas, over time in the in vivo environment, the volume and/or pressure in the balloon will decrease as nitrogen diffuses out into the in vivo environment through the oxygen permeable wall. Similarly, if oxygen gas is employed as the inflation gas, over time in the in vivo environment, the volume and/or pressure in the balloon will decrease as oxygen diffuses out into the in vivo environment through the oxygen permeable wall. The differential in partial pressure of the single gas in the balloon (higher) versus the in vivo environment (lower) will drive the process until equilibrium or homeostasis is reached. To achieve a controlled increase in volume and/or pressure, a wall can be employed that has a relatively lower permeability to the single gas used to inflate the balloon than to other gases present in the in vivo gastrointestinal environment. For example, if nitrogen gas is employed as the inflation gas, over time in the in vivo environment, the volume and/or pressure in the balloon will increase as $CO_2$, etc. diffuses into the balloon through the $CO_2$ permeable wall. The differential in partial pressure of the permeable gas in the balloon (lower) versus the in vivo environment (higher) will drive the process until equilibrium is reached.

In addition, maintaining and/or controlling inflation of the balloon can also be done using the differences in concentrations between the internal balloon environment and external gastric environment in which the balloon volume/pressure can be increased or decreased as needed to extend the useful life of the product. One reason to decrease the pressure can be to first inflate the balloon with a large, but highly diffusible/soluble gas molecule such as $CO_2$ in addition to a more inert gas like nitrogen to pre-stretch the balloon, with the soluble gas diffusing out of the balloon and other gases not originally present in the balloon migrating in to fill the balloon.

Inflation gases can be selected to start with the majority of the gas in the balloon comprising a large, inert gas or a gas that has low diffusivity through the selected composite wall. An inert gas in conjunction with a less inert gas(es) that are more soluble in the gastric environment, can be combined to comprise the starting balloon inflation gas composition. Patient diet and medications can also affect/control balloon inflation status—primarily by $CO_2$ concentration effects produced in the gastric environment. In addition, gastric pH also affects $CO_2$ concentration. This particular method can also allow for a greater degree of tuning of the device's useful life based on the composite wall material, e.g., barrier/non-barrier and whether the gas that diffuses in is maintained longer in the balloon if it has a barrier wall versus a non-barrier wall. This particular form of self-inflation can be employed using a self-inflating gastric balloon (e.g., initially inflated by a gas generating reaction in the balloon initiated after swallowing), or an inflatable gastric balloon (e.g., inflated using a catheter, with or without endoscopic assistance, delivered naso-gastrically or any other delivery method). The method can be used with any gastric balloon, including swallowable balloons and balloons placed in the stomach by, e.g., endoscopic methods. The method is particularly preferred for use in connection with intragastric devices; however, it can also be applied to use in, e.g., pulmonary wedge catheters and urinary incontinence balloon devices. The advantages to this technology include the ability to compensate for stomach accommodation, allowing the balloon to adapt to a stomach that may increase in volume over time, thereby maintaining patient satiety. It also permits starting with a smaller amount of inflation gas constituents for a self-inflating balloon. It can prevent spontaneous deflations by utilizing diffusion gradients between gastric balloon systems and the in vivo gastric environment.

In a particularly preferred embodiment, used in connection with $N_2$ (with or without $CO_2$) as the inflation agent, a multi-layer co-extruded blend for the wall layers is employed. A particularly preferred configuration is Nylon 12/Ethyl Methyl Acrylate/Polyvinylidene Chloride/Ethyl Methyl Acrylate/Nylon 12/Linear Low Density Polyethylene+Low Density Polyethylene (also referred to as co-extruded Nylon 12-encapsulated PVDC-Nylon 12-LLDPE+LDPE multilayer). Another particularly preferred configuration is a co-extruded multi-layer Nylon 12/Linear Low Density Polyethylene+Low Density Polyethylene. Selection of the resins for the composite wall construction (as well as selection of using a coextrusion method or adhesives) can be varied to control compliance (stretchiness), puncture resistance, thickness, adhesion, sealing bond strength, orientation, acid resistance, and permeability characteristics to gasses and water vapor to achieve a particular effect.

Automatic Deflation of Intragastric Balloon Systems

The self-inflating (also referred to as automatic inflating) or inflatable (also referred to as manually inflating) intragastric balloon is provided with mechanisms to reliably control timing of deflation. In preferred embodiments, the balloon auto-deflates and passes through the stomach, through the lower gastrointestinal tract, and out of the body at the end of its pre-determined useful life (non-spontaneous), preferably between 30 and 90 days but can be timed to deflate within 6 months. In the preferred embodiments described below, the timing of deflation can be accomplished via the external gastric environment (by conditions of temperature, humidity, solubility, and/or pH, for example) or via the environment within the lumen of the inflated balloon. It is preferable for consistency to control the initiation of the self-deflation process by manipulating the internal balloon environment.

In other embodiments, the patch applied to allow for inverted seams as described above and/or one or more additional patches or other structures added to the balloon construction are made out of an erodible, degradable, or dissolvable material (natural or synthetic) and are incorporated into the wall of the balloon. The patch(es) are of sufficient size to ensure opening of a sufficient surface area to cause rapid deflation, and to prevent re-inflation by seepage of stomach fluid into the balloon. The balloon patch(es) comprise materials that can be applied to the balloon such that a substantially smooth surface is maintained, and preferably comprise a single layer or multi-layered material. The patch(es) are constructed using an erodible, disintegrable, degradable or other such material that is preferably tissue-compatible and degrades into non-toxic products or is a material that slowly hydrolyzes and/or dissolves over time (e.g., poly(lactic-co-glycolic acid) (PLGA), poly(lactide-co-glycolide) (PLG), polyglycolic acid (PGA), polycaprolactone (PCL), polyesteramide (PEA), polyhydroxyalkanoate (PHBV), polybutylene succinate adipate (PBSA), aromatic copolyesters (PBAT), poly (lactide-co-caprolactone) (PLCL), polyvinyl alcohol (PVOH), polylactic acid (PLA), poly-L-lactic acid PLAA, pullulan, polyethylene glycol (PEG), polyanhydrides, polyorthoesters, polyaryletherketones (PEEK), multi-block polyetheresters, poliglecaprone, polydioxanone, polytrimethylene carbonate, and other similar materials). These erodible, disintegrable, or degradable materials can be used alone, or in combination with other materials, or can be cast into/co-extruded, laminated, and/or dip coated in conjunction with non-erodible polymers (e.g., PET or the like) and employed in the construction of the balloon. Degradation/erosion occurs, is initiated by, and/or is controlled by the gastric environment (e.g., by conditions of temperature, humidity, solubility, and/or pH, for example), or is controlled within the lumen of the balloon (e.g., by conditions of humidity and/or derived pH, for example) based on what the patch is exposed to. Thickness of the polymer as well as environment which affects degradation and time of exposure can also facilitate degradation timing. Degradation/erosion are timed such that they occur once the pre-determined balloon useful life is completed (e.g., inflation is maintained for from 25 to 90 days in vivo in the stomach before degradation/erosion results in formation of an opening permitting deflation). As an alternative to (or in connection with) using an degradable material for the patch, the patch can comprise a similar fluid retention barrier film or the same film as the remaining wall of the balloon which is adhered to the balloon using a weak adhesive, or welded or adhered such that after a specified amount of time the patch delaminates from the applied area and allows for an opening for inflation fluid release for deflation. Or if deemed necessary for rapid deflation the entire balloon composite wall can be made of the erodible material. The mechanism of using an erodible material or a material that mechanically fails after a pre-specified time is be similar for all embodiments for deflation mechanisms described below as well. The timing of degradation or erosion can be controlled using the external gastric environment (e.g., by conditions of temperature, humidity, solubility, and/or pH, for example) and/or can be controlled by conditions within the lumen of the balloon (e.g., by conditions of humidity and/or pH of residual liquid in the balloon).

Figure 22A:
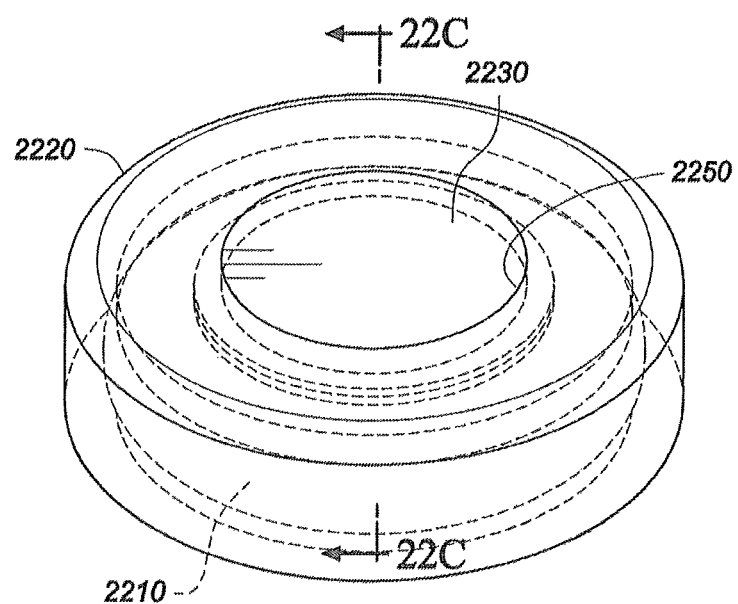
FIG. 22A is a perspective view of a deflation mechanism 2200 to achieve deflation of a balloon (not depicted), in one embodiment, wherein the deflation mechanism 2200 includes an eroding core 2210 (shown in phantom) with a protective barrier 2230 (shown partially in phantom) between the core 2210 and a vent 2250 to the intragastric environment, wherein the protective barrier 2230 is held in place by a housing 2220.
Figure 22B:
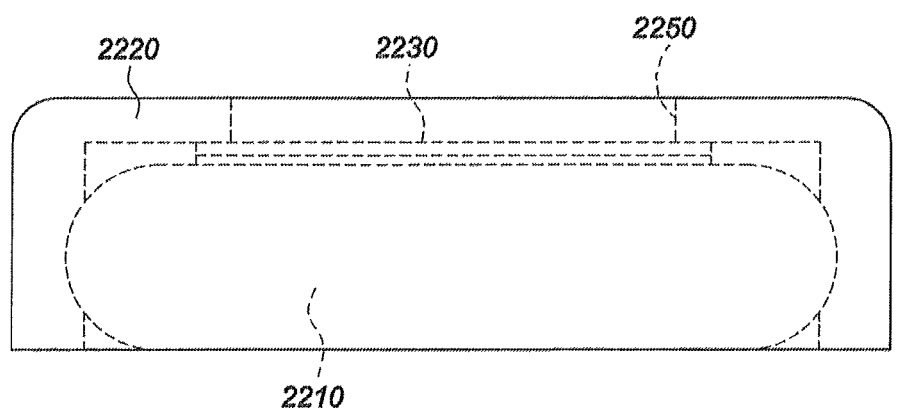
FIG. 22B is a side view of the deflation mechanism 2200 of FIG. 22A.
Figure 22C:
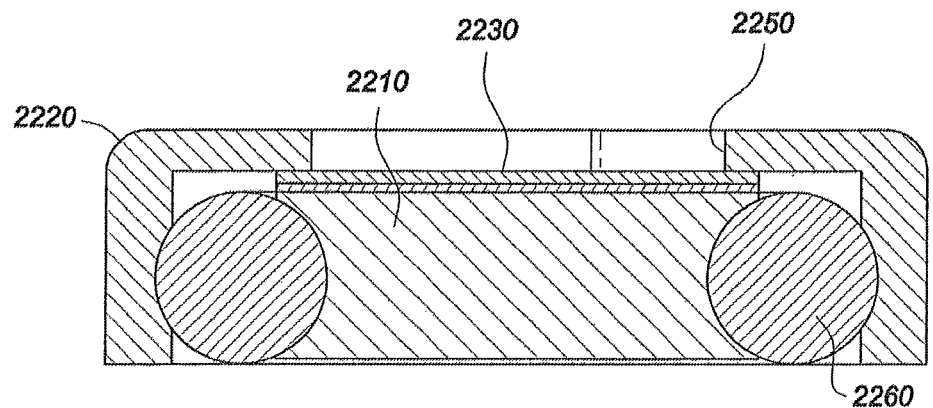
FIG. 22C is a cross-sectional view of another embodiment of the deflation mechanism 2200, wherein the cross-section is similar to a cross-section taken along the line 22C-22C of FIG. 22A, including a compressed radial seal 2260 held in place against the housing 2220 by an erodible core 2210 with a protective barrier 2230 between core 2210 and the vent 2250 to the intragastric environment.
Figure 22D:
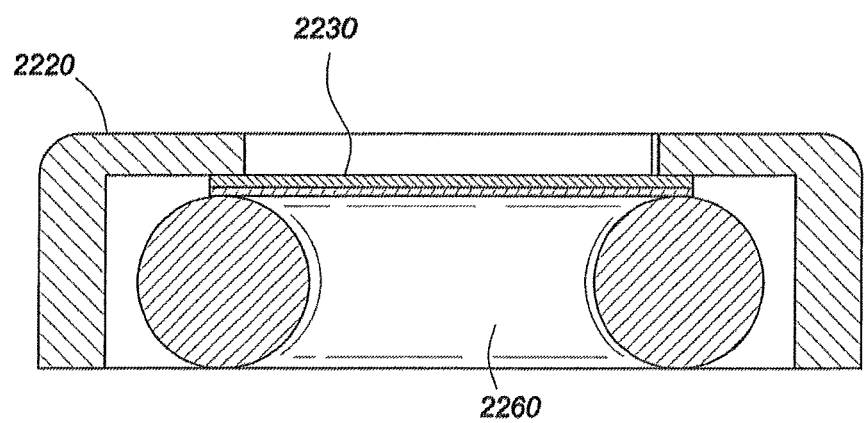
FIG. 22D depicts the deflation mechanism 2200 of FIG. 22C after the core has eroded, thereby allowing the radial seal 2260 to relax into an uncompressed configuration wherein it is spaced from the housing 2220.
Figure 24A:
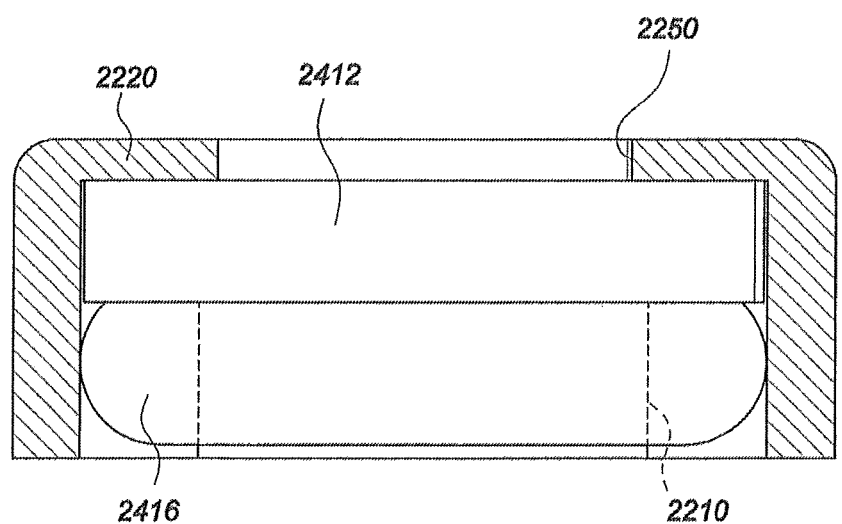
FIG. 24A is a cross-sectional view of a deflation mechanism 2200, in still another embodiment, utilizing an erodible core 2210 in a radial ring seal 2416, with compression ring 2412 to expel the seal 2416 once support from the erodible core 2210 (shown partially in phantom) is removed. The mechanism further includes a housing 2220 and a vent 2250 to the intragastric environment.

In other embodiments, a plug or plugs (optionally in conjunction another degradable retaining structure) can be incorporated into the balloon construction and can consist, all or in part, of an erodible, disintegrable, or otherwise degradable synthetic or natural polymer similar to those described above (e.g., PLGA, PLAA, PEG, or the like). The plug can be formed into various shapes (e.g., cylinder shape or radial shape, as depicted in FIGS. 22A-D) to achieve various surface-to-volume ratios so as to provide a preselected and predictable bulk degradation pattern for the erodible polymer. The plug can incorporate a releasing mechanism that can be chemically initiated after degradation/erosion begins, such that the septum or plug material pops out of the balloon or falls inside of the balloon, thereby creating a passageway for fluid release and subsequent deflation of the balloon. Mechanical additions that can be used in conjunction with a plug include a degradable/erodible/disintegrable material that holds a plug (e.g., of a non-degradable or degradable material) in place or a compressed spring housed within the retaining structure or plug structure. More specifically one preferred embodiment to achieve deflation can comprise a housing, a radial seal, a solid eroding core, and a protective film attached to the external surface of the eroding core (FIGS. 22A-B). The inside of the eroding core is exposed to the internal balloon liquid. The core creates a compressive force that holds the seal against the housing. As the core erodes, the compression between the housing and the radial seal is reduced until there is clearance between the housing and the seal. Once there is clearance, gas can move freely from the inside of the balloon to the outside environment (FIG. 24A). The seal can fall out of the housing and into the balloon. The diameter, length, and material types can be adjusted in order to create the deflation at a desired time point. Example materials for each component used to achieve this deflation mechanism can be as follows. Housing—biocompatible structural material, capable of withstanding enough radial force to form an air tight seal. Materials can include polyethylene, polypropylene, polyurethane, UHMWPE, titanium, stainless steel, cobalt chrome, PEEK, or nylon. Radial Seal—composed of a biocompatible elastic material, capable of providing liquid and gas barrier to acidic environments. Materials can include silicon, polyurethane, and latex. Eroding Core—a material capable of breaking down at a predictable rate at given environmental conditions. Materials can include PLGA, PLA, or other polyanhydrides that are capable of losing integrity over time or any materials listed above that provide erodible characteristics.

Figure 24B:
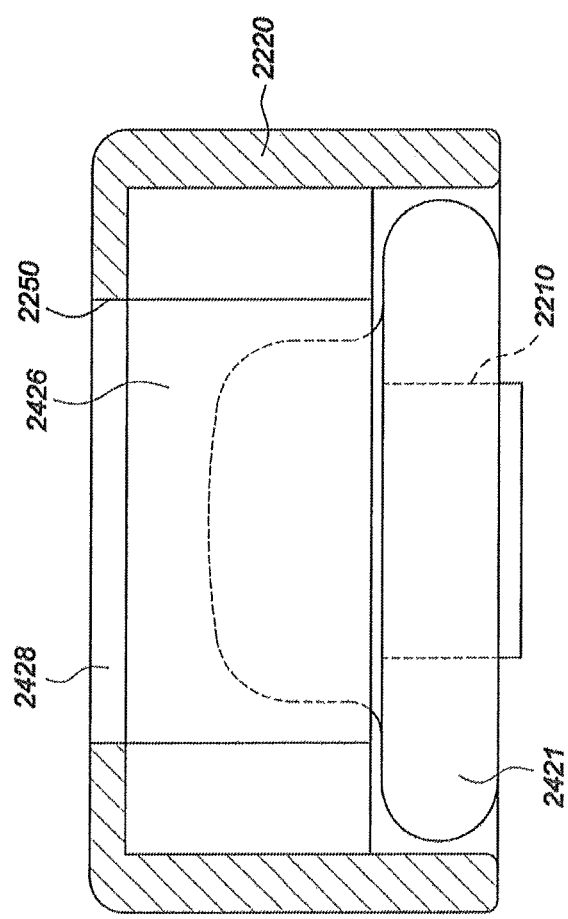
FIG. 24B is a cross-sectional view of a deflation mechanism 2200, in yet another embodiment, utilizing a seal 2416 with an erodible core 2210 (shown partially in phantom) and a push out ring 2426 held in a casing 2220 having a vent 2250 to the intragastric environment.

For the spring mechanism, once the material degrades, the spring is released and/or the plug/septum is pulled into the balloon or pushed out of the balloon, thus releasing fluid once an orifice has been created by release of the spring mechanism and pushing out or pulling in of the plug (FIG. 24B).

Figure 24C:
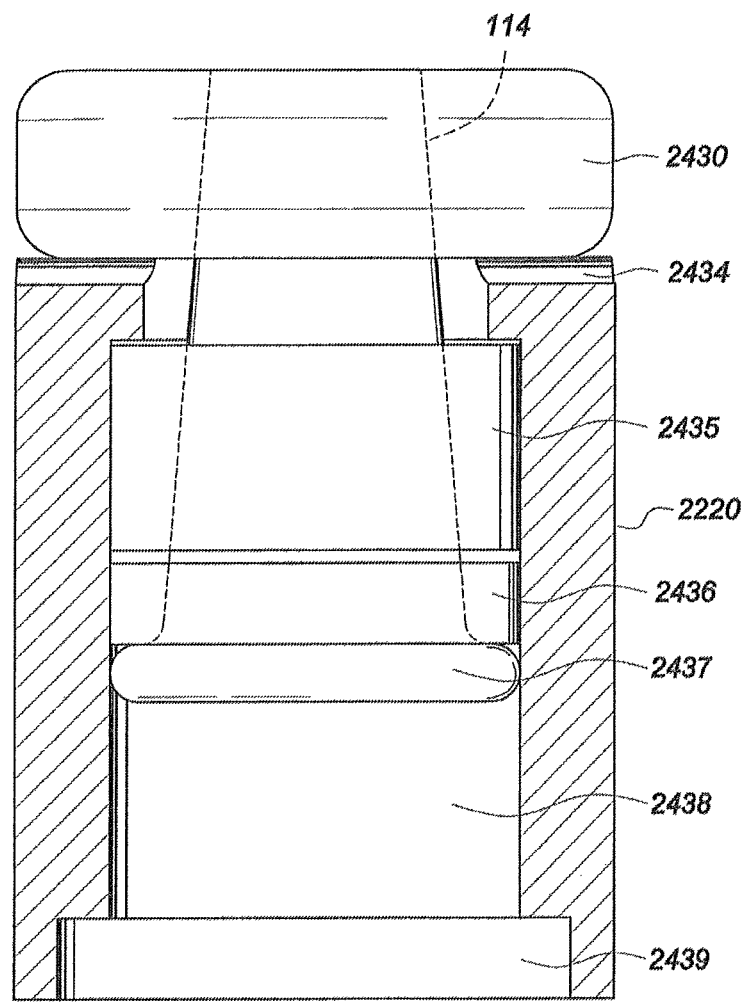
FIG. 24C is a cross-sectional view of a deflation mechanism 2200, in yet another embodiment, including a moisture expanding material 2435 that pulls the septum 2437 (shown partially in phantom) out of position to cause balloon deflation. The mechanism further includes a head 2430, a moisture inlet port 2434, a push ring 2436 attached to the septum 2437, a clearance 2438, and an inoculation spacer 2439.

Deflation mechanisms utilizing a septum and moisture absorbing expansion material and a moisture eroding material. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon (FIG. 24C). In order to protect the expanding material from moisture until a desired time point, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

Figure 25A:
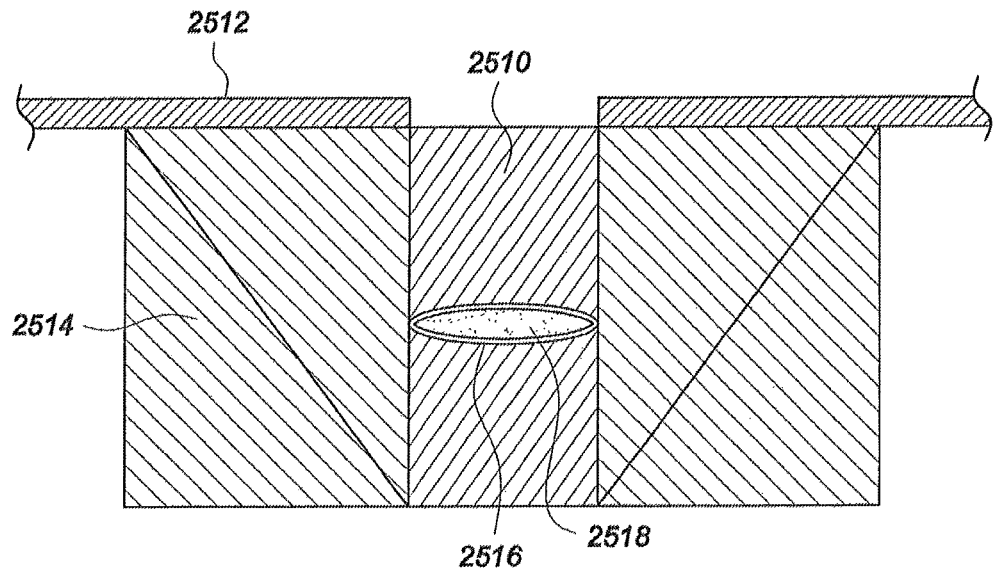
FIG. 25A is a cross-sectional view of a deflation mechanism, in another embodiment, including an eroding plug 2510 disposed within a casing 2514 in the wall 2512 of a balloon (not shown), wherein the eroding plug 2510 contains a compressed pellet or gas releasing pellet 2518 encapsulated with a water restricting membrane 2516, wherein the pellet 2518 is compressed.
Figure 25B:
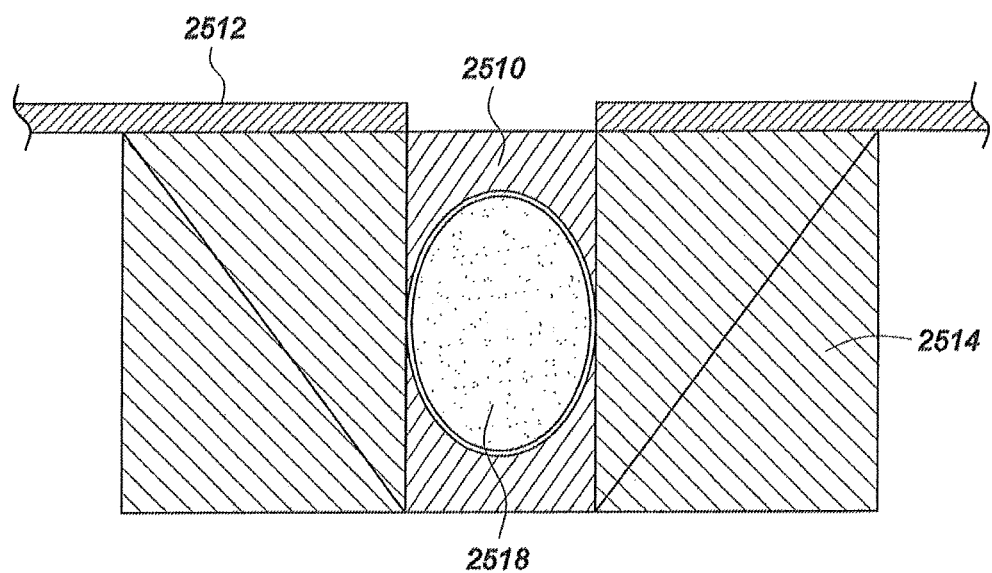
FIG. 25B depicts another view of the deflation mechanism of FIG. 25A, wherein the pellet 2518 is expanded.
Figure 26:
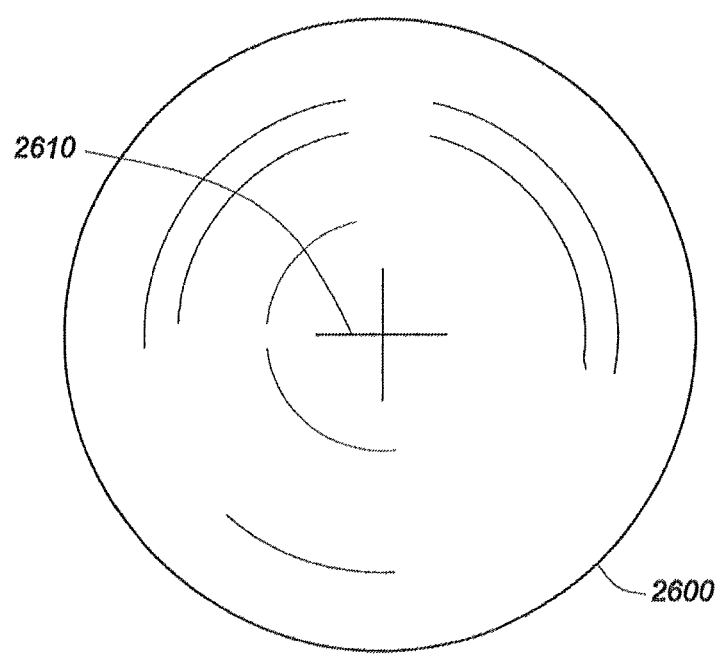
FIG. 26 is a top view of yet another deflation mechanism in an outermost layer of a balloon 2600, in one embodiment, wherein the balloon 2600 is "scored" or hatched with erodible material to create small channels 2610 that erode over time, so as to provide for deflation of the balloon 2600.
Figure 27A:
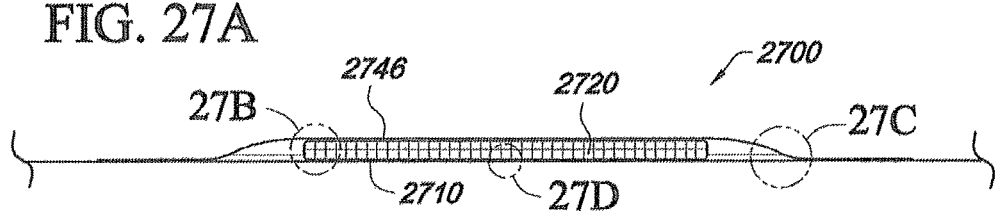
FIG. 27A is a cross-sectional view of another embodiment of a deflation mechanism for providing abrupt deflation of a balloon after a desired period of time has elapsed, including a rupturable structure 2700, which includes the polymeric wall 2710 of the entire balloon or a section of the composite polymeric wall 2710, such as a patch. The structure 2700 further includes a water expanding material 2720 with a parylene coating 2730. The parylene coated water expanding material 2720 is disposed between the balloon polymeric wall 2710 and a thin external protective later 2746, which is attached to the wall 2710 by a weakened area 2750 of a patch bond 2770. A perforation, hole or opening 2760 in the polymeric wall 2710, defined by edge 2761, enables water injected into the balloon to be absorbed by the water expanding material 2720.
Figure 27B:
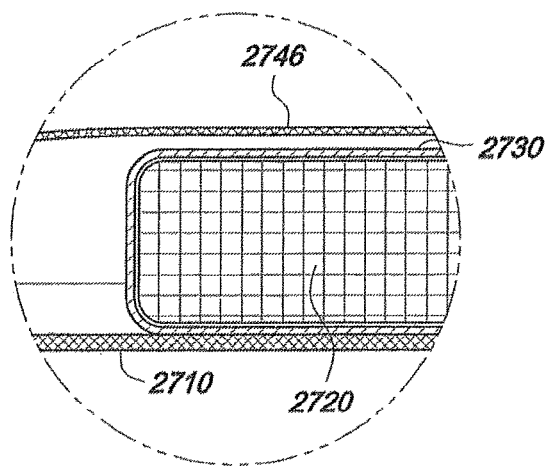
FIG. 27B is an enlarged view of a portion of the rupturable structure 2700 of FIG. 27A, wherein the portion is denoted by circle 27B of FIG. 27A.
Figure 27C:
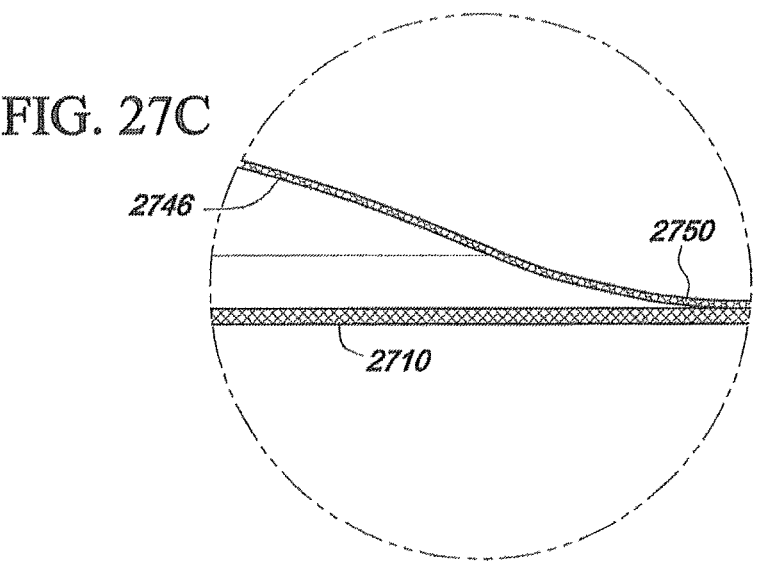
FIG. 27C is an enlarged view of another portion of the rupturable structure 2700 of FIG. 27A, wherein the portion is denoted by circle 27C of FIG. 27A.
Figure 27D:
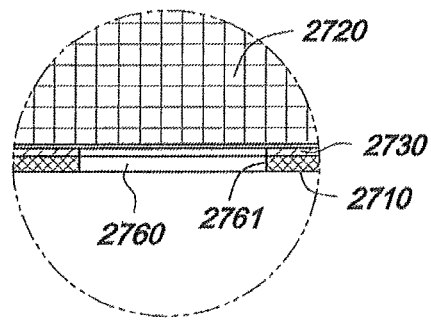
FIG. 27D is an enlarged view of yet another portion of the rupturable structure 2700 of FIG. 27A, wherein the portion is denoted by circle 27D of FIG. 27A.
Figure 27E:
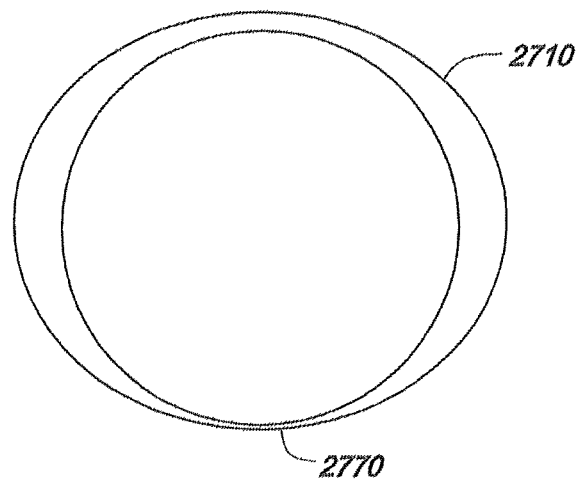
FIG. 27E is a top view of the rupturable structure 2700 of FIG. 27A.

In certain embodiments, the balloon can incorporate one or more plugs in the wall of the balloon that contain a compressed pellet (FIGS. 25A-B) or gas releasing pellet. The pellet can be comprised of any combination of constituents that, when activated, emit $CO_2$ gas (e.g., sodium bicarbonate and citric acid, or potassium bicarbonate and citric acid, or the like). The pellet can be in tablet or rod form protected by an erodible, disintegrable, or degradable material that is preferably tissue-compatible and degrades into non-toxic products or that slowly hydrolyzes and/or dissolves similarly to the plugs and patches described above (e.g., poly(lactic-co-glycolic acid) (PLGA), polyvinyl alcohol (PVOH), polylactic acid (PLA), poly-L-lactic acid PLAA, Pullulan, Polyethylene Glycol, polyanhydrides, polyorthoesters, polyaryletherketones (PEEK), multi-block polyetheresters, poliglecaprone, polydioxanone, polytrimethylene carbonate, and other like materials). Degradation/erosion of the plug initiates the reaction of the two chemicals in the pellet and subsequently leads to formation of gas (e.g., $CO_2$). As sufficient gas is trapped or built up, sufficient pressure is eventually generated to push out the softened polymer material and create a larger channel for the $CO_2$ gas in the balloon to escape. External pressure applied by the stomach to the balloon (e.g., squeezing) can contribute to the process of creating a larger channel. Dimensions and properties of the plug (diameter, thickness, composition, molecular weight, etc.) comprised of the polymer drives the timing of degradation.

In other embodiments, plugs or patches of different shapes or sizes similar to those of the plugs described above can be employed within the balloon lumen in a multi-layer configuration including a semi-permeable membrane to facilitate balloon deflation. The plug or patch is made of similar degradable/erodible/dissolvable material as described above (e.g., poly(lactic-co-glycolic acid) (PLGA), polyvinyl alcohol (PVOH), polylactic acid (PLA), PLAA, pullulan, and other like materials) and contains a compartment enclosed by a semi-permeable membrane (impermeable to an osmolyte) that contains a concentrated solution of a solute or osmolyte (such as glucose, sucrose, other sugars, salts, or combination thereof). Once the plug or patch begins to degrade or erode, the water molecules move by osmosis down the water gradient from the region of greater water concentration to the region of lower water concentration across the semi-permeable membrane into the hypertonic solution in the compartment. The compartment containing the osmolyte swells and eventually bursts, pushing the membranes and the degraded plug or patch out, thereby allowing rapid gas loss through the newly created channels or areas.

In certain embodiments, a balloon composed of a septum, moisture eroding material inside an inlet port, and moisture absorbing expansion material is employed. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon. In order to protect the expanding material from moisture until a desired time point has been reached, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

Figure 23:
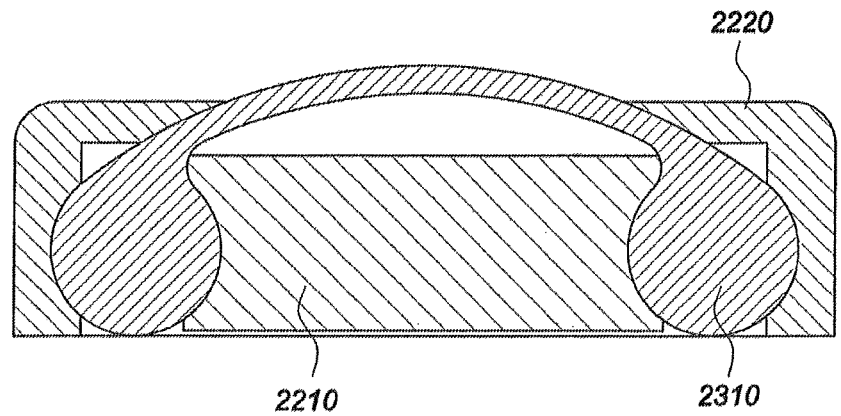
FIG. 23 is a cross-sectional view of a deflation mechanism 2200, in yet another embodiment, utilizing a one-piece seal with protective canopy 2310 held in place by an erodible core 2210.

Another mechanism for self-deflation is to create a forced de-lamination scheme, which can provide a larger surface area to ensure rapid deflation. In, e.g., a balloon having a tri-layer wall, the outermost layer is substantially strong enough to hold the inflation fluid (e.g., polyethylene terephthalate (PET) or the like), the middle layer is comprised entirely of an erodible material (e.g., PVOH or the like) while the inner layer is comprised of a weaker material (e.g., polyethylene (PE) or the like). The PET or outermost layer is "scored" or hatched with erodible material to create small channels that erode over time (FIG. 23). This creates channels such that the gastric fluid seeps into the balloon layers and starts degrading the fully erodible material. When the erodible layer degrades or dissolves, the material that composes the innermost layer also erodes, degrades or dissolves since it is not strong enough to withstand the gastric forces/environment on its own. The balloon then collapses on itself and eventually passes through the lower gastrointestinal tract. Having an erodible layer sandwiched between a strong and weak layer facilitates timing of erosion by creating a longer path length than an erodible plug or patch affected by the gastric environment. The distance between scores or openings can also be selected so as to provide a desired deflation rate.

In another embodiment providing abrupt deflation of the balloon after a desired period of time has elapsed, the composite wall of the entire balloon or a section of the composite wall (patch) includes several material layers that are slowly penetrated by water that has been injected inside the balloon during the manufacturing process or during the inflation process (FIGS. 27A-E). This water penetrates through the layers, eventually reaching a material that substantially expands, rupturing a thin external protective later, and creating a large hole (FIG. 27D) for gas to escape and the balloon to deflate. The water expanding material is protected from liquid via a coating or sheath, such as parylene, which allows a controllable amount of moisture exposure. Once water reaches the expansion material, it exerts a force on the protective outer layer, causing it to rupture. The outer layer may be created with a weakened bonding area (FIG. 27E), a partially scored area, or other methods of ensuring a desired rupture location and to facilitate desired timing for auto-deflation to take place. There can be any number of layers between the moist environment and the moisture expanding center. Each material layer can have different erosion rates (e.g., fast or slow) and can be selected by the predetermined time deflation is desired to occur (e.g., after 30 days, 60 days, or more). By varying the number, thickness, and rate of each of the circumferential layers, the time to deflation can be accurately controlled.

Figure 28A:
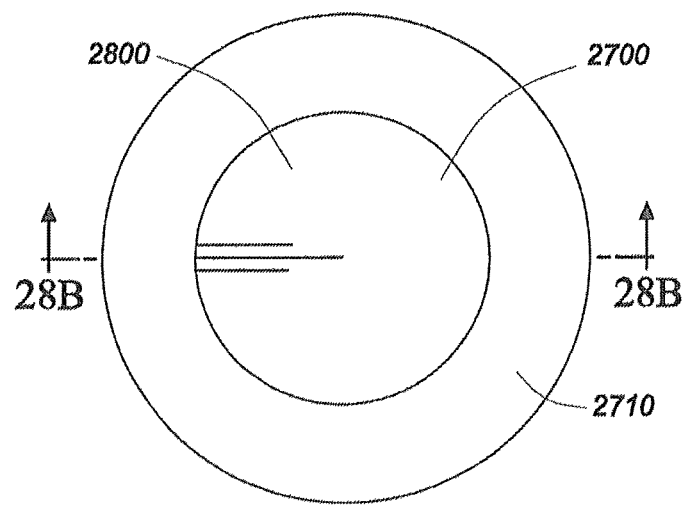
FIG. 28A is a top view a rupturable structure 2700, in another embodiment, including a pressure sealing button 2800 adhesively sealed to the balloon material 2810.
Figure 28B:
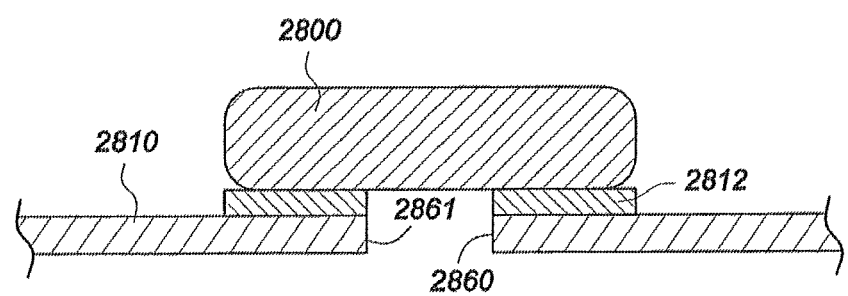
FIG. 28B is an enlarged cross-sectional view of the rupturable structure 2700 of FIG. 28A, wherein the cross-section is taken along line 28B-28B of FIG. 28A, the rupturing structure 2700 including an adhesive 2812 securing the pressure sealing button 2800 to the balloon material 2710, so that the pressure sealing button 2800 covers a perforation, hole or opening 2760 in the balloon material 2710 acting as a water access hole.

Alternatively a pressure sealing button that is adhesively bonded over a perforation in the balloon material can be provided for deflation (FIGS. 28A and B). The adhesive bonding the button erodes over time when it comes into contact with moisture derived from the gastric fluid or that has been injected inside the balloon. Once the adhesive can no longer bond and create an airtight seal between the adhesive and the button, the balloon will rapidly deflate. By controlling the hole size and moisture exposure of the adhesive, the erosion time can be accurately predicted.

Figure 29A:
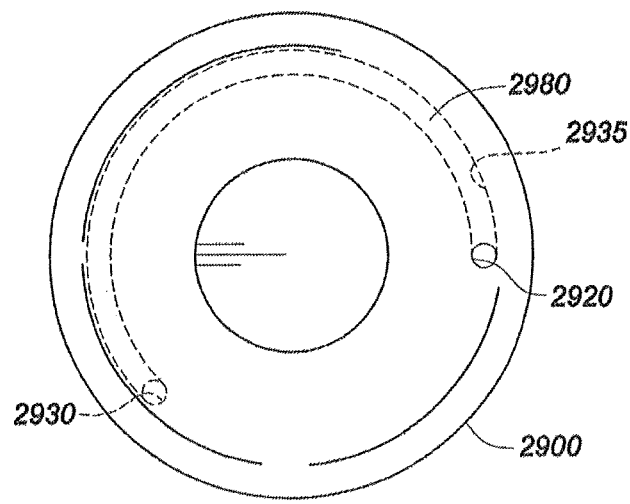
FIG. 29A is a top view of another deflation mechanism, including a head 2900 with a septum 2910 attached to the balloon composite wall (not depicted), wherein the head 2900 includes external and internal ports, 2920 and 2930 respectively, connected by a channel 2935 that is filled a water-dissolving or acid-dissolving material 2980 (shown in phantom).
Figure 29B:
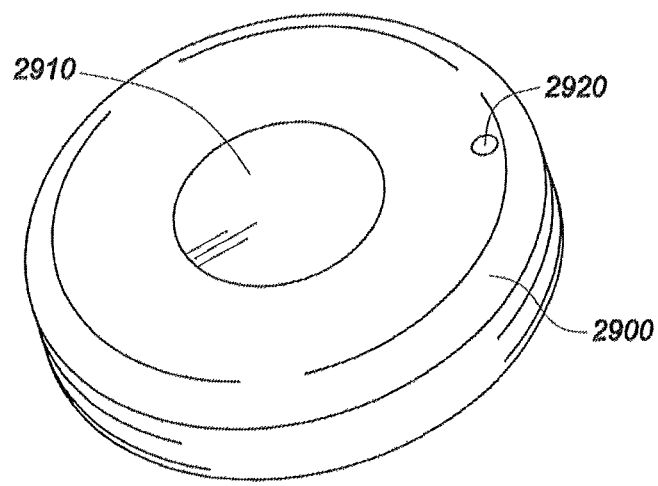
FIG. 29B is an enlarged perspective view of the head 2900 of FIG. 29A.
Figure 29C:
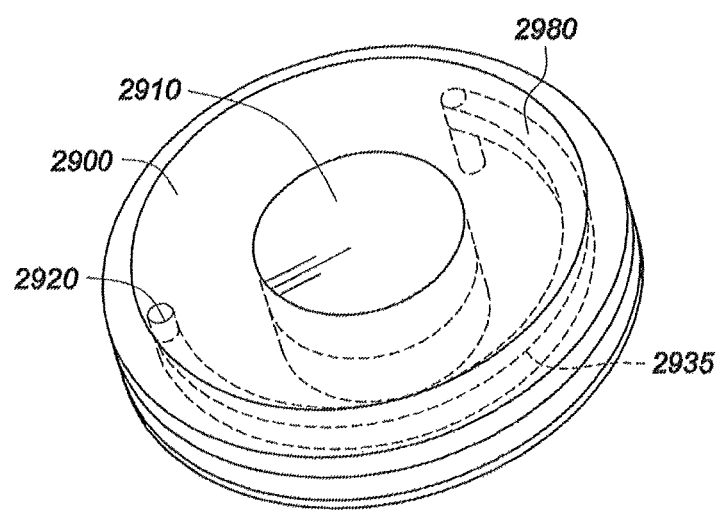
FIG. 29C is an enlarged perspective view of the head 2900 of FIG. 29A, with portions shown in phantom to show greater detail thereof.
Figure 29D:
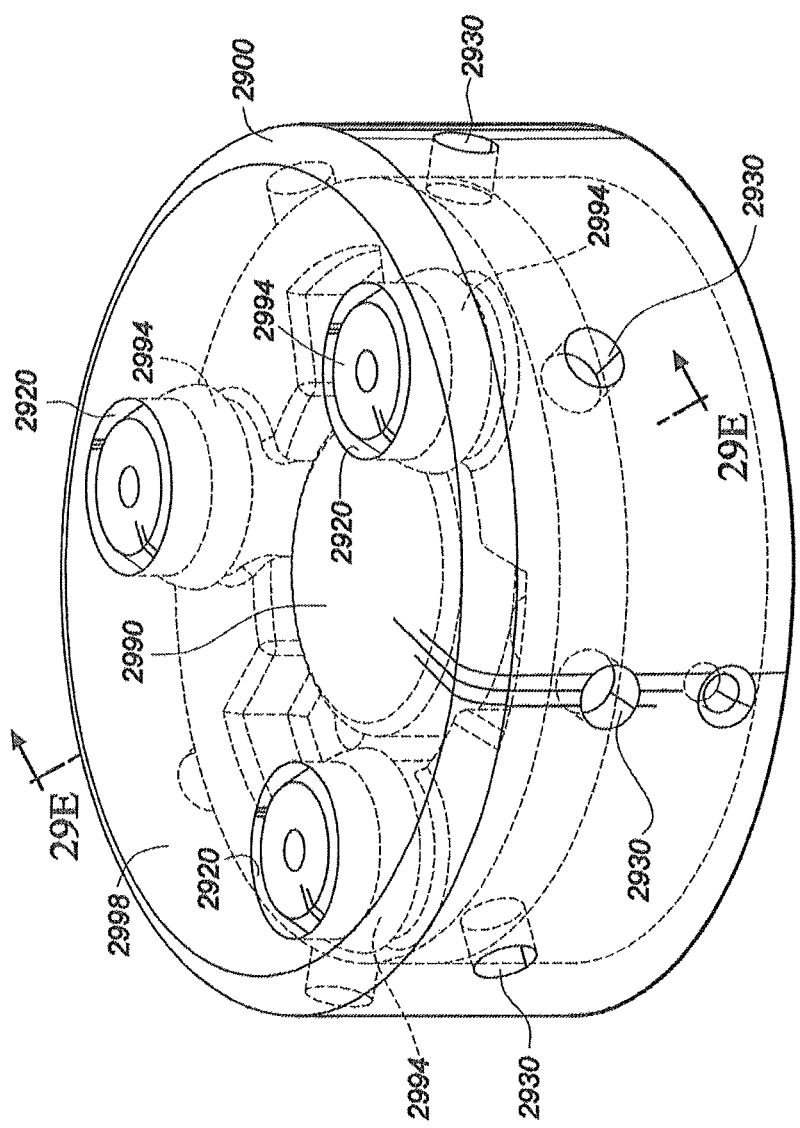
FIG. 29D is a perspective view of a head 2900, in another embodiment, including a casing 2998 with a plurality of internal ports 2930 (portions shown in phantom), external ports 2920 with seals 2994 (shown in phantom) and channels configured with an expanding material 2990 (shown in phantom) and a push-out component 2970.
Figure 29E:
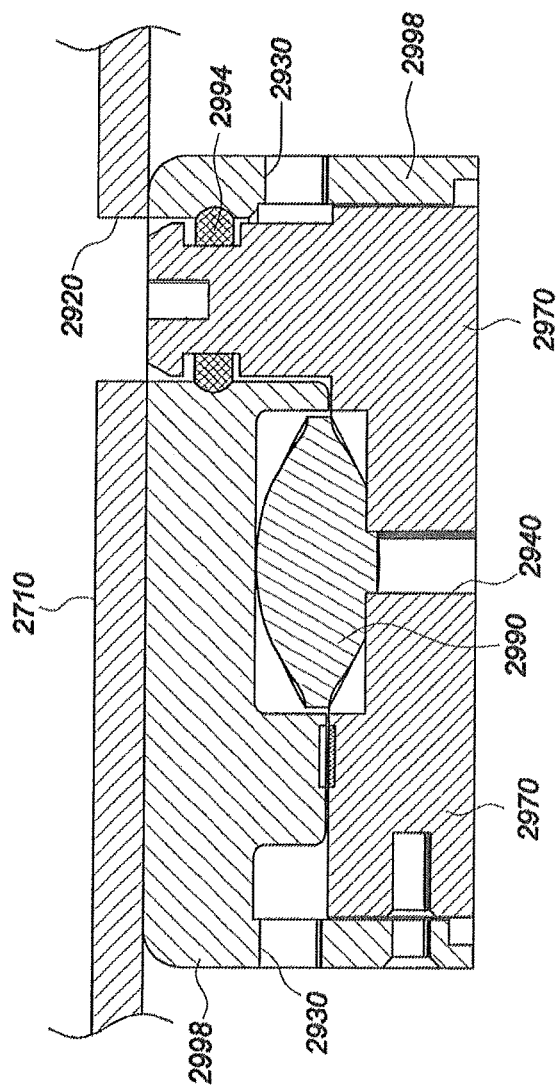
FIG. 29E is a cross-sectional view of the head 2900 of FIG. 29D attached to the balloon wall 2710, wherein moisture within the balloon can pass through an internal portion 2940 to hydrate the expanding material 2990, which (when hydrated and expanded) pushes the push-out component 2970 out of the casing 2998, whereby the internal ports 2930 and external ports 2920 are opened to thereby allow gas egress from the balloon interior, wherein the cross-section is taken along line 29E-29E of FIG. 29D.

Deflation can also be facilitated by creating a series of connecting ports within the septum or on another similar structure attached to the balloon composite wall. The ports can be constructed using a water-dissolving or acid-dissolving, biologically compatible, low permeability substance, such as gelatin (FIG. 29A-B). The diameter of the hole, number of holes, channel width, and channel length can all be adjusted to control the dissolving parameters. Once the material in the ports and channel is dissolved, there is a clear path for gas trapped in the balloon to escape, eventually resulting in a deflated balloon. The water can be gastric fluid or controlled internally by including water inside the balloon at assembly or during the inflation process. There can be a plurality of port openings to guarantee gas transmits. Additionally, there are several variables that can be adjusted to control dissolution time: size of the port openings; number of port openings; the length of the internal channel; the width of the internal channel; and the rate of material dissolution. The port/channel layout design can ensure that only a small amount of surface area is exposed to moisture at any particular time, thereby controlling the rate of erosion and ultimately deflation. In an alternative embodiment, depicted in FIGS. 29D-E, an expandable material is employed to displace a push out component so as to initiate deflation.

Figure 30A:
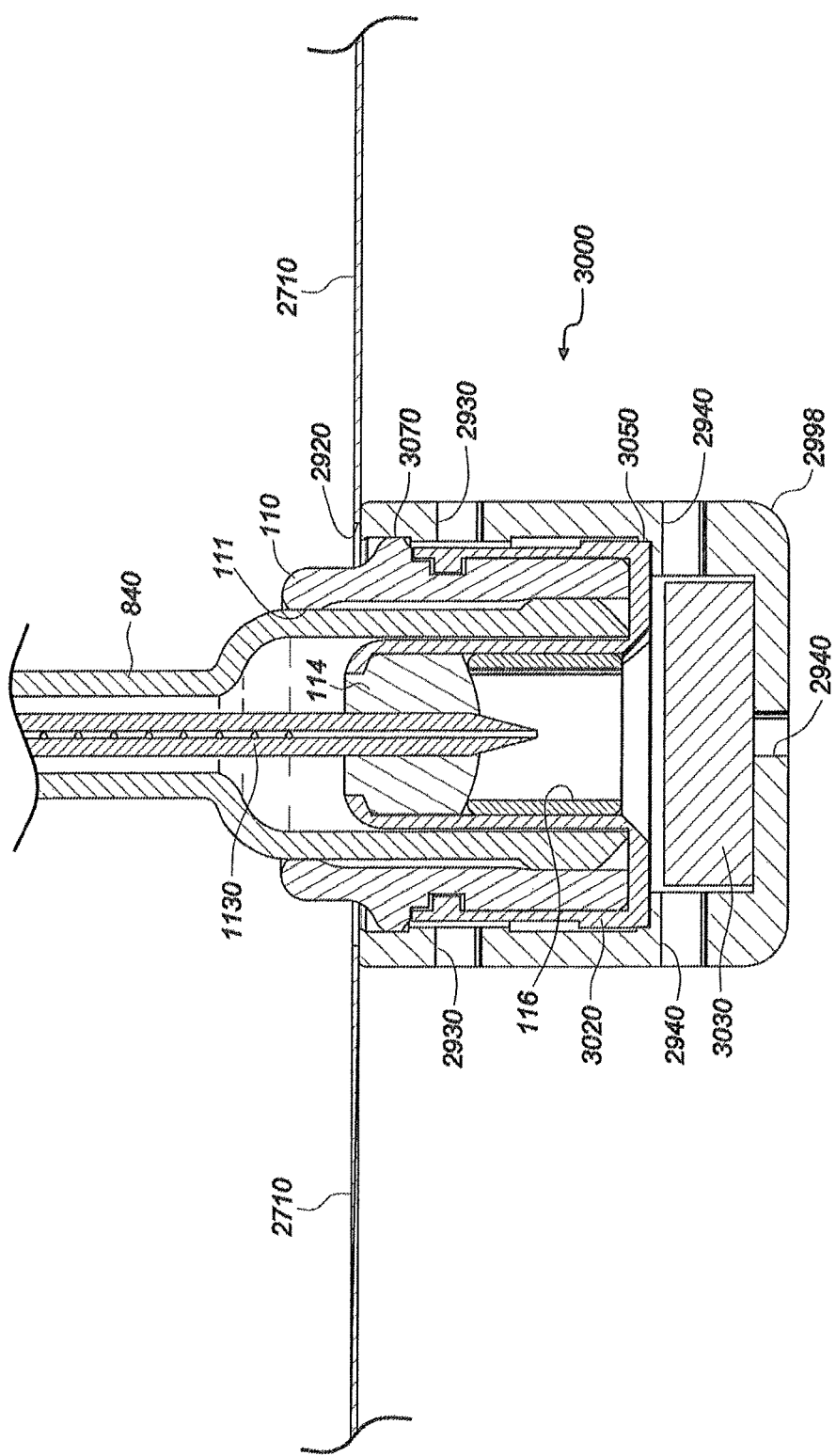
FIG. 30A is a cross-sectional view of a port 3000 attached to a balloon film 2710, the port 3000 encompassing both an inflation mechanism (e.g., a self-sealing valve system) and deflation mechanism in the same location. The port 3000 engages a catheter needle sleeve 840 with a needle 1130. The port 3000 includes a silicon head 110 with a lip 111 that engages the needle sleeve 840. The port 3000 also includes a septum 114 for engaging the needle 1130, a press fit 3050, a casing 2998, an expanding device 3030 with an internal vent 72940, an insert 3020, and a compression seal 3070 blocking the vents 2930 and 2920.
Figure 30B:
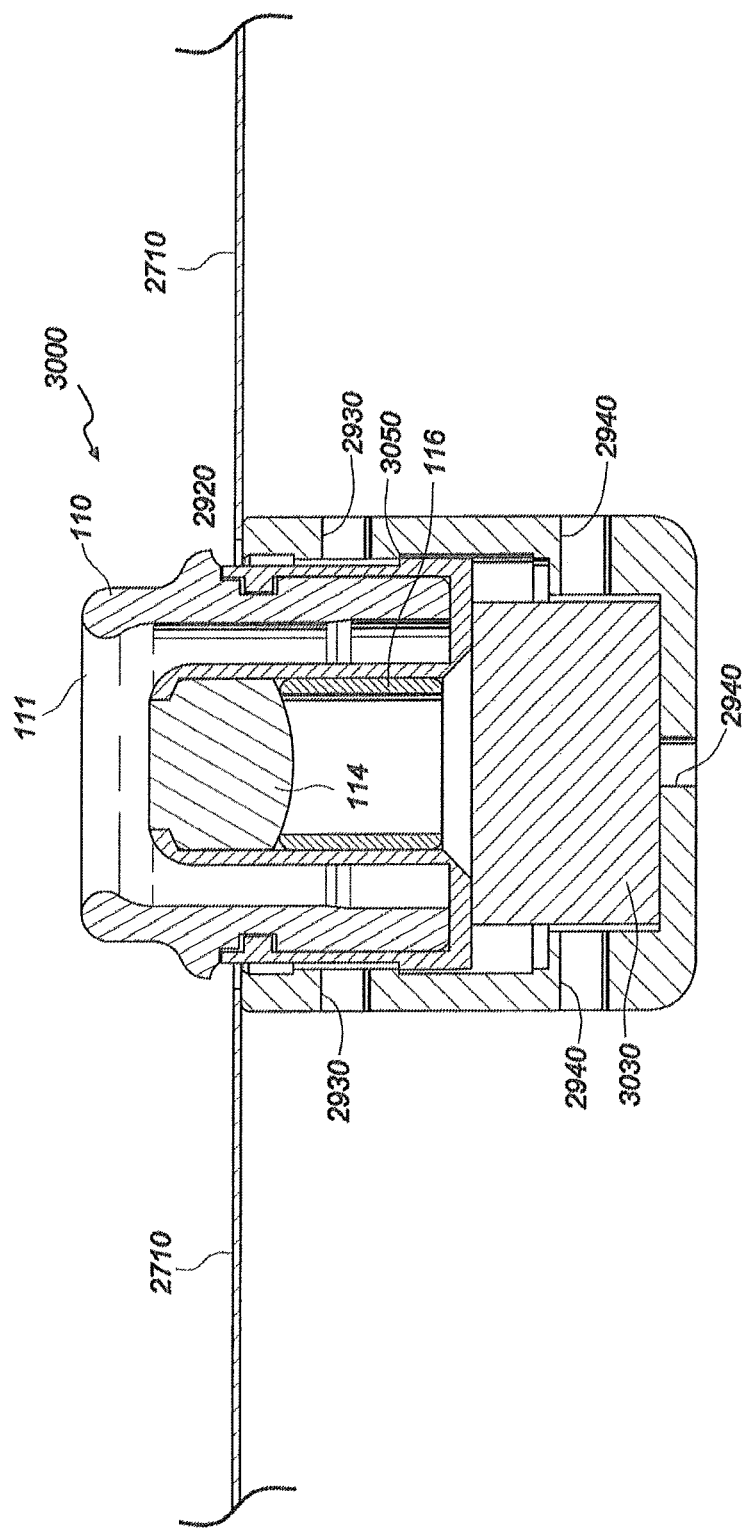
FIG. 30B depicts a cross section of the port 3000 of FIG. 30A with the seal 3070 displaced, enabling fluid communication through an external vent 2920.
Figure 30C:
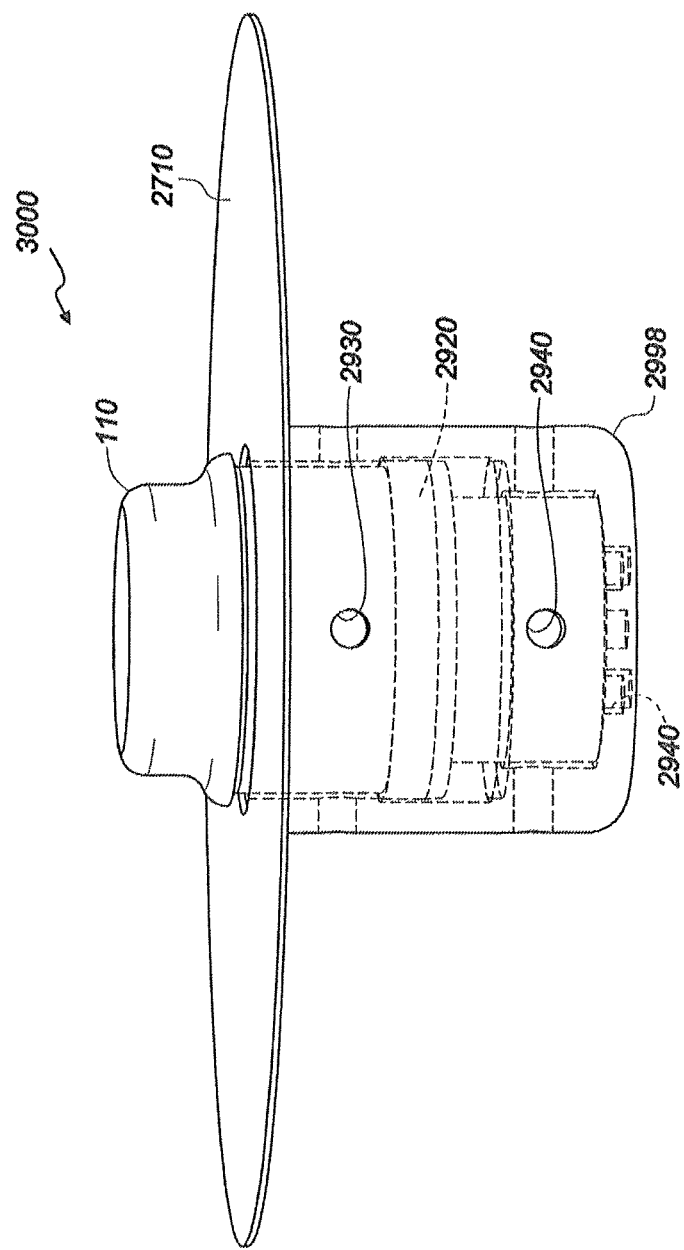
FIG. 30C is a perspective view of the port 3000 of FIG. 30A, with portions shown in phantom to show greater detail thereof, wherein the expanding device 3030 is in an expanded state and the seal 3070 is displaced.
Figure 30D:
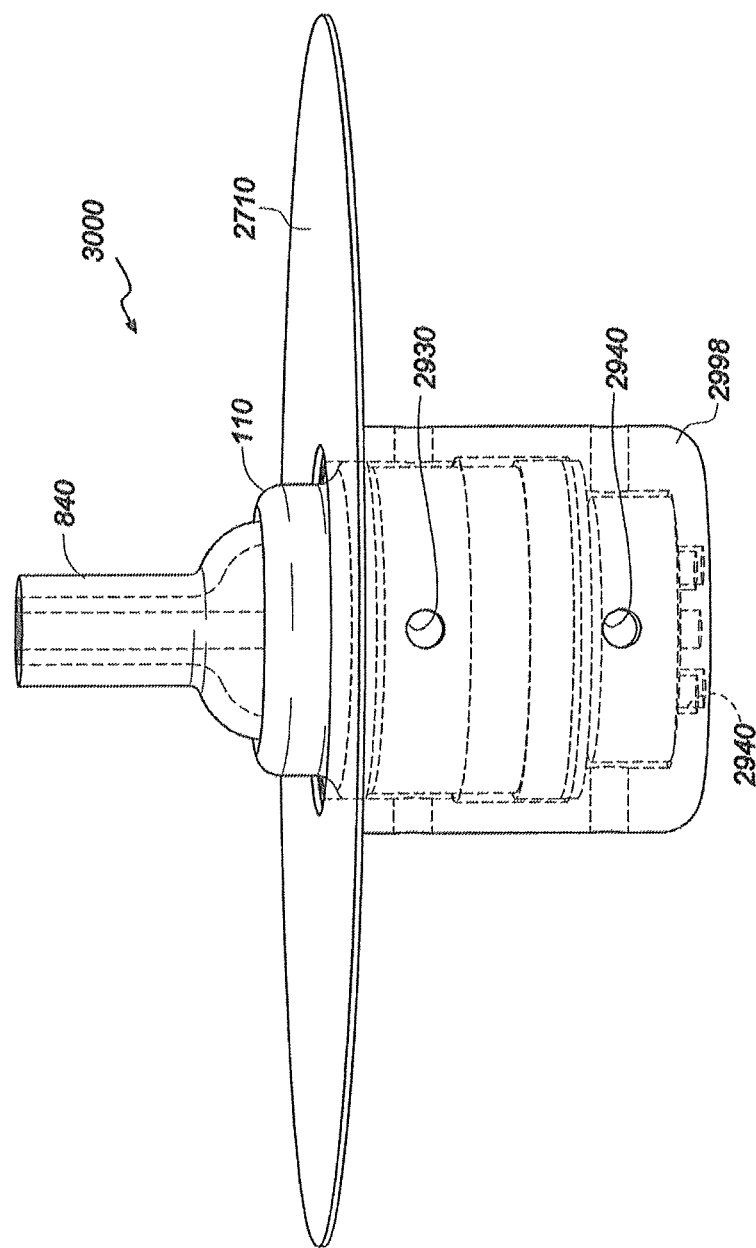
FIG. 30D is a perspective view of the port 3000 of FIG. 30A, with portions shown in phantom to show greater detail thereof, wherein the expanding device 3030 is in an unexpanded or compressed state and the seal 3070 is engaged.
Figure 31A:
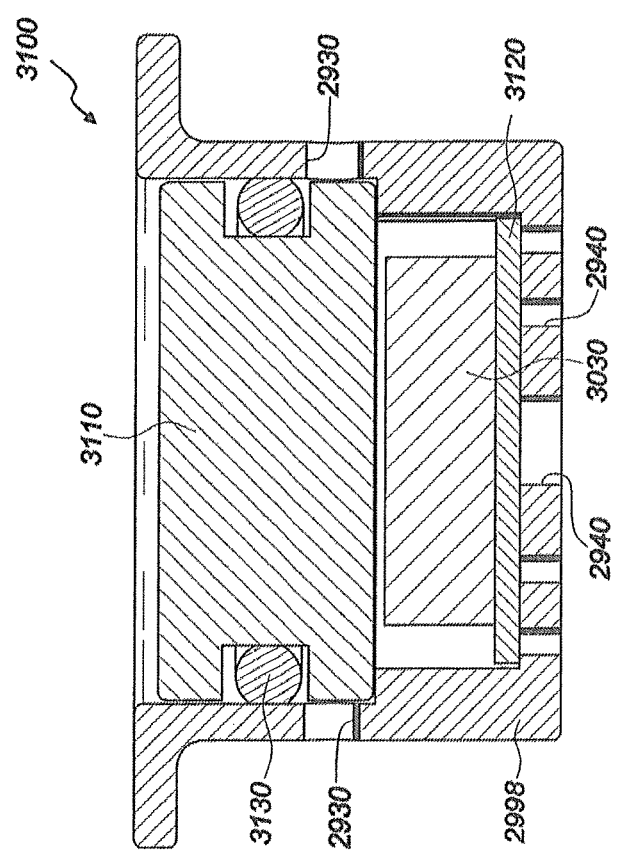
FIG. 31A is a cross-sectional view a deflation port 3100 in another embodiment, including a plunger 3110, a seal 3130, vents 2930, a casing 2998, an expanding device 3030 and a water retainer 3120, wherein the expanding device 3030 is in a contracted or compacted state so that the seal 3130 blocks the vents 2930.
Figure 31B:
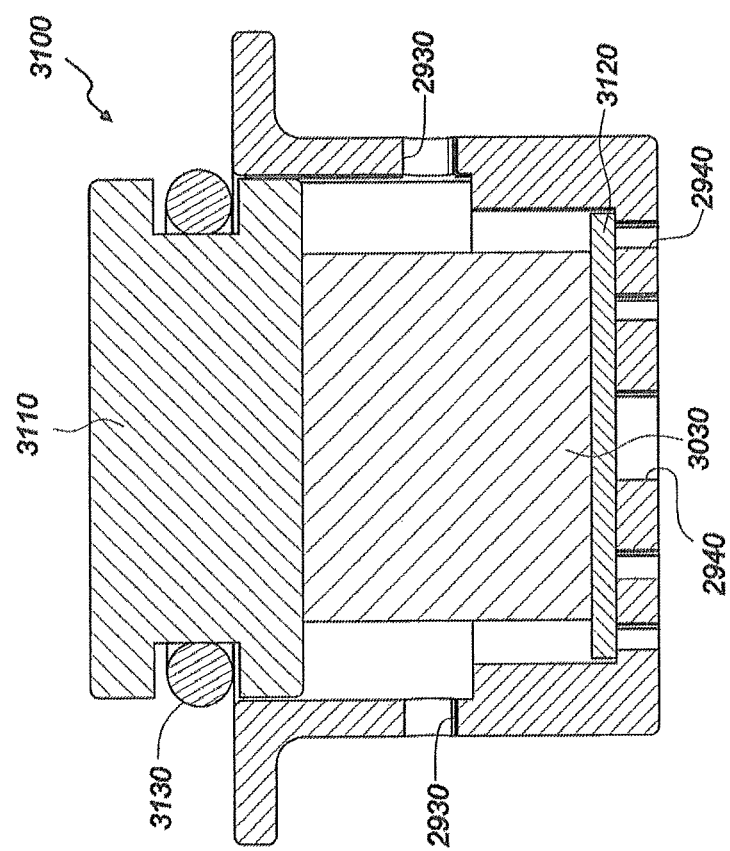
FIG. 31B is a cross-sectional view of the deflation port 3100 of FIG. 31A, wherein the expanding device 3030 is in an expanded state, whereby the seal 3130 is displaced, thereby opening the vents 2930.
Figure 31C:
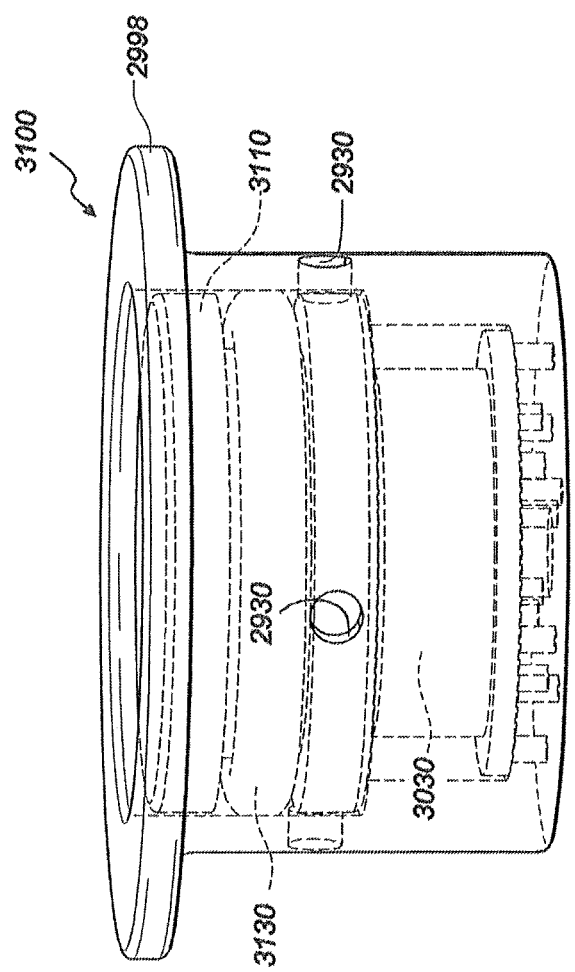
FIG. 31C is a perspective view of the deflation port 3100 of FIG. 31A, with portions shown in phantom, wherein the expanding device 3030 is in a contracted state so that the seal 3130 blocks the vents 2930.
Figure 31D:
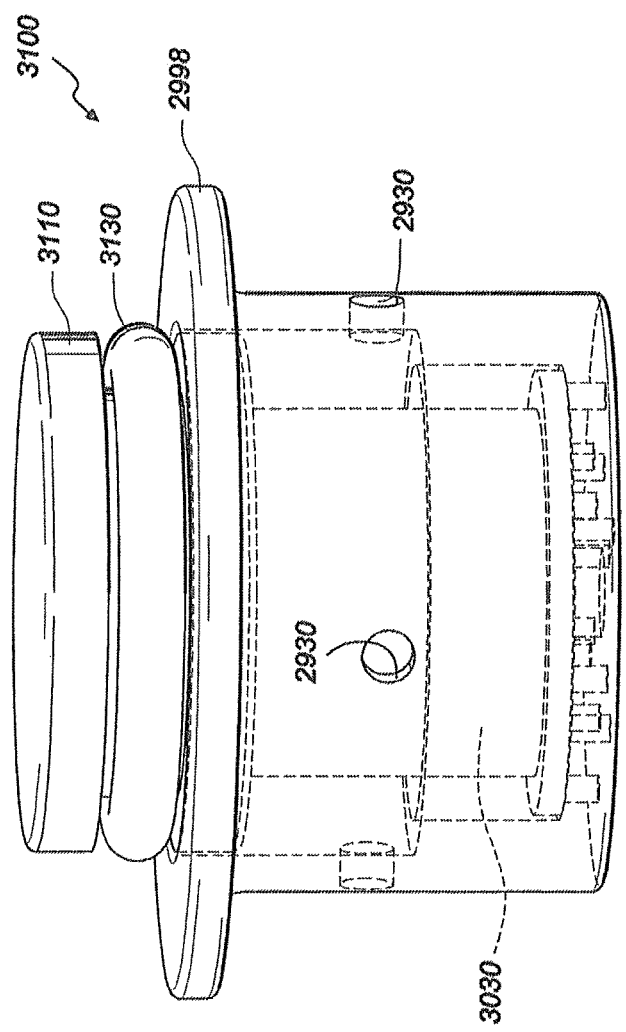
FIG. 31D is a perspective view of the deflation port 3100 of FIG. 31A, with portions shown in phantom, wherein the expanding device 3030 is in an expanded state so that the seal 3130 is displaced so as to open the vents 2930.

A preferred embodiment of manually inflated balloon that also possesses a mechanism for self-deflation would be a port that encompasses an inflation and deflation mechanism in the same location (See FIG. 30A). The device comprises a catheter needle sleeve, e.g., of nylon or plastic that seals to silicon parts, that is attached to inflation tube when filling. It further comprises a silicon head which seals to the needle sleeve, allowing for inflation and detachment from the catheter. The silicon head also seals to part # 6 until pushed out of position by expanding part #7. The needle, e.g., fabricated from stainless steel, inflates the balloon. A compression Seal between part #6 and #2 vents internal gas when displaced. An insert, e.g., of titanium, provides imaging visibility (FIG. 30B), and provides rigid support for parts #2 and #4, and interference locks, sliding fits, and press fits to part #6. A septum, e.g., of silicon, seals to part #3 during inflation. The casing, e.g., PEEK or hard plastic, bonds to the balloon outer film and provides a sealing surface to part #2. It contains vents from inside the balloon to outside the balloon after part #7 expands. The expanding device, e.g., polyacrylamide in a binder material surrounded by a controlled moisture vapor transmission rate material (assorted blends of polyurethanes in varying thicknesses) uses the moisture available inside the balloon to uptake and swell in size. The press fit between parts #5 and #6 holds the parts firmly in position until part #7 begins to expand from moisture uptake.

In preferred embodiments, the device includes a self-sealing valve that is compatible with an inflation catheter that contains a needle and needle sleeve. The self-sealing valve is sealed to the needle sleeve during the inflation process. Distal to the self-sealing valve is a titanium, stainless steel, MP35N, or any other radio-opaque rigid material insert that provides imaging visibility as well as mechanical support during the inflation process. Beneath the insert is the deflation mechanism that consists of an expanding device. The expanding device consists of a solute material, i.e. polyacrylamide material or the like encased in a binder material surrounded by moisture limiting material that has a defined moisture vapor transmission rate (MVTR). Moisture rate limiting material examples include but are not limited to assorted blends of polyurethanes in varying thicknesses. A hard plastic casing, such as PEEK, encompasses the self-sealing valves, the radio-opaque insert, the expanding material, and the moisture rate limiting material. The hard plastic case contains vents that would allow fluid to flow between the inside and outside of the balloon if the outer seal were not in position. The radio-opaque insert is coupled to the hard plastic casing via mechanical means, such as a press fit, that allow for linear movement but do not allow it to expel from the hard plastic casing. A second outer sealing valve creates an airtight seal to the hard plastic casing, blocking the casing vents, and moves linearly as the expanding device gains volume. Moisture placed inside of the balloon is absorbed by the expanding device as well as contributing moisture from the external gastric environment. Once the moisture transfers, the expanding material develops enough pressure such that the outer sealing valve is pushed linearly past the lip of the casing. This opens a vent pathway that allows the internal inflation fluid to quickly decompress and deflate the balloon. A deflated balloon allows for passing through the pylorus and through the remainder of the alimentary canal. One or multiple inflation/deflation ports on the surface of the balloon can be employed.

An alternative embodiment where the inflation port and deflation port are separate entities is depicted in FIG. 31. The device comprises a seal, e.g., of Buna rubber or similar sealing material, to provide an airtight seal between parts #1 and #3. It slides along the surface of part #3 until airtight seal fails and allows internal air out. The vent allows gas to flow from the balloon once the seals displaces. Also included are a titanium plunger, a water retainer (cotton or sponge-like material that is capable of retaining water and holding it against the surface of part #4 in order to maintain a constant moisture environment) and a casing of PEEK or other hard material that seals via adhesive to the balloon film and provides rigid containment for parts #1, 2, 4, and 5. The design also allows venting between internal and external balloon environment, and water ingress to part #4 which forces part #4 to expand in one direction. An expanding device, polyacrylamide in a binder material surrounded by a controlled moisture vapor transmission rate material (assorted blends of polyurethanes in varying thicknesses) uses the moisture available inside the balloon to uptake The device can include a hard outer casing made of hard plastic or metal, an expanding device consisting of a super absorbent core surrounded by a moisture vapor transmission rate limiting membrane, and an airtight seal that is able to move linearly while the moisture expanding device grows in volume. The expanding device expands at a given rate based on how much moisture is available to it. In order to control the rate of expansion, a membrane, such as polyurethane, is used to control the desired moisture vapor transmission rate that is available to the super absorbent device. The moisture vapor transmission rate can be tuned by material formulation or material thickness. In order to maintain constant moisture contact to the moisture vapor limiting membrane, a sponge like material, such as cotton, can be used as a moisture reservoir for the expanding device. Once the expanding device pushes the seal past the lip of the hard outer casing, fluid can vent from inside the balloon to the external environment, causing the balloon to deflate and pass through the pylorus and the remainder of the alimentary canal. The balloon can have at least one deflation port but may have as many as deemed necessary to deflate the balloon such that it completely deflates and no residual inflation fluid remains that would cause a bowel obstruction (i.e., partial deflation).

A mechanism to facilitate passing involves an erosion mechanism that allows for the balloon to be broken down into a size that has a higher probability of predictably passing through the lower gastrointestinal system. Preferably, the size of the balloon as deflated is less than 5 cm long and 2 cm thick (similar to various foreign objects of similar size that have been shown to pass predictably and easily through the pyloric sphincter). This can be accomplished by providing the balloon with "erodible seams." One seam that breaks the balloon open into (at a minimum) two halves, or more seams are provided so that a plurality of smaller balloon pieces is produced in the dissociation reaction (FIG. 18). The number of seams used can be selected based on the original surface area of the balloon and what is required to dissociate the balloon into pieces that are of a size that can predictably pass through the gastrointestinal tract more easily. The rate of seam erosion can be controlled by using a material affected by, e.g., the external gastric environment pH, liquid, humidity, temperature, or a combination thereof. Seams can be single layer consisting of only erodible material, or multi-layer. The timing of self-deflation can be further controlled by the design of the seam layers, e.g., making the reaction and/or degradation of the seam material dependent on the internal environment of the balloon instead of the external environment. By manipulating the reaction such that erosion or degradation is initiated by the internal environment (e.g., the balloon's internal pH, humidity, or other factors), any impact of person-to-person gastric variability (pH, etc.) that can affect erosion timing is minimized. The internal balloon environment can be manipulated by adding excess water at injection to create a more humid internal environment, or the amount of constituents added can be varied to manipulate the pH, etc.

EXAMPLE

A disposable Nitrogen Fill System and Procedure Canister devices are provided as accessories to the Obalon Gastric Balloon (OGB). In use, the cap is removed from the valve of a disposable Nitrogen Fill System. This disposable Nitrogen Fill System is inserted into a Procedure Canister and the lever is closed to engage the valve on the disposable canister. A lack of a fluid path of a lower pressure gradient keeps the fluid from expelling. The Procedure Canister is attached to an Accessory Kit via a luer fitting. A 3-port, 2 position valve on the Accessory Kit is confirmed closed before opening the 90° valve. Appropriate pressure is confirmed via the digital gauge, then a standard OGB System inflation procedure commences and the fluid path is opened to the balloon in the body. After the procedure, the disposable Nitrogen Fill System is removed from Procedure Canister and properly disposed of The Procedure Canister is re-used and can have a useful life, e.g., of at least 1 year.

The Nitrogen Fill System is an appropriate size to fit into the canister dispenser, e.g., a major outer diameter of the non-valved canister is 45±1 mm. The Nitrogen Fill System is an appropriate size to fit into the canister dispenser, e.g., a height of the non-valved canister is 115±1 mm. The Nitrogen Fill System is pressure resistant, e.g., having an 18 bar pressure resistance. The internal volume of the Nitrogen Fill System is adequate to fill a Balloon Kit at appropriate fill pressure, e.g., a brimful volume of non-valved canister is 161±3 cm3. The Nitrogen Fill System is accurately pressurized, e.g., sampling direct pressure measurement is within±1 psi or±7 kPa. The assembled Nitrogen Fill System is bubble tight, e.g., a pressurized disposable canisters is tested visually for leaks via a water bath bubble detection test. A volume of the canister allows for enough air at a pressure that is not great enough to rupture the catheter, .e.g., a pressure of fully pressurized canister is not to exceed 75 psi. The Procedure Canister has the ability to connect to the Balloon Kit. The Procedure Canister contains a luer fitting that connects to a swallow catheter. The Procedure Canister has an effective valve for inflation. The Nitrogen Fill System has a ¼ turn valve. The valve is designed for gas and has an operational pressure range which includes 1 to 75 psi. The Procedure Canister precisely displays pressure. The Procedure Canister contains a digital gauge with 0.01 psi resolution or 0.1 KPA resolution. The Pressurized Nitrogen Fill System is bubble tight, e.g., no bubbles per bubble leak test in 130° F. water bath for 1.5 minutes. The Nitrogen Fill System fills the balloon to proper pressure, e.g., 2.0+/−0.5 psi at sea level. The pressure is retained by the assembled Nitrogen Fill System effectively enough to not place balloon fill pressures outside of specification. The mass of contained gas is not to drop more than<5 psi over the course of 1 year. The Procedure Canister is reliable for at least 1 year, and the Procedure Canister is good for at least 1000 actuation cycles. The Procedure Canister is compatible with the Nitrogen Fill System. The Dynamic components of the Procedure Canister can cycle through intended range of motion with the disposable canister inserted.

The Procedure Canister opens the disposable canister valve when the receiver is closed. The Procedure Canister is capable of dispensing contents of the Nitrogen Fill System to support a total system procedure time goal of 5-10 minutes. The Fully pressurized Nitrogen Fill System can be dispensed within 30 seconds. The Procedure Canister's digital gauge provides advance notification of a low battery level.

The digital gauge contains a low battery indicator. Procedure Canister's digital gauge battery life shall be useful for the service life of the device. The digital gauge battery life is rated at least 2000 hours. The batteries are standard and replaceable in the field as needed. The digital gauge preserves the battery when not in use, e.g., by automatically shutting off 60 minutes from last button press. The Procedure Canister seals to the Nitrogen Fill System in such a way to prevent leaks. The Nitrogen Fill System engaged in the Procedure Canister does not leak more than 0.1 psi over 5 minutes. The Procedure Canister's Digital Pressure Gauge is electromagnetically compatible. The Procedure Canister's gauge readings are easy to read, e.g., the gauge size is at least 3" diameter with a digital display. The Procedure Canister's pressure gauge is intuitive to operate, e.g., the gauge has one touch on and off button that is clearly labeled. The actuator on Procedure Canister for inflation of the balloon is intuitive, e.g., a colored valve lever with only on and off positions is used for initial balloon fill from the Procedure Canister. The Nitrogen Fill System is easily inserted into the Procedure Canister, e.g., the Procedure Canister opening is large and obviously apparent.

The mass of nitrogen contained by Nitrogen Fill System is appropriate to attain a desired final balloon pressure, e.g., the Nitrogen Fill System sample is weighed before and after filling to assure 0.52±0.01 grams of gas. The Procedure Canister has a digital gauge with adequate accuracy to ensure final balloon pressure is attained, e.g., the Procedure Canister's digital gauge has an accuracy of 0.25% of Full Scale. The Procedure Canister has a digital gauge that maintains accuracy over its useful life, e.g., the Procedure Canister's digital gauge has an accuracy of 0.25% of Full Scale after 1000 cycles of 0 psi to 30 psi or 0 KPa to 26 kPa. The Nitrogen Fill System is preferably operated under reasonable environmental conditions, e.g., temperatures of from −18° C. to 55° C. and relative humidities of from 30% to 85%. The altitude classification system is used in altitude of a<2000 m (61 to 101 kPa).

The Obalon Gastric Balloon System (the "System" or OGB) is designed to assist weight loss by partially filling the stomach and inducing satiety. The System consists of up to 3 intragastric balloons that are placed non-invasively in the stomach (via a catheter-capsule assembly) and reside in the stomach for up to 3 months (12 weeks). For administration, each balloon is contained within a medical-grade porcine gelatin capsule, which is attached to a miniature catheter. The balloon capsule delivers the balloon in the same manner that a medicinal capsule delivers pharmaceuticals. The catheter comes pre-attached to the compacted Balloon's radio-opaque, re-sealing valve. For administration of the device (placement), the catheter/capsule is swallowed by the patient. The catheter is then attached to a Procedure Canister that contains a disposable Nitrogen Fill System that is used to fill the balloon. After the patient swallows the balloon capsule, radiography is done to ensure the balloon is in the stomach after swallow (visualized by the radio-opaque marker). The preferred radiographic method is fluoroscopy since it provides a real-time picture of the balloon using low levels of radiation. A fully inflated single balloon is an ellipsoid with a volume of approximately 250 cc. When 3 balloons are placed the total balloon volume is 750 cc. The administration procedure requires no sedation. After inflation is complete, the catheter is manually ejected from the balloon valve and retrieved by the physician; leaving the balloon free-floating in the patient's stomach for up to 3 months.

Balloon use can employ the concurrent use of Proton Pump Inhibitors for the duration of use, e.g., 40 mg/day of pantoprazol or an equivalent dosage of similar medications. It is likely an effective treatment for undiagnosed pre-existing esophagitis and gastritis which should enhance tolerability of the devices in residence. Antiemetic and spasmolytic agents can be given immediately following balloon placement and given as needed while the balloon(s) are in the stomach.

Clinical trials have shown that it is preferred to place one balloon initially and subsequent balloons be placed later in the 3 month period (FIG. 32). Determination of whether a patient requires additional volume should be made based on patient weight loss progress and reported satiety levels. Additional balloons are placed in the same manner as the first balloon placement; requiring only radiography for placement.

The balloon helps the patient eat less food at each sitting. The selection of less calorie dense foods in addition to the balloon(s) will only help facilitate weight loss. The balloons are intended to remain in the stomach for 3 months (12 weeks) from the time of placement of the first balloon. All balloons placed are removed at the end of three months using standard endoscopic methods. The device(s) are removed by a trained healthcare professional proficient in gastroscopy.

The health care setting in which the device is to be used has access to fluoroscopy or digital x-ray at the time the device is administered, to ascertain the balloon/capsule placement in the stomach prior to inflation. In addition, the prescribing physician has immediate access to an endoscopy unit and personnel proficient in gastroscopy and foreign object retrieval should problems arise during administration. Gastroscopy equipment and persons trained in foreign object retrieval are employed for device removal.

The Obalon Gastric Balloon System (the "System") is indicated for temporary use for weight loss in overweight and obese adults with a BMI of 27 or greater who have previously failed a supervised weight control program. The Obalon Gastric Balloon system is intended to be used in conjunction with a diet and behavior modification program. Up to 3 Obalon Gastric Balloons may be placed in the stomach across a 3-month (12-week) period based on the individual's weight loss progress and satiety levels. The maximum placement period for the Obalon Gastric Balloon(s) is 3 months (12-weeks) and all balloons must be removed at that time or earlier.

Figure 33:
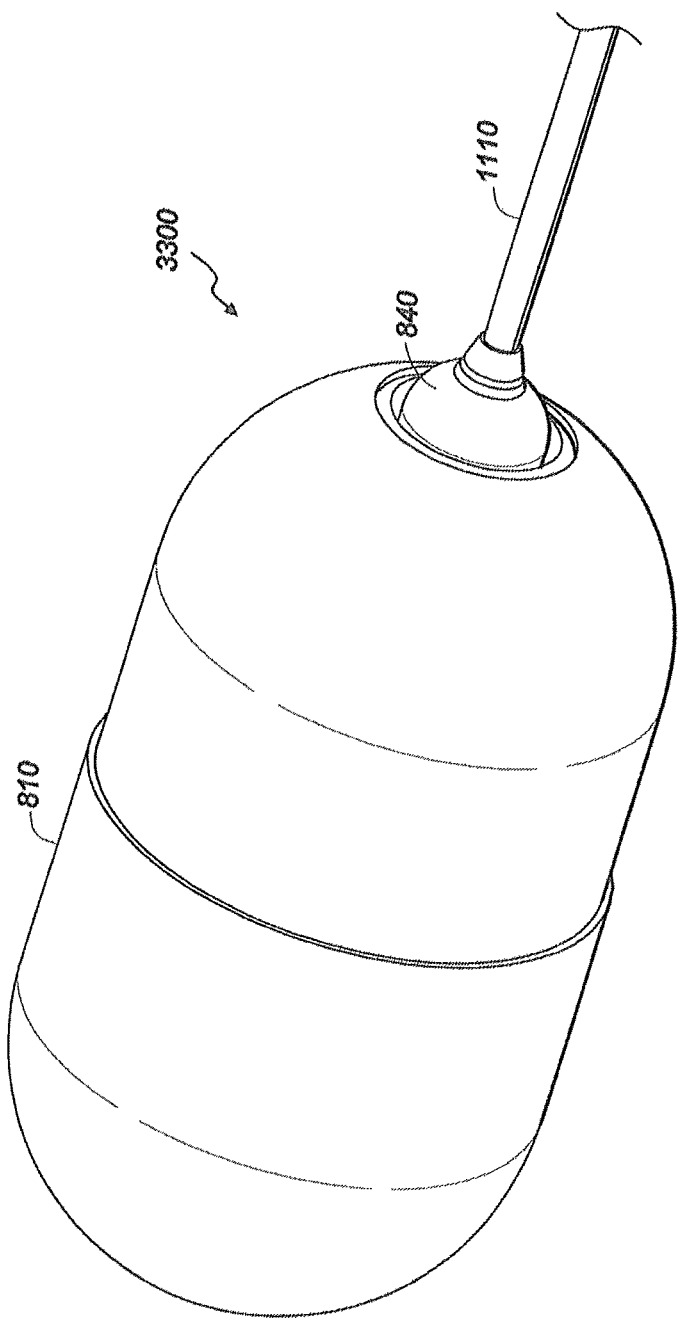
FIG. 33 is a perspective view of an Obalon Gastric Balloon Assembly 3300 including a balloon outer container or capsule 810 and inflation catheter 1110 with a bell-shaped needle sleeve 840.
Figure 34:
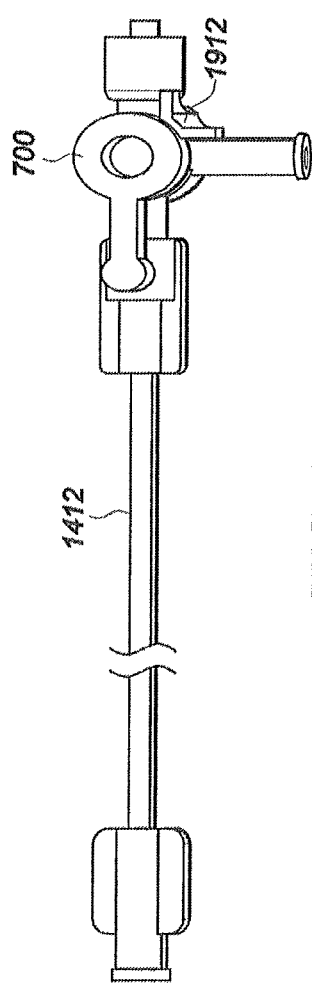
FIG. 34 depicts an extension tube 1420 and a 3-way valve 700 with a stopcock 1912 for use in conjunction with the Obalon Gastric Balloon Assembly 3300 of FIG. 33.
Figure 35:
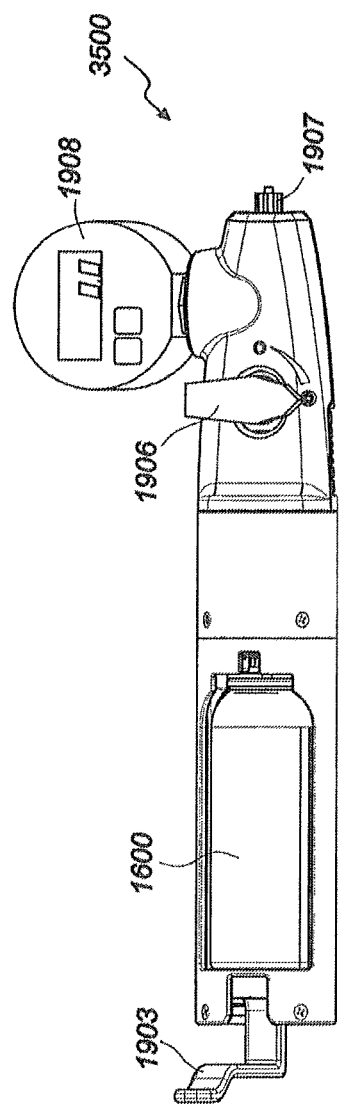
FIG. 35 is a perspective view of an inflation fluid dispenser or a Procedure Canister 3500 with disposable inflation fluid container or Nitrogen Fill System 1600 for use in conjunction with the Obalon Gastric Balloon Assembly 3300 of FIG. 33, the dispenser 3500 including a valve 1906, a luer connector 1907, a latch 1903 and a pressure gauge 1908.

All components are supplied non-sterile. The System can include the following: a Placebo Capsule Assembly including a capsule of the same material, size, shape and weight as the actual device but that does not contain a balloon or catheter. The capsule is filled with food-grade sugar to simulate device weight; an Obalon Gastric Balloon Assembly including one folded balloon contained in a swallowable Gelatin Capsule and attached to 1 disposable, flexible Catheter Delivery System (FIG. 33); an Accessory Kit including two 3 $cm^3$ Syringes, an extension tube and stopcock with a 3-way valve (FIG. 34), and a 60 $cm^3$ syringe; a Procedure Canister which is a reusable component and is used in conjunction with the disposable Nitrogen Fill System with the Digital Pressure Gauge attached (FIG. 35); two AAA Batteries; and a Nitrogen Fill System filled with 150 cm3 of nitrogen. Other items that can be used in conjunction with administering and/or removing the System include a small clean bowl, bottled water, timer/clock, digital X-Ray or fluoroscope, vacuum aspiration source, gastroscope, gastroscope Injection Needle (minimum length can be 6 mm and minimum needle gauge size can be 23) compatible with the working channel of the gastroscope, and a rat tooth with alligator jaws grasping forceps (minimum opening width can be 15 mm) or other commercially available endoscopy retrieval tools such as two-prong graspers, compatible with the working channel of the gastroscope.

The Procedure Canister is prepared for use by first ensuring that the Procedure Canister is correct for the altitude of the facility or contains a barometric pressure compensation valve to adjust the starting pressure to ensure proper balloon end pressure. Failure to use the correct Procedure Canister can result in a deflated or over inflated balloon.

Figure 38:
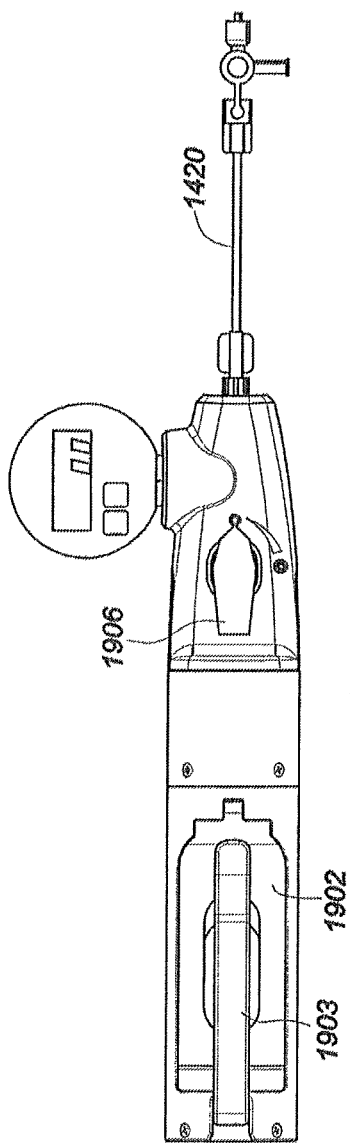
FIG. 38 depicts the valve 3520 of the dispenser 3500 in the 'open' position and attached to the extension tube 1911 of FIG. 34.
Figure 39:
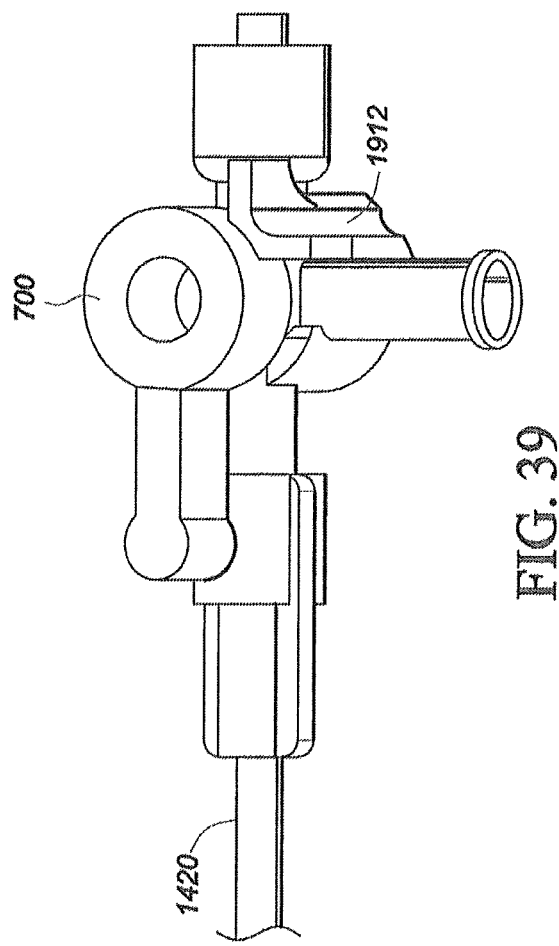
FIG. 39 is an enlarged view of the stopcock 1912 of the extension tube 1911 of FIG. 34, wherein the three way valve 700 in the 'closed' position.
Figure 42:
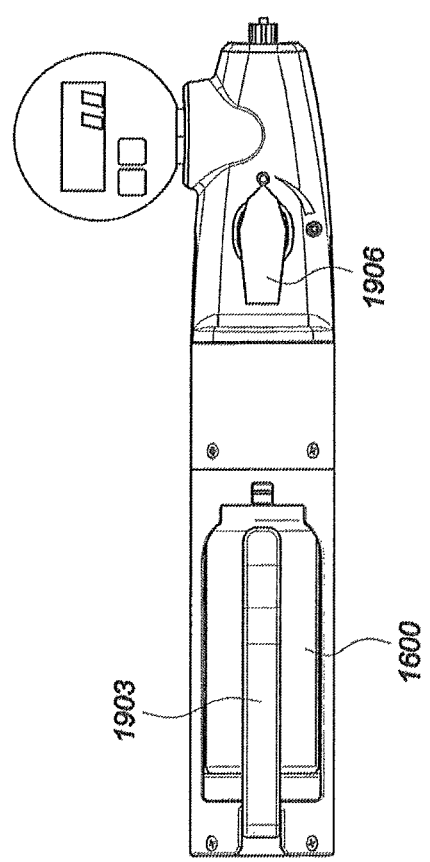
FIG. 42 depicts the dispenser 3500 of FIG. 35 with lever 1903 in the closed position and valve 1906 in the 'open' position after receiving the disposable Nitrogen Fill System 1600.
Figure 43:
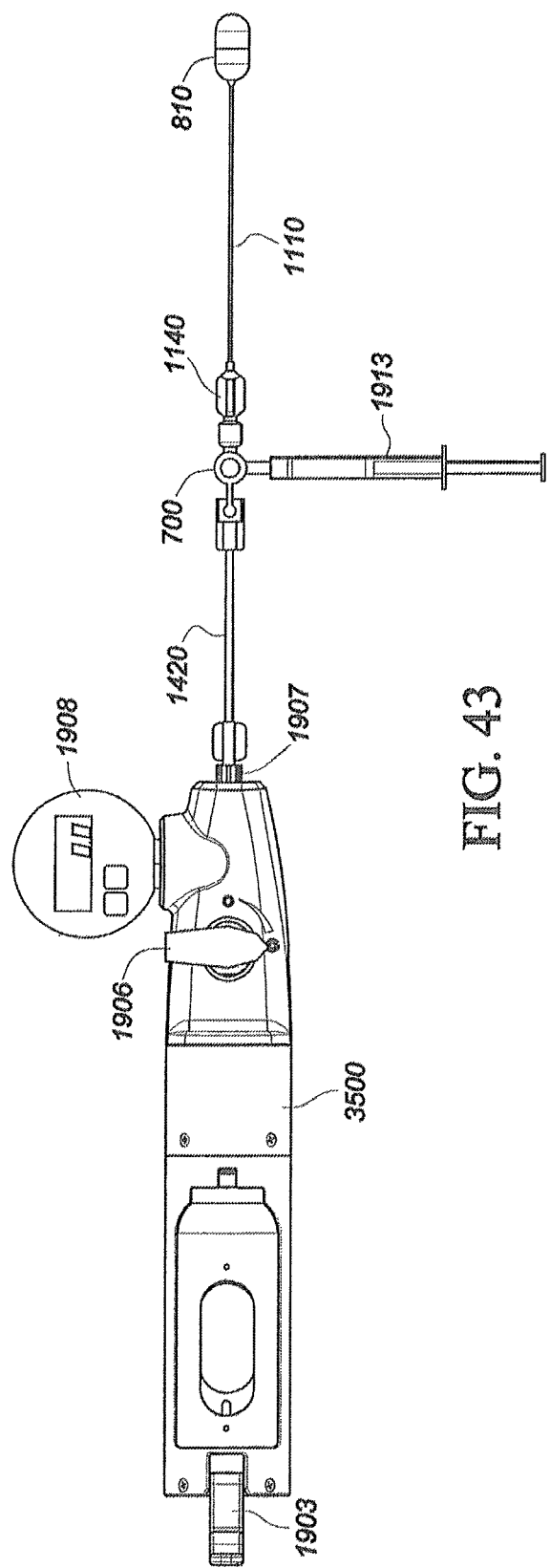
FIG. 43 depicts the valve 1906 of the dispenser 3500 in the 'closed' position and the balloon ejection syringe 1913 and Obalon Gastric Balloon Assembly 3300 attached to the extension tube 1420 via the 3-way valve 700, wherein the three way valve 700 is positioned for ejecting the balloon using the syringe 1913.

The Procedure Canister valve is in the open position (FIG. 36). The "ON" button is pressed to turn on the Procedure Canister Gauge. The extension tube and stopcock with 3-way valve is removed from the Accessory Kit packaging. The luer lock plug is removed from the end of the Procedure Canister Gauge (FIG. 37). The luer lock plug is saved and put back on the Procedure Canister after the procedure is complete to keep the Procedure Canister free of debris. The proximal end of the luer connector of the extension tube (from the Accessory Kit) is connected to the Procedure Canister (FIG. 38) with valve open. The stop cock valve is in the closed position to stop the flow of gas (FIG. 39). The cap is removed from the Disposable Canister. The canister is configured to not fit into the Canister Dispenser if this cap is not removed (FIG. 40). With the lever in the 'open' position, the disposable Nitrogen Fill System is inserted straight down into the Canister Dispenser (FIG. 41). The lever is set to the 'closed' position to secure the disposable Nitrogen Fill System in place (FIG. 42). The initial reading on the gauge is confirmed to be between 257 kPa and 297 kPa, to ensure proper balloon inflation. The valve on the Procedure Canister is closed by rotating the valve clockwise (to the right) (FIG. 43). The Procedure Canister valve is in the closed position before proceeding to next steps to ensure the proper positioning and status of the balloon capsule prior to proceeding to the balloon fill step. The 3 $cm^3$ syringe is removed from its packaging and filled with 1.5 ml of room temperature water and set aside. A small clean bowl halfway with water. The Obalon Gastric Balloon Capsule and Catheter Delivery System are removed from their packaging.

Prior to the patient swallowing the functioning device, it is recommended that they first swallow the placebo capsule. The purpose of this procedure is to determine which patients will and will not be good candidates to have the actual device placed. The placebo capsule should go down easily. If the patient swallows the placebo capsule without problem it is recommended that they proceed with the Balloon therapy.

The Obalon Balloon capsule is administered to the patient using a normal pill swallowing method. Endoscopy is not required for placement. Fluoroscopy (or digital x-ray) is employed during the placement procedure to verify placement of the balloon in the stomach prior to inflation of the device. Any existing balloons are also imaged to confirm their integrity prior to swallowing another capsule. The total placement time is less than 15 minutes for each balloon placed.

Should a patient have a strong gag reflex, a topical anesthetic may be applied immediately before capsule administration. To place the balloon, it is preferred that the patient has no lipstick, gloss, or emollients on their lips that could affect the administration process. The patient preferably stands or sits upright, and three large gulps of water are administered to prepare for capsule administration. The patient can be instructed not to bite down on the catheter, to close his/her mouth on catheter, to hold onto the catheter by hand, or to grab the catheter. The Capsule/Catheter is wet by submerging into the bowl of water for no more than 10 seconds. Within 1 minute of submerging the capsule in the water, the patient is handed the capsule/catheter and instructed to place the capsule immediately in the mouth and swallow the capsule with another large glass of water. The Proximal Catheter Port is held outside of the patient's mouth. The time of placement of the capsule/catheter in the mouth for swallow is documented. The patient is given additional water or juice (at least 100 ml) after swallow. The patient remains in an upright sitting or standing position the entire time. The patient is asked to continually drink water or juice to facilitate peristalsis of the capsule/catheter if the balloon has not visibly passed into the stomach. Once swallowed, the proximal end of the capsule/catheter assembly remains outside of the patients' mouth until after the balloon is filled. The catheter may have markings that are to be used as a reference guide to help determine how far the catheter has traveled after swallow or to be used with or without the radiography verification and with or without measurement provided by the digital gauge. When the 'bull's-eye' marking is at the patient's teeth, this indicates that the balloon is approximately 45 cm down the esophagus and fluoroscopy is used at this time to determine if the balloon is in the stomach (FIG. 44). The preferred method to confirm proper balloon placement prior to inflation is with radiography (fluoroscopy/digital x-ray). The catheter markings can be used for additional reference as to when to properly perform the radiography or could be used alone to verify the length traveled into the stomach.

The Procedure Canister with the extension tube from the Accessory Kit is connected to the balloon catheter by connecting the catheter to the male luer port on the 3-way stopcock of the extension line previously connected to the Procedure Canister (FIG. 45). The lure fittings are tightened snugly with fingers. The valve on the Procedure Canister is in the closed position before proceeding to next steps to ensure the proper positioning and status of the balloon capsule prior to proceeding to the balloon fill.

Figure 46:
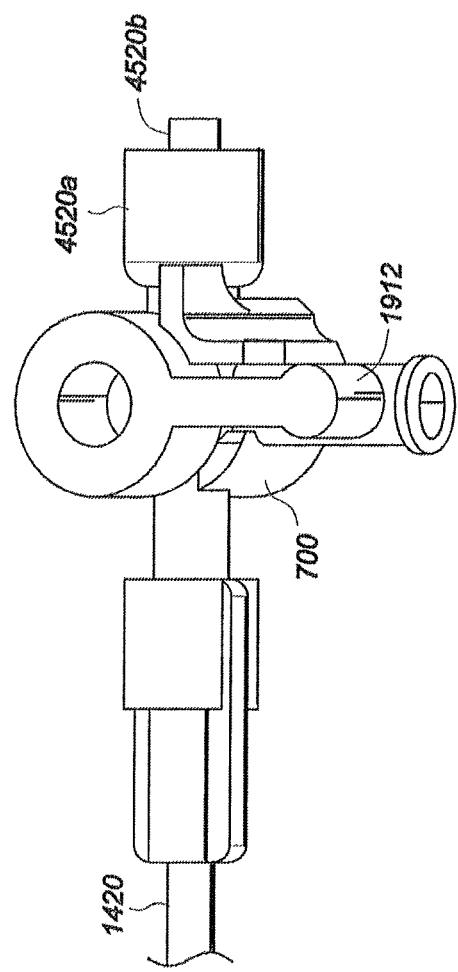
FIG. 46 is an enlarge perspective view of the stopcock 1912 of the extension tube 1420 with three way valve 700 in the 'open' position.

Approximately 1-2 minutes after swallow, digital x-ray or fluoroscopy is performed with the patient standing or sitting upright, to determine location of the radio-opaque balloon marker in the stomach. At least 3-5 minutes after swallow, a second verification of device location is performed using the Procedure Canister. This is accomplished by turning the Procedure Canister Digital Gauge on by pressing the "ON" button, turning on the Gauge Backlight, pressing the "ON" button on again, and turning the 3-way valve on the stopcock counterclockwise 90 degrees until the valve stops to open the flow of gas from extension tubing to the balloon (FIG. 46). The pressure initially drops on the pressure gauge by approximately 20 kPa and then proceeds to below 7 kPa when the capsule dissolves. This takes approximately 45 seconds but no longer than 4 minutes. If the pressure remains above 7 kPa, then the capsule has not dissolved sufficiently or the catheter is kinked. Having the patient drink more liquid may facilitate capsule dissolution. The pressure is monitored for up to 4 minutes. If after this time the pressure has not dropped to less than 7.0 kPa then the capsule has not dissolved or there is a kink in the catheter. Balloon fill steps are not initiated until the radio-opaque balloon valve is visualized in the stomach and the Procedure Canister pressure gauge reads less than 7.0 kPa. During inflation, if there is indication of inflation in a constrained space (by pressure readings or patient symptoms) shut off the gas flow by closing the valve on the Procedure Canister, detach the catheter from the Procedure Canister, and evacuate the gas from the balloon with a 60 cm3 syringe. The balloon can then be removed endoscopically. If the gauge reads less than 7.0 kPa, then the balloon can be filled. The balloon is not disconnected from the catheter prior to balloon fill completion. In the event of a premature disconnect, the catheter is retrieved by pulling it out and then the balloon is endoscopically punctured and removed.

Figure 47:
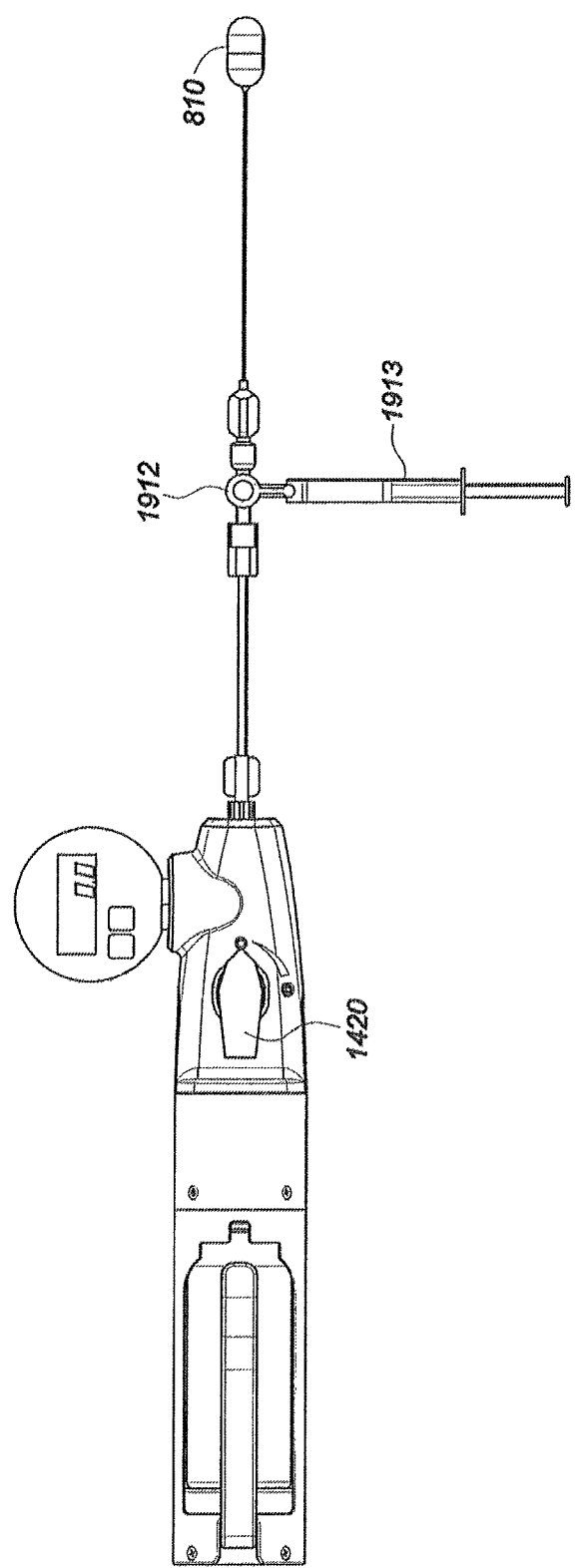
FIG. 47 depicts the stopcock 3-way valve 700 of the dispenser 3500 of FIG. 43 in the 'open' position and the Balloon Ejection Syringe 4300 and Obalon Gastric Balloon Assembly 3300 attached to the Extension Tube 1911 via the three way valve 700.

The Disposable Nitrogen Canister contains 150 cm$^3$ of nitrogen that is transferred into the balloon to fill a single balloon to 8.3-17.2 kPa and 250 cm$^3$ of volume. When the gauge remains steady after decreasing from the initial set inflation pressure, the balloon is filled to the desired volume of 250 cm$^3$ at the desired pressure of 13.8 kPa in approximately 2 minutes. To fill the balloon, the Procedure Canister valve is turned to the on/open position (FIG. 47). Equilibrium is observed about 2 minutes after opening the valve (inflation time). The final readout pressure on the Procedure Canister's digital gauge is verified as stable and reading 8.3-17.2 kPa. If the pressure is outside of the specified range, endoscopic removal of the balloon is performed. The pre-filled Syringe is attached to the Stopcock with a 3-way Valve. The Stopcock with a 3-way Valve is rotated back 90 degrees to close the flow of gas from the Procedure Canister (FIG. 48). The 3 way stopcock valve is not rotated until attached to the pre-filled syringe so as to avoid reducing the final starting pressure in the balloon such that the balloon may not maintain its volume for the 3 month period. The gauge is not zeroed by holding the zero button while pressure is being transferred, to avoid the need to then remove the balloon endoscopically.

The catheter is retrieved by pushing the 1.5 cm3 filled Syringe plunger in one rapid and deliberate motion, so as to detach the catheter from the balloon valve in the stomach. If the catheter does not detach after the first attempt, the second 1.5 cm3 water filled syringe can be used to again attempt to remove the catheter. On the second attempt, it is ensured that the catheter is straight (there are no kinks) and that the plunger is pressed in a rapid and deliberate motion. Force is used when pushing the Syringe, and the step is not performed slowly to avoid the catheter not ejecting properly. If catheter remains attached to the balloon, a second 3 ml syringe can be half way filled with water, and detachment can again be attempted. To facilitate detachment, the patient lifts his/her chin up to help reduce any gag reflex, then the catheter is slowly pulled out of the patient's mouth. The catheter and the needle inside the needle sleeve are visualized (white protective hub that came attached to the capsule device) to ensure the needle is intact. If the needle is not inside the needle sleeve, then the balloon is removed. The catheter is separated from the Stopcock with a 3-way Valve by unscrewing the luer lock. The location of the balloon can be re-verified using X-ray or fluoroscopy.

The disposable Nitrogen Fill System can be removed from the Procedure Canister and discarded. To remove, the Procedure Canister lever is moved to the 'open' position, and the Nitrogen Fill System is pushed up from the opposite side of the Procedure Canister, or the Procedure Canister is flipped upside down and the disposable Nitrogen Fill System naturally falls out. The Procedure Canister is reused for the next balloon placement.

The patient can be advised to drink liquids for the first 24 hours and then transition to soft solids for the next 24 hours (in the first 48-hours after placement). Patients are instructed not drink alcohol, sodas or other "fizzy" or carbonated drinks. After 3 days patients are able to return to solid foods and follow the diet and behavior modification program provided to them by their physician.

While placement of the balloon does not require endoscopy; it can be desirable that a trained endoscopist be readily available should there be a problem with swallow of the balloon or an undiscovered swallowing disorder is detected during the procedure. The following should be considered if a patient is unsuccessful at his/her first placement attempt. If the device does not pass the pharynx in the patient's mouth after 30 seconds of attempting swallow, the capsule is removed from the mouth. A new wetted balloon capsule/catheter assembly is used. If the patient fails two attempts, this issue is discussed with the patient and it is determined if the patient remains a good candidate for the therapy. If the failure to swallow is due to anxiety, standard methods to reduce the patient's anxiety can be used. Esophageal transit of the device can be facilitated by use of clear carbonated beverages.

Patients are advised to report a change in satiety (i.e. increased hunger), and/or weight gain as this may be a sign that an additional balloon for therapy might be warranted. If multiple balloons have been placed and the patient reports a change in satiety levels (i.e. reduced early satiety), this may be a sign of balloon deflation. Balloon deflation can be evaluated using radiography (film x-ray, digital x-ray, or fluoroscopy) and gastroscopy as appropriate. Patients are advised to contact their physician if the frequency of adverse events experienced is more than anticipated or becomes intolerable. Concurrent use of Proton Pump Inhibitors can be desirable for the duration of use, e.g., 40 mg/day of pantoprazole or an equivalent dosage of similar medications, in that it is likely an effective treatment for undiagnosed pre-existing esophagitis and gastritis which may enhance tolerability of the devices in residence. Antiemetic and spasmolytic agents can be given immediately following balloon placement and given as needed while the balloon(s) are in the stomach.

After 12 weeks of use the balloon or balloons are removed from the patient. The procedure is conducted using a working length endoscope less than 1200 mm and the inner diameter is compatible with the accessory tools suggested for puncture and retrieval of the balloon. Suggested tools include a needle instrument, e.g., an injector needle in a Teflon Sleeve 23G×6 mm or similar having a lumen for suction, a Rat Tooth Grasper with Alligator Jaws or Two Jaw Grasping Forceps (with a minimum opening width of 15 mm); or a two prong graspers with same minimum opening. Other retrieval tools may be acceptable for retrieving the balloons. Retrieval procedures in general are conducted per the gastroscope manufacturer's instructions for retrieving foreign objects. The endoscopy procedure performed is similar to that of an interventional or therapeutic procedure, however tailoring the endoscopic approach according to the unique product features is recommended, e.g., balloons should only be punctured once, so that the maximum amount of gas can be aspirated (via vacuum) from them, and a lesser degree of stomach inflation (less air insufflation) allows for easier puncture of the balloon. A typical capsule may include as ingredients porcine gelatin, water, methylparaben, propylparaben, and sodium lauryl sulfate. A typical balloon may be constructed from nylon and polyethylene (as wall materials), silicone (in the valve), and titanium (as a radioopaque component). The procedure canister is typically constructed of Stainless Steel, 6061 AL, Brass, Acetal, and Silicone. The Nitrogen Fill System contains 150 cm$^3$ of Nitrogen at 18 barr.

Preferably, patients are fasted at least 24 hours or per hospital protocol for gastroscope procedures to ensure the stomach is empty and the balloon(s) are therefore easily visible. The patient is anesthetized per hospital and physician recommendations for gastroscope procedures. The gastroscope is inserted into the patient's stomach, and a clear view of the filled balloons is obtained through the gastroscope. The needle instrument is inserted down the working channel of the gastroscope. The valve of the balloon is located and the balloon is punctured with the needle only once (at the opposite end of the valve if possible for easier removal). Suction is applied and balloon gas is aspirated using a large syringe (60 cc) or aspiration tube. The needle is removed from the working channel, and the graspers are inserted through the working channel. The balloon is grabbed with the graspers at the opposite end of the valve. With a firm grasp on the balloon, the balloon is slowly extracted up through the esophagus, removing the balloon through the mouth. The removal procedure is repeated for the remainder of the balloons, if any.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

All references cited herein are incorporated herein by reference in their entirety. To the extent publications and patents or patent applications incorporated by reference contradict the disclosure contained in the specification, the specification is intended to supersede and/or take precedence over any such contradictory material.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, un-recited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A device for assisting a patient in swallowing an intragastric balloon, comprising:
   an elongate tube comprising a body and an elongate slit, the body having a through-bore extending from a first orifice of the elongate tube to a second orifice of the elongate tube, wherein the elongate slit extends through the body from the first orifice to the second orifice;
   a gastric balloon assembly reversibly attached to the second orifice, the gastric balloon assembly comprising an inflation catheter engaged with a gastric balloon in a capsule and extending out of the first orifice, wherein the elongate slit is sized and shaped for the inflation catheter to pass therethrough, and wherein the gastric balloon assembly is attached to the first orifice by a press-fit;
   a handle member; and
   an engagement subassembly comprising a female portion and a male portion, wherein the engagement subassembly is configured and arranged for threading the inflation catheter into and engaging the elongate tube.

2. The device according to claim 1, wherein the body comprises a biocompatible polymer.

3. The device according to claim 1, wherein the body is flexible.

4. The device according to claim 1, wherein the elongate tube is adapted to be detached from the gastric balloon assembly by tugging on the tubing.

5. The device according to claim 1, wherein the elongate tube is adapted to be detached from the gastric balloon assembly by an automatic ejection mechanism actuated by an internal pressure of the gastric balloon in an inflated state.

6. The device according to claim 1, wherein the female portion comprises a female body sized and shaped to be rotatably received within an engagement chamber of an engagement portion of the engagement subassembly.

7. The device according to claim 6, wherein the female body comprises a longitudinally extending chamber and a longitudinal guide structure joined with a perpendicular guide structure, wherein the longitudinally extending chamber extends from a front opening and a rear opening of the female body.

8. The device according to claim 7, wherein the female body includes coaxially aligned forward, middle and rear portions, and a separating extension which extends inwardly from a rear end of a middle portion of the of the longitudinally extending chamber.

9. The device according to claim 8, wherein the elongate tube comprises an engagement notch adapted to engage the separating extension and guide the separating extension into the elongate slit.

10. The device according to claim 8, wherein the elongate tube is adapted to be received into a through-bore of the engagement subassembly and encounter the separating extension when pushed forwardly into a rear portion of the longitudinally extending chamber.

11. The device according to claim 10, wherein the elongate tube is adapted to be rotated in the through-bore of the engagement subassembly until the elongate slit engages the separating extension, and is adapted to be inserted through the longitudinally extending chamber whereby the separating extension progressively pushes the elongate slit into an opened position for receiving the inflation catheter therein.

12. The device according to claim 1, wherein the male portion is adapted to be received into and rotatably engage with the female portion.

13. The device according to claim 12, wherein the male portion comprises a male body with an external portion joined with an internal portion, wherein the external portion extends longitudinally out of the engagement subassembly so as to be actuatable or adjustable by an operator.

14. The device according to claim 12, wherein the internal portion of the male portion is sized and shaped to be rotatably received into and interlock with the forward and middle portions of the female portion.

15. The device according to claim 14, wherein the internal portion comprises a plurality of beams that are contoured or otherwise sized and shaped to snap into and interlock with the middle portion of the female portion.

16. The device according to claim 15, wherein the internal portion comprises a guide post that extends outwardly from one of the plurality of beams and that is sized and shaped to be sliding engaged with a perpendicular guide structure of the female portion, wherein when an engagement portion of the female portion is in an opened configuration, the guide post is engaged with a rear wall of the perpendicular guide structure, wherein when the engagement portion is in an closed configuration, the guide post is engaged with a longitudinal guide structure of the female portion, and wherein the male portion is adapted to be rotated about a longitudinal axis with respect to female portion.

17. The device according to claim 16, wherein the male body comprises a longitudinally extending through-bore with a longitudinally running and inwardly extending zipper wedge and a longitudinally extending guide channel, wherein when the guide post is in an opened position, the longitudinal guide structure and the guide channel are vertically aligned with one another, such that a first end of the inflation catheter can be inserted through both the longitudinal guide structure and the guide channel and into the through-bore.

18. A method for assisting a patient in swallowing a gastric balloon assembly, comprising:
   providing the device of claim 1;
   holding the handle member;
   placing the capsule at a back of a patient's throat;
   detaching the capsule from a first end of the elongate tube;
   withdrawing the elongate tube from a mouth of the patient; and
   passing the inflation catheter of the gastric balloon assembly through the elongate slit of the elongate tube.

* * * * *

UNITED STATES PATENT AND TRADEMARK OFFICE
CERTIFICATE OF CORRECTION

PATENT NO. : 10,335,303 B2
APPLICATION NO. : 15/344309
DATED : July 2, 2019
INVENTOR(S) : Mark C. Brister It is certified that error appears in the above-identified patent and that said Letters Patent is hereby corrected as shown below:

On the Title Page

On page 3, Column 2, item [56], other publications, Line 18, delete "Suuplement" and insert -- Supplement --, therefor.

On page 3, Column 2, item [56], other publications, Line 25, delete "Ballon" and insert -- Balloon --, therefor.

On page 3, Column 2, item [56], other publications, Line 34, delete "Ingtragastric" and insert -- Intragastric --, therefor.

On page 3, Column 2, item [56], other publications, Line 56, delete "Ballon" and insert -- Balloon --, therefor.

In the Specification

Column 7, Line 41, delete "1A" and insert -- 1A. --, therefor.

Column 7, Line 56, delete "FIG." and insert -- FIGS. --, therefor.

Column 8, Line 13, delete "FIGS" and insert -- FIGS. --, therefor.

Column 11, Line 49, delete "72940," and insert -- 2940, --, therefor.

Column 16, Line 3, delete "radioopacity" and insert -- radiopacity --, therefor.

Column 17, Line 14, delete "is are" and insert -- are --, therefor.

Column 18, Line 21, delete "Assembley" and insert -- Assembly --, therefor.

Signed and Sealed this
Eighteenth Day of February, 2020

Andrei Iancu
*Director of the United States Patent and Trademark Office*

CERTIFICATE OF CORRECTION (continued)
U.S. Pat. No. 10,335,303 B2

Column 25, Line 15, delete "of the of the" and insert -- of the --, therefor.

Column 35, Line 13, delete "(FIG." and insert -- (FIGS. --, therefor.

Column 37, Line 15, delete "(FIG." and insert -- (FIGS. --, therefor.

Columns 40 and 41, Lines 59-67 and 1-2 (respectively), delete "For example.....inflation." and insert the same in Column 40, Line 58, as the continuation of same paragraph.

Column 60, Line 8, delete "(FIG." and insert -- (FIGS. --, therefor.

Column 62, Line 52, delete "of The" and insert -- of. The --, therefor.

Column 62, Line 64, delete "within±1" and insert -- within ±1 --, therefor.

Column 69, Line 28, delete "radioopaque" and insert -- radiopaque --, therefor.

Column 69, Line 32, delete "barr." and insert -- bar. --, therefor.

In the Claims

Column 71, Line 51, Claim 8, delete "of the of the" and insert -- of the --, therefor.